(12) United States Patent
Yue et al.

(10) Patent No.: US 9,737,516 B2
(45) Date of Patent: Aug. 22, 2017

(54) BICYCLIC HETEROCYCLES AS BET PROTEIN INHIBITORS

(71) Applicant: Incyte Corporation, Wilmington, DE (US)

(72) Inventors: Eddy W. Yue, Landenberg, PA (US); Andrew P. Combs, Kennett Square, PA (US); Andrew W. Buesking, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/088,373

(22) Filed: Apr. 1, 2016

(65) Prior Publication Data

US 2016/0213654 A1    Jul. 28, 2016

Related U.S. Application Data

(63) Continuation of application No. 14/554,263, filed on Nov. 26, 2014, now Pat. No. 9,315,501.

(60) Provisional application No. 61/908,954, filed on Nov. 26, 2013.

(51) Int. Cl.
| | | |
|---|---|---|
| *A61K 31/437* | (2006.01) | |
| *C07D 471/04* | (2006.01) | |
| *A61K 31/4545* | (2006.01) | |

(52) U.S. Cl.
CPC ........ *A61K 31/437* (2013.01); *A61K 31/4545* (2013.01); *C07D 471/04* (2013.01)

(58) Field of Classification Search
CPC .................................................. A61K 31/437
USPC .................................................. 514/300, 303
See application file for complete search history.

(56) References Cited

U.S. PATENT DOCUMENTS

| | | | |
|---|---|---|---|
| 5,589,476 A | 12/1996 | Jegham et al. | |
| 8,633,186 B2 | 1/2014 | Tachdjian et al. | |
| 8,669,249 B2 | 3/2014 | Brown et al. | |
| 9,012,642 B2 | 4/2015 | Haydar et al. | |
| 9,227,985 B2 | 1/2016 | Combs et al. | |
| 9,290,514 B2 | 3/2016 | Combs et al. | |
| 9,309,246 B2 | 4/2016 | Rodgers et al. | |
| 9,315,501 B2 | 4/2016 | Yue et al. | |
| 9,399,640 B2 | 7/2016 | Yue et al. | |
| 9,527,864 B2 | 12/2016 | Combs et al. | |
| 9,533,997 B2 | 1/2017 | Combs et al. | |
| 9,540,368 B2 | 1/2017 | Combs et al. | |
| 2002/0004510 A1 | 1/2002 | McCall et al. | |
| 2007/0191447 A1 | 8/2007 | Kodo et al. | |
| 2007/0244096 A1 | 10/2007 | Fox et al. | |
| 2008/0306093 A1 | 12/2008 | Servant et al. | |
| 2009/0306122 A1 | 12/2009 | Staehle et al. | |
| 2013/0045229 A1 | 2/2013 | Iadonato et al. | |
| 2013/0261109 A1 | 10/2013 | Miyoshi et al. | |
| 2013/0281396 A1 | 10/2013 | McLure et al. | |
| 2013/0281397 A1 | 10/2013 | McLure et al. | |
| 2013/0281398 A1 | 10/2013 | McLure et al. | |
| 2013/0281399 A1 | 10/2013 | McLure et al. | |
| 2014/0135316 A1 | 5/2014 | Albrecht et al. | |
| 2014/0275030 A1 | 9/2014 | Combs et al. | |
| 2015/0011540 A1 | 1/2015 | Combs et al. | |
| 2015/0148342 A1 | 5/2015 | Yue et al. | |
| 2015/0148372 A1 | 5/2015 | Yue et al. | |
| 2015/0148375 A1 | 5/2015 | Yue et al. | |
| 2015/0175604 A1 | 6/2015 | Rodgers et al. | |
| 2015/0307493 A1 | 10/2015 | Combs et al. | |
| 2016/0046650 A1 | 2/2016 | Combs et al. | |
| 2016/0075721 A1 | 3/2016 | Combs et al. | |
| 2016/0159817 A1 | 6/2016 | Combs et al. | |
| 2016/0168148 A1 | 6/2016 | Shepard | |
| 2016/0331749 A1 | 11/2016 | Bogdan et al. | |
| 2017/0014418 A1 | 1/2017 | Yue et al. | |

FOREIGN PATENT DOCUMENTS

| | | |
|---|---|---|
| CA | 2171579 | 9/1996 |
| EP | 0 732 334 | 9/1996 |
| EP | 1462103 | 9/2004 |
| EP | 2 239 264 | 10/2010 |
| EP | 2415767 | 2/2012 |
| EP | 2568287 | 3/2013 |
| EP | 2573559 | 3/2013 |
| FR | 2747678 | 10/1997 |
| JP | H 03014566 | 1/1991 |
| JP | H 05-097849 | 4/1993 |
| JP | 2013/010719 | 1/2013 |
| WO | WO 02/00196 | 1/2002 |
| WO | WO 2004/024736 | 3/2004 |
| WO | WO 2005/099688 | 10/2005 |
| WO | WO 2006/124874 | 11/2006 |
| WO | WO 2007/018998 | 2/2007 |
| WO | WO 2008/154221 | 12/2008 |
| WO | WO 2009/020559 | 2/2009 |
| WO | WO 2009/020677 | 2/2009 |
| WO | WO 2009/084693 | 7/2009 |
| WO | WO 2010/046190 | 4/2010 |

(Continued)

OTHER PUBLICATIONS

Ai et al., "Signal-induced Brd4 release from chromatin is essential for its role transition from chromatin targeting to transcriptional regulation," Nucleic Acids Res., 2011, 1-13.
Bamborough et al., "Fragment-Based Discovery of Bromodomain Inhibitors Part 2: Optimization of Phenylisoxazole Sulfonamides," J Med Chem., 2012, 55:587-596.
Bartholomeeusen et al., "BET bromodomain inhibition activates transcription via a transient release of P-TEFb from 7SK snRNP," JBC, 2012, 16 pages.
Bauer, "Pharmaceutical Solids—The Amorphous Phase," Journal of Validation Technology, Jan. 2009, 15(3): 63-68.
Belkina and Denis, "BET domain co-regulators in obesity inflammation and cancer," Nat Rev Cancer, Jul. 2012, 12:465-477.

(Continued)

*Primary Examiner* — Niloofar Rahmani
(74) *Attorney, Agent, or Firm* — Fish & Richardson P.C.

(57) ABSTRACT

The present invention relates to bicyclic heterocycles which are inhibitors of BET proteins such as BRD2, BRD3, BRD4, and BRD-t and are useful in the treatment of diseases such as cancer.

52 Claims, No Drawings

(56) References Cited

FOREIGN PATENT DOCUMENTS

| | | |
|---|---|---|
| WO | WO 2010/144679 | 12/2010 |
| WO | WO 2010/144680 | 12/2010 |
| WO | WO 2011/024987 | 3/2011 |
| WO | WO 2011/054553 | 5/2011 |
| WO | WO 2011/054841 | 5/2011 |
| WO | WO 2011/054843 | 5/2011 |
| WO | WO 2011/054844 | 5/2011 |
| WO | WO 2011/054845 | 5/2011 |
| WO | WO 2011/054846 | 5/2011 |
| WO | WO 2011/054848 | 5/2011 |
| WO | WO 2011/054851 | 5/2011 |
| WO | WO 2011/133722 | 10/2011 |
| WO | WO 2011/143651 | 11/2011 |
| WO | WO 2011/143657 | 11/2011 |
| WO | WO 2011/143660 | 11/2011 |
| WO | WO 2011/143669 | 11/2011 |
| WO | WO 2011/161031 | 12/2011 |
| WO | WO 2012/075383 | 6/2012 |
| WO | WO 2012/075456 | 6/2012 |
| WO | WO 2012/116170 | 8/2012 |
| WO | WO 2012/143413 | 10/2012 |
| WO | WO 2012/143415 | 10/2012 |
| WO | WO 2012/143416 | 10/2012 |
| WO | WO 2012/150234 | 11/2012 |
| WO | WO 2012/151512 | 11/2012 |
| WO | WO 2012/174487 | 12/2012 |
| WO | WO 2012/178208 | 12/2012 |
| WO | WO 2013/019710 | 2/2013 |
| WO | WO 2013/024104 | 2/2013 |
| WO | WO 2013/027168 | 2/2013 |
| WO | WO 2013/029548 | 3/2013 |
| WO | WO 2013/030150 | 3/2013 |
| WO | WO 2013/033268 | 3/2013 |
| WO | WO 2013/033269 | 3/2013 |
| WO | WO 2013/033270 | 3/2013 |
| WO | WO 2013/043553 | 3/2013 |
| WO | WO 2013/044511 | 4/2013 |
| WO | WO 2013/064900 | 5/2013 |
| WO | WO 2013/097052 | 7/2013 |
| WO | WO 2013/097601 | 7/2013 |
| WO | WO 2013/148197 | 10/2013 |
| WO | WO 2013/155695 | 10/2013 |
| WO | WO 2013/156869 | 10/2013 |
| WO | WO 2013/158952 | 10/2013 |
| WO | WO 2013/175281 | 11/2013 |
| WO | WO 2013/184876 | 12/2013 |
| WO | WO 2013/184878 | 12/2013 |
| WO | WO 2013/185284 | 12/2013 |
| WO | WO 2013/186612 | 12/2013 |
| WO | WO 2013/188381 | 12/2013 |
| WO | WO 2014/001356 | 1/2014 |
| WO | WO 2014/015175 | 1/2014 |
| WO | WO 2014/026997 | 2/2014 |
| WO | WO 2014/028547 | 2/2014 |
| WO | WO 2014/048945 | 4/2014 |
| WO | WO 2014/068402 | 5/2014 |
| WO | WO 2014/076146 | 5/2014 |
| WO | WO 2014/078257 | 5/2014 |
| WO | WO 2014/080290 | 5/2014 |
| WO | WO 2014/080291 | 5/2014 |
| WO | WO 2014/095774 | 6/2014 |
| WO | WO 2014/095775 | 6/2014 |
| WO | WO 2014/096965 | 6/2014 |
| WO | WO 2014/128655 | 8/2014 |
| WO | WO 2014/134232 | 9/2014 |
| WO | WO 2014/134267 | 9/2014 |
| WO | WO 2014/139324 | 9/2014 |
| WO | WO 2014/140076 | 9/2014 |
| WO | WO 2014/140077 | 9/2014 |
| WO | WO 2014/143768 | 9/2014 |
| WO | WO 2014/145051 | 9/2014 |
| WO | WO 2014/152029 | 9/2014 |
| WO | WO 2014/154760 | 10/2014 |
| WO | WO 2014/154762 | 10/2014 |
| WO | WO 2014/159392 | 10/2014 |
| WO | WO 2014/159837 | 10/2014 |
| WO | WO 2014/160873 | 10/2014 |
| WO | WO 2014/164596 | 10/2014 |
| WO | WO 2014/164771 | 10/2014 |
| WO | WO 2014/164780 | 10/2014 |
| WO | WO 2014/165127 | 10/2014 |
| WO | WO 2014/165143 | 10/2014 |
| WO | WO 2014/170350 | 10/2014 |
| WO | WO 2014/173241 | 10/2014 |
| WO | WO 2014/182929 | 11/2014 |
| WO | WO 2014/191894 | 12/2014 |
| WO | WO 2014/191896 | 12/2014 |
| WO | WO 2014/191906 | 12/2014 |
| WO | WO 2014/191911 | 12/2014 |
| WO | WO 2014/202578 | 12/2014 |
| WO | WO 2014/206150 | 12/2014 |
| WO | WO 2014/206345 | 12/2014 |
| WO | WO 2014/210425 | 12/2014 |
| WO | WO 2015/002754 | 1/2015 |
| WO | WO 2015/004533 | 1/2015 |
| WO | WO 2015/004534 | 1/2015 |
| WO | WO 2015/006193 | 1/2015 |
| WO | WO 2015/013635 | 1/2015 |
| WO | WO 2015/081203 | 6/2015 |
| WO | WO 2015/164480 | 10/2015 |
| WO | WO 2015/168555 | 11/2015 |
| WO | WO 2015/168621 | 11/2015 |
| WO | WO 2015/169951 | 11/2015 |
| WO | WO 2015/169953 | 11/2015 |
| WO | WO 2015/184257 | 12/2015 |
| WO | WO 2016/044130 | 3/2016 |
| WO | WO 2016/186453 | 11/2016 |

OTHER PUBLICATIONS

Belkina et al., "BET Protein Function is Required for Inflammation: Brd2 Genetic Disruption and BET Inhibitor JQ1 Impair Mouse Macrophage Inflammatory Responses," J Immunol., 2013, 190:3670-3678.
Berge et al., "Pharmaceutical Salts," J Pharm. Sci., 1977, 66(1):1-19.
Blom et al., "Optimizing Preparative LC-MS Configurations and Methods for Parallel Synthesis Purification," J Comb Chem., 2003, 5(5):670-683.
Blom et al., "Preparative LCMS Purification: Improved Compound Specific Method Optimization," J Comb Chem., 2004, 6(6):874-883.
Blom, "Two-pump at-column-dilution configuration for preparative liquid chromatography-mass spectrometry," J Comb Chem., 2002, 4(4):295-301.
Byrn et al., "Pharmaceutical Solids: A Strategic Approach to Regulatory Considerations," Pharmaceutical Research, Jul. 1995, 12(7):945-954.
Cheng et al., "Inhibition of BET Bromodomain Targets Genetically Diverse Glioblastoma," Clin Cancer Res 19:1748-1759, Feb. 2013.
Chiang, "Brd4 engagement from chromatin targeting to transcriptional regulation: selective contact with acetylated histone H3 and H4," Biology Reports, Dec. 2009, 1:98, 7 pages.
Chinese Office Action in Chinese Application No. 201480025137, dated May 17, 2016, 14 pages (English Translation).
Chinese Office Action in Chinese Application No. 201480025137, dated Feb. 16, 2017, 21 pages (w/ English Translation).
Chung et al., "Discovery and Characterization of Small Molecule Inhibitors of the BET Family Bromodomains," J Med Chem., 2011, 54:3827-3838.
Chung et al., "Fragment-Based Discovery of Bromodomain Inhibitors Part 1: Inhibitor Binding Modes and Implications for Lead Discovery," J Med Chem., 2011, 11 pages.
Chung et al., "Fragment-based discovery of bromodomain inhibitors part 1: inhibitor binding modes and implications for lead discovery," Supporting Information, 2011, 6 pages.
Dawson et al., "Inhibition of BET recruitment to chromatin as an effective treatment for MLL-fusion leukaemia," Nature, 2011, 5 pages.

(56) References Cited

OTHER PUBLICATIONS

Dawson, "Supplementary Information: Inhibition of BET recruitment to chromatin as an effective treatment for MLL-fusion leukaemia," Nature, 2011, 50 pages.
Delmore et al., "BET bromodomain inhibition as a therapeutic strategy to target c-Myc," Cell, 2011, 146(6):904-917, Supplemental Information: S1-S11.
Delmore et al., "BET bromodomain inhibition as a therapeutic strategy to target c-Myc," Cell, Sep. 2011, 146(6):904-917.
Devaiah et al., "BRD4 is an atypical kinase that phosphorylates serine2 of the RNA polymerase II carboxy-terminal domain," Proc. Nat. Acad. Sci. USA., 2012, 109(18):6927-6932.
Dorwald, F. Zaragoza. Side Reactions in Organic Synthesis: A Guide to Successful Synthesis Design, Weinheim: WILEY-VCH Verlag GmbH & Co. KGaA, 2005, Preface.
Draker et al., "A Combination of H2A.Z and H4 Acetylation Recruits Brd2 to Chromatin during Transcriptional Activation," PLoS Genet., Nov. 2012, 8(11):e1003047, 17 pages.
Filippakopoulos and Knapp, "Targeting bromodomains: epigenetic readers of lysine acetylation," Nature Rev Drug Disc., May 2014, 13:337-356.
Filippakopoulos et al., "Benzodiazepines and benzotriazepines as protein interaction inhibitors targeting bromodomains of the BET family," Bioorg Med Chem., 2011, 9 pages.
Filippakopoulos et al., "Histone Recognition and Large-Scale Structural Analysis of the Human Bromodomain Family," Cell, Mar. 2012, 149:214-231.
Filippakopoulos et al., "Selective inhibition of BET bromodomains," Nature, 2010, 468:1067-1073.
Filippakopoulos et al., "Supplemental Information: Selective inhibition of BET bromodomains," Nature, 2010, 468:1067-1073.
Floyd et al., "Supplemental Information: The bromodomain protein Brd4 insulates chromatin from DNA damage signalling," Nature, 2013, 14 pages.
Floyd et al., "The bromodomain protein Brd4 insulates chromatin from DNA damage signalling," Nature, 2013, 498:246-250.
French et al., "BRD4-NUT fusion oncogene: a novel mechanism in aggressive carcinoma," Cancer Res., 2003, 63(2):304-307.
French et al., "BRD-NUT oncoproteins: a family of closely related nuclear proteins that block epithelial differentiation and maintain the growth of carcinoma cells," Oncogene, 2008, 27:2237-2242.
French et al., "Midline carcinoma of children and young adults with NUT rearrangement," J Clin. Oneal., 2004, 22(20):4135-4139.
French, "Demystified molecular pathology of NUT midline carcinomas," J Clin Pathol., 2010, 63:492-496.
French, "NUT midline carcinoma," Cancer Genet Cytogenetics, 2010, 203:16-20.
Frizzo et al., "Structural and thermodynamic properties of new pyrazolo [3,4-d] pyridazinones," Thermochimica Acta., Oct. 2013, 574:63-72.
Gallenkamp et al., "Bromodomains and their Pharmacological Inhibitors," Chem Med Chem., Mar. 2014, 9(3):438-464.
Garnier et al., "BET bromodoma in inhibitors: a patent review," Exp Opin Therapeutic Patents, Feb. 2014, 24(2):185-199.
Greenwald et al., "Eµ-BRD2 transgenic mice develop B-cell lymphoma and leukemia," Blood 103(4):1475-1484, Feb. 2004.
Hackam et al., JAMA, 296(14), 2006, 1731-1732.
Hewings et al., "3,5-Dimethylisoxazoles Act As Acetyl-lysine-mimetic Bromodomain Ligands," J Med Chem., 2011, 54:6761-6770.
Hewings et al., "Progress in the Development and Applciation of Small Molecule Inhibitors of Bromodomain-Acetyl-lysine Interactions," J Med Chem., Nov. 2012, 104 pages (Author Manuscript).
Hewings et al., "Progress in the Development and Applciation of Small Molecule Inhibitors of Bromodomain-Acetyl-lysine Interactions," J Med Chem., Nov. 2012, 55(22):9393-9413.
Houzelstein et al., "Growth and Early Postimplantation Defects in Mice Deficient for the Bromodomain-Containing Protein Brd4," Mole Cell Biol., Jun. 2002, 22(11):3794-3802.
Huang et al., "Brd4 coactivates transcriptional activation of NF-κB via specific binding to acetylated RelA," Mol. Cell Biol., 2009, 29(5):1375-1387.
International Preliminary Report on Patentability in International Application No. PCT/US2014/045543, dated Jan. 21, 2016, 7 pages.
International Preliminary Report on Patentability in International Application No. PCT/US2014/027872, dated Sep. 24, 2015, 8 pages.
International Preliminary Report on Patentability in International Application No. PCT/US2014/067691, dated May 31, 2016, 7 pages.
International Preliminary Report on Patentability in International Application No. PCT/US2014/067629, dated May 31, 2016, 7 pages.
International Preliminary Report on Patentability in International Application No. PCT/US2014/067598, dated May 31, 2016, 7 pages.
International Preliminary Report on Patentability in International Application No. PCT/US2014/071102, dated Jun. 21, 2016, 7 pages.
International Preliminary Report on Patentability in International Application No. PCT/US2015/027047, dated Oct. 25, 2016, 10 pages.
International Search Report and Written Opinion in International Application No. PCT/US2014/027872, mailed Jun. 30, 2014, 12 pages.
International Search Report and Written Opinion in International Application No. PCT/US2014/045543, mailed Sep. 10, 2014, 11 pages.
International Search Report and Written Opinion in International Application No. PCT/US2014/067598, mailed Feb. 13, 2015, 9 pages.
International Search Report and Written Opinion in International Application No. PCT/US2014/067629, mailed Feb. 16, 2015, 11 pages.
International Search Report and Written Opinion in International Application No. PCT/US2014/067691, mailed Feb. 2, 2015, 10 pages.
International Search Report and Written Opinion in International Application No. PCT/US2014/071102, mailed Feb. 13, 2015, 9 pages.
International Search Report and Written Opinion in International Application No. PCT/US2015/027047, dated Jul. 10, 2015, 14 pages.
International Search Report and Written Opinion in International Application No. PCT/US2015/049909, dated Dec. 7, 2015, 13 pages.
International Search Report and Written Opinion in International Application No. PCT/US2016/059360, dated Feb. 13, 2017, 20 pages.
Jang et al., "The bromodomain protein Brd4 is a positive regulator), component of P-TEFb and stimulates RNA polymerase II-dependent transcription," Mol. Cell, Aug. 2005, 19(4):523-534.
Japanese Office Action in Japanese Application No. 2016-502650, dated Jan. 10, 2017, 3 pages (English translation only).
Jin et al., "c-Myb binds MLL through menin in human leukemia cells and is an important driver of MLL-associated leukemogenesis," J Clinc Invest., 2010, 120(2):593-606.
Jordan, V.C. Nature Reviews: Drug Discovery, 2, 2003, 205.
Jung et al., "Affinity Map of BRD4 Interactions with the Histone H4 Tail and the Small Molecule Inhibitor JQ1," J Biol Chem., 2014, 28 pages.
Lamonica et al., "Bromodomain protein Brd3 associates with acetylated GATA1 to promote its chromatin occupancy at erythroid target genes," Proc. Nat. Acad. Sci., USA, 2011, 108(22):E159-168.
Leroy et al., "The double bromodomain proteins Brd2 and Brd3 couple histone acetylation to transcription," Mol. Cell, Apr. 2008, 30(1):51-60.
Lockwood et al., "Sensitivity of human lung adenocarcinoma cell lines to targeted inhibition of BET epigenetic signaling proteins," PNAS Early Edition, 2012, 14 pages.

(56) References Cited

OTHER PUBLICATIONS

Martin et al., "Cyclin-Dependent Kinase Inhibitor Dinaciclib Interacts with the Acetyl-Lysine Recognition Site of Bromodomains," ACS Chem Biol., 2013, 8:2360-2365.
Maruyama et al., "A Mammalian Bromodomain Protein, Brd4, Interacts with Replication Factor C and Inhibits Progression to S Phase," Mol Cell Biol., 2002, 22(18):6509-6520.
Matzuk et al., "Small-Molecule Inhibition of BRDT for Male Contraception," Cell, Aug. 2012, 150:673-684.
McLure et al., "RVX-208, an Inducer of ApoA-I in Humans, Is a BET Bromodomain Antagonist," PLOS ONE, Dec. 2013, 8(12):e83190, 12 pages.
Mertz et al., "Targeting MYC dependence in cancer by inhibiting BET bromodomains," PNAS, 2011, 108(40):16669-16674.
Mirguet et al., "From ApoA1 upregulation to BET family bromodomain inhibition: Discovery of I-BET151," Bioorg Med Chem Lett., 2012, 22:2963-2967.
Mochizuki et al., "The bromodomain protein Brd4 stimulates G1 gene transcription and promotes progression to S phase," J Biol. Chem. 2008, 283(14):9040-9048.
Moriniere et al., "Cooperative binding of two acetylation marks on a histone tail by a single ri bromodomain," Nature, 2009, 461:664-669.
Muller et al., "Bromodomains as therapeutic targets," Expert Reviews, 2011, 13:e29, 21 pages.
Nicodeme et al., "Supplementary Information: Suppression of inflammation by a synthetic histone mimic," Nature, 2010, 40 pages.
Nicodeme et al., "Suppression of inflammation by a synthetic histone mimic," Nature, 2010, 468:1119-1123.
Nishiyama et al., "Brd4 Is Required for Recovery from Antimicrotubule Drug-induced Mitotic Arrest: Preservation of Acetylated Chromatin," Mol Biol Cell, Feb. 2006, 17:814-823.
Ott et al., "BET bromodomain inhibition targets both c-MYC and IL7R in high-risk acute lymphoblastic leukemia," Blood, published online 2012, 29 pages.
Peturssion et al., "Protecting Groups in Carbohydrate Chemistry," J Chem. Educ., 1997, 74(11):1297-1303.
Picaud et al., "RVX-208, an inhibitor of BET transcriptional regulators with selectivity for the second bromodomain," PNAS Early Edition, 2013, 6 pages.
Picaud et al., "Supplemental Information: RVX-208, an inhibitor of BET transcriptional regulators with selectivity for the second bromodomain," PNAS Early Edition, 2013, 9 pages.
Prinjhas et al., "Place your BETs: the therapeutic potential of bromodomains," Trends Pharmacol Sci., 2012, 33(3):146-153.
Puissant et al., "Targeting MYCN in Neuroblastoma by BET Bromodomain Inhibition," Cancer Discovery, 16 pages, Mar. 2013.
Rahman et al., "The Brd4 Extraterminal Domain Confers Transcription Activation Independent of pTEFb by Recruiting Multiple Proteins, Including NSD3," Mol Cell Biol., Jul. 2011, 31(13):2641-2652.
Ravin, "Preformulation," Remington's Pharmaceutical Sciences, 17th Ed., (Mack Publishing Company, Easton, 1985), pp. 1409-1423.
Sanchez and Zhou, "The role of human bromodomains in chromatin biology and gene transcription," Curr Opin Drug Discov Devel., Sep. 2009, 12(5):659-665 (Author Manuscript).
Schroder et al., "Two-pronged Binding with Bromodomain-containing Protein 4 Liberates Positive Transcription Elongation Factor b from Inactive Ribonucleoprotein Complexes," J Biol Chem., Jan. 6, 2012, 287(2):1000-1009.
Schwartz et al., "Differentiation of NUT Midline Carcinoma by Epigenomic Reprogramming," Cancer Res., 2011, 71:2686-2696.
Seal et al., "Identification of a novel series of BET family bromodomain inhibitors: Binding mode and profile of I-BET151 (GSK1210151A)," Bioorg Med Chem., 2012, 22:2968-2972.
Segura et al., "BRD4 Sustains Melanoma Proliferation and Represents a New Target for Epigenetic Therapy," Cancer Res 73:6264-6276, Aug. 2013.
Shimamura et al., "Efficacy of BET Bromodomain Inhibition in Kras-Mutant Non-Small Cell Lung Cancer," Clin Cancer Res, 10 pages, 2013.
Smith et al., "Genome-wide siRNA screen identifies SMCX, EP400, and Brd4 as E2-dependent regulators of human papillomavirus oncogene expression," PNAS, Feb. 23, 2010, 107(8):3752-3757.
Stenman et al., "New tricks from an old oncogene: Gene fusion and copy No. alterations of MYB in human cancer," Cell Cyle, Aug. 2010, 9(15):2986-2955.
Vidler et al., "Druggability Analysis and Structural Classification of Bromodomain Acetyl-lysine Binding Sites," J Med Chem., 2012, 14 pages.
Wang et al., "Brd2 disruption in mice causes severe obesity without Type 2 diabetes," Biochem. J., 2010, 425(1):71-83.
Wang et al., "The Bromodomain Protein Brd4 Associated with Acetylated Chromatin is Important for Maintenance of Higher-Order Chromatin Structure," JBC, 2012, 22 pages.
Weidner-Glunde et al., "WHAT do viruses BET on?" Frontiers Biosci., Jan. 2010, 15:537-549.
Wu and Chiang et al., "The Double Bromodomaincontaining Chromatin Adaptor Brd4 and Transcriptional Regulation," J Biol Chem., May 2007, 282(18):13141-13145.
Wu et al., "Brd4 links chromatin targeting to HPV transcriptional silencing," Genes Dev., 2006, 20:2383-2396.
Wyce et al., "Inhibition of BET bromodomain proteins as a therapeutic approach in prostate cancer," Oncotarget, 13 pages, Nov. 2013.
Yan et al., "Perturbation of BRD4 Protein Function by BRD4-NUT Protein Abrogates Cellular Differentiation in NUT Midline Carcinoma," J Biol Chem., Aug. 2011, 286(31):27663-27675.
Yan et al., "Supplemental Data: Perturbation of BRD4 Protein Function by BRD4-NUT Protein Abrogates Cellular Differentiation in NUT Midline Carcinoma," J Biol Chem., Aug. 2011, 12 pages.
Yang et al., "Brd4 Recruits P-TEFb to Chromosomes at Late Mitosis to Promote G1 Gene Expression and Cell Cycle Progression," Mol Cell Biol., Feb. 2008, 28(3):967-976.
You et al., "Interaction of the bovine papillomavims E2 protein with Brd4 tethers the viral DNA to host mitotic chromosomes," Cell, 2004, 117(3):349-60.
You et al., "Regulation of Aurora B Expression by the Bromodomain Protein Brd4," Mol Cell Biol., Sep. 2009, 29(18):5094-5103.
Zhang et al., "Bromodomain-Containing-Protein 4 (BRD4) Regulates RNA Polymerase II Serine 2 Phosphorylation in Human CD4+ T Cells," JBC, 2012, 30 pages.
Zhu et al., "Reactivation of latent HIV-1 by inhibition of BRD4," Cell Reports, 2012, 2(4):807-816.
Zuber et al., "An integrated approach to dissecting oncogene addiction implicates a Myb-coordinated self-renewal program as essential for leukemia maintenance," Genes Dev., 2011, 25:1628-1640.
Zuber et al., "RNAi screen identifies Brd4 as a therapeutic target in acute myeloid leukaemia," Nature, 2011, 478(7370):524-528.
Zuber et al., "Supplemental Information: RNAi screen identifies Brd4 as a therapeutic target in acute myeloid leukaemia," Nature, 2011, 33 pages.

BICYCLIC HETEROCYCLES AS BET PROTEIN INHIBITORS

CLAIM OF PRIORITY

This application is a continuation of U.S. patent application Ser. No. 14/554,263, filed on Nov. 26, 2014, which claims priority under 35 USC §119(e) to U.S. Patent Application Ser. No. 61/908,954, filed on Nov. 26, 2013, the entire contents of which are hereby incorporated by reference.

TECHNICAL FIELD

The present invention relates to bicyclic heterocycles which are inhibitors of BET proteins such as BRD2, BRD3, BRD4, and BRD-t and are useful in the treatment of diseases such as cancer.

BACKGROUND

The genomes of eukaryotic organisms are highly organized within the nucleus of the cell. DNA is packaged into chromatin by wrapping around a core of histone proteins to form a nucleosome. These nucleosomes are further compacted by aggregation and folding to form a highly condensed chromatin structure. A range of different states of condensation are possible, and the tightness of this structure varies during the cell cycle, being most compact during the process of cell division. Chromatin structure plays a critical role in regulating gene transcription by regulating protein access to the DNA. The chromatin structure is controlled by a series of post translational modifications to histone proteins, mainly within the tails of histones H3 and H4 that extend beyond the core nucleosome structure. These reversible modifications include acetylation, methylation, phosphorylation, ubiquitination and SUMOylation. These epigenetic marks are written and erased by specific enzymes that modify specific residues within the histone tail, thereby forming an epigenetic code. Other nuclear proteins bind to these marks and effect outputs specified by this information through the regulation of chromatin structure and gene transcription. Increasing evidence links genetic changes to genes encoding epigenetic modifiers and regulators leading to aberrant histone marks in diseases such as neurodegenerative disorders, metabolic diseases, inflammation and cancer.

Histone acetylation is typically associated with the activation of gene transcription, as the modification weakens the interaction between the DNA and the histone proteins, permitting greater access to DNA by the transcriptional machinery. Specific proteins bind to acetylated lysine residues within histones to "read" the epigenetic code. A highly conserved protein module called the bromodomain binds to acetylated lysine residues on histone and other proteins. There are more than 60 bromodomain-containing proteins in the human genome.

The BET (Bromodomain and Extra-Terminal) family of bromodomain containing proteins comprises 4 proteins (BRD2, BRD3, BRD4 and BRD-t) that share a conserved structural organization containing tandem N-terminal bromodomains capable of binding to acetylated lysine residues of histones and other proteins. BRD2, BRD3 and BRD4 are ubiquitiously expressed while BRDt is restricted to germ cells. BRD proteins play essential, but non-overlapping roles in regulating gene transcription and controlling cell growth. BET proteins are associated with large protein complexes including Mediator, PAFc and super elongation complex that regulate many aspects of gene transcription. BRD2 and BRD4 proteins have been shown to remain in complex with chromosomes during mitosis and are required to promote transcription of critical genes including cyclin D and c-Myc that initiate the cell cycle (Mochizuki J Biol. Chem. 2008 283:9040-9048). BRD4 is essential for recruiting the protein translational elongation factor B complex to the promoters of inducible genes resulting in the phosphorylation of RNA polymerase II and stimulating productive gene transcription and elongation (Jang et al. Mol. Cell 2005 19:523-534). In some instances, a kinase activity of BRD4 may directly phosphorylate and activate RNA polymerase II (Devaiah et al. PNAS 2012 109:6927-6932). Cells lacking BRD4 show impaired progression through cell cycle. BRD2 and BRD3 are reported to associate with histones along actively transcribed genes and may be involved in facilitating transcriptional elongation (Leroy et al, Mol. Cell. 2008 30:51-60). In addition to acetylated histones, BET proteins have been shown to bind selectively to acetylated transcription factors including the RelA subunit of NF-kB and GATA1 thereby directly regulating the transcriptional activity of these proteins to control expression of genes involved in inflammation and hematopoietic differentiation (Huang et al, Mol. Cell. Biol. 2009 29:1375-1387; Lamonica Proc. Nat. Acad. Sci. 2011 108:E159-168).

A recurrent translocation involving NUT (nuclear protein in testes) with BRD3 or BRD4 to form a novel fusion oncogene, BRD-NUT, is found in a highly malignant form of epithelial neoplasia (French et al, Cancer Research 2003 63:304-307; French et al, Journal of Clinical Oncology 2004 22:4135-4139). Selective ablation of this oncogene restores normal cellular differentiation and reverses the tumorigenic phenotype (Filippakopoulos et al, Nature 2010 468:1068-1073). Genetic knockdown of BRD2, BRD3 and BRD4 has been shown to impair the growth and viability of a wide range of hematological and solid tumor cells (Zuber et al, Nature 2011 478:524-528; Delmore et al, Cell 2011 146: 904-917). Aside from a role in cancer, BET proteins regulate inflammatory responses to bacterial challenge, and a BRD2 hypomorph mouse model showed dramatically lower levels of inflammatory cytokines and protection from obesity induced diabetes (Wang et al Biochem J. 2009 425:71-83; Belkina et al. J. Immunol 2013). In addition, some viruses make use of these BET proteins to tether their genomes to the host cell chromatin, as part of the process of viral replication or use BET proteins to facilitate viral gene transcription and repression (You et al, Cell 2004 117:349-60; Zhu et al, Cell Reports 2012 2:807-816).

Accordingly, there is a need for compounds that modulate the activity of the BET family of proteins, including BRD2, BRD3, and BRD4, that can be used to treat BET protein-associated diseases such as cancer. The compounds of the invention help meet this need.

SUMMARY

The present invention provides, inter alia, a compound of Formula I:

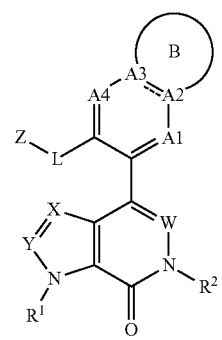

or a pharmaceutically acceptable salt thereof; wherein the variables are as defined below.

The present invention also provides a pharmaceutical composition comprising a compound of Formula I, or a pharmaceutically acceptable salt thereof, and at least one pharmaceutically acceptable carrier.

The present invention also provides a method of inhibiting a BET protein comprising contacting a compound of Formula I, or a pharmaceutically acceptable salt thereof, with the BET protein.

The present invention also provides a method of treating cancer and other diseases comprising administering to a patient a therapeutically effective amount of a compound of Formula I, or a pharmaceutically acceptable salt thereof.

The present invention also provides a compound of Formula I, or a pharmaceutically acceptable salt thereof, for use in therapy.

The present invention also provides use of a compound of Formula I, or a pharmaceutically acceptable salt thereof, in the preparation of a medicament for use in therapy.

DETAILED DESCRIPTION

The present invention provides, inter alia, a compound of Formula I:

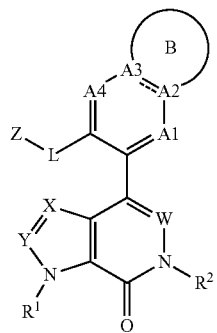

or a pharmaceutically acceptable salt thereof, wherein:
≡≡≡≡≡≡ represents a single or double bond;
Ring B is phenyl, 5-membered heteroaryl, 6-membered heteroaryl, $C_5$-cycloalkyl, $C_6$-cycloalkyl, 5-membered heterocycloalkyl, or 6-membered heterocycloalkyl, each optionally substituted by 1, 2, 3, or 4 $R^B$;
L is absent, —$(CR^aR^b)_p$—, —$(CR^aR^b)_n$—O—$(CR^aR^b)_m$—, —$(CR^aR^b)_n$—S—$(CR^aR^b)_m$—, —$(CR^aR^b)_n$—S(=O)—$(CR^aR^b)_m$—, —$(CR^aR^b)_n$—S(=O)$_2$—$(CR^aR^b)_m$—, —$(CR^aR^b)_n$—C(=O)—$(CR^aR^b)_m$—, —$(CR^aR^b)_n$—C(=O)O—$(CR^aR^b)_m$—, —$(CR^aR^b)_n$—OC(=O)—$(CR^aR^b)_m$—, —$(CR^aR^b)_n$—NR$^c$—$(CR^aR^b)_m$—, —$(CR^aR^b)_n$—C(=O)NR—$(CR^aR^b)_m$—, —$(CR^aR^b)_n$—NR$^c$C(=O)—$(CR^aR^b)_m$—, or —$(CR^aR^b)_n$—NR$^c$C(=O)NR$^d$—$(CR^aR^b)_m$—;
A1 is $CR^3$ or N;
A2 is C or N;
A3 is C or N;
A4 is $CR^4$ or N;
wherein when one of A2 and A3 is N, then the other of A2 and A3 is C;
W is $CR^5$ or N;
X is $CR^6$ or N;
Y is $CR^7$ or N;

Z is $C_{6-10}$ aryl, $C_{3-10}$ cycloalkyl, or 5-10 membered heteroaryl, or 4-10 membered heterocycloalkyl, each of which is optionally substituted by 1, 2, 3, 4, or 5 $R^Z$;
$R^1$ is H or $C_{1-4}$ alkyl;
$R^2$ is $C_{1-4}$ alkyl, $C_{1-4}$ haloalkyl, or $C_{1-4}$ hydroxyalkyl;
$R^3$ and $R^4$ are each independently selected from H, halo, CN, $NO_2$, $C_{1-6}$ alkyl, $C_{1-6}$ haloalkyl, $C_{2-6}$ alkenyl, and $C_{2-6}$ alkynyl;
$R^5$ is H, halo, $C_{1-6}$ alkyl, or $C_{1-6}$ haloalkyl;
$R^6$ is H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^7$ is H, $C_{1-6}$ alkyl, $C_{1-6}$ haloalkyl, $C_{2-6}$ alkenyl, $C_{2-6}$ alkynyl, $C(O)R^{b2}$, $C(O)NR^{c2}R^{d2}$, $C(O)OR^{a2}$, $S(O)R^{b2}$, $S(O)NR^{c2}R^{d2}$, $S(O)_2R^{b2}$, or $S(O)_2NR^{c2}R^{d2}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^B$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^Z$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

each R$^a$ and R$^b$ is independently selected from H, halo, OH, methyl, and ethyl;

each R$^c$ and R$^d$ is independently selected from H, $C_{1-4}$ alkyl, $C_{1-4}$ haloalkyl, $C_{1-4}$ hydroxyalkyl, and cyclopropyl;

each R$^{a1}$, R$^{b1}$, R$^{c1}$, R$^{d1}$, R$^{a2}$, R$^{b2}$, R$^{c2}$, R$^{d2}$, R$^{a3}$, R$^{b3}$, R$^{c3}$, R$^{d3}$, R$^{a4}$, R$^{b4}$, R$^{c4}$, and R$^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3}$-$C_{10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl is optionally substituted with 1, 2, 3, 4, or 5 substituents independently selected from $C_{1-4}$ alkyl, $C_{1-4}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$NR$^{c5}$S(O)$_2$NR$^{c5}$R$^{d5}$, and S(O)$_2$NR$^{c5}$R$^{d5}$;

or any R$^{c1}$ and R$^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^{c2}$ and R$^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR$^{a5}$, SR$^{a5}$, C(O)R$^{b5}$, C(O)NR$^{c5}$R$^{d5}$, C(O) OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$NR$^{c5}$S(O)$_2$NR$^{c5}$R$^{d5}$, and S(O)$_2$NR$^{c5}$R$^{d5}$;

or any R$^{c3}$ and R$^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR$^{a5}$, SR$^{a5}$, C(O)R$^{b5}$, C(O)NR$^{c5}$R$^{d5}$, C(O) OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^{c4}$ and R$^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR$^{a5}$, SR$^{a5}$, C(O)R$^{b5}$, C(O)NR$^{c5}$R$^{d5}$, C(O) OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c}$R$^{d5}$, and S(O)$_2$NR$^{c5}$R$^{d5}$;

each R$^{e1}$, R$^{e2}$, R$^{e3}$, and R$^{e4}$ is independently selected from H, $C_{1-4}$ alkyl, CN, OR$^{a5}$, SR$^{b5}$, S(O)$_2$R$^{b5}$, C(O)R$^{b5}$, S(O)$_2$NR$^{c5}$R$^{d5}$, and C(O)NR$^{c5}$R$^{d5}$;

each R$^{a5}$, R$^{b5}$, R$^{c5}$, and R$^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each R$^{e5}$ is independently selected from H, $C_{1-4}$ alkyl, and CN;

n is 0, 1, or 2;

m is 0, 1, or 2; and p is 1, 2, 3, or 4;

wherein any aforementioned heterocycloalkyl group, including the heterocycloalkyl group of Ring B, is optionally substituted by 1 or 2 oxo groups.

The present invention further provides, inter alia, a compound of Formula I:

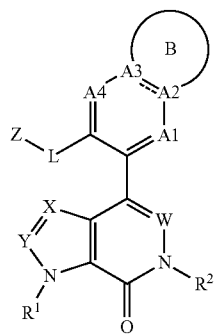

or a pharmaceutically acceptable salt thereof; wherein
------ represents a single or double bond;

Ring B is phenyl, 5-membered heteroaryl, 6-membered heteroaryl, $C_5$-cycloalkyl, $C_6$-cycloalkyl, 5-membered heterocycloalkyl, or 6-membered heterocycloalkyl, each optionally substituted by 1, 2, 3, or 4 $R^B$;

L is absent, $-(CR^aR^b)_p-$, $-(CR^aR^b)_n-O-(CR^aR^b)_m-$, $-(CR^aR^b)_n-S-(CR^aR^b)_m-$, $-(CR^aR^b)_n-S(=O)-(CR^aR^b)_m-$, $-(CR^aR^b)_n-S(=O)_2-(CR^aR^b)_m-$, $-(CR^aR^b)_n-C(=O)-(CR^aR^b)_m-$, $-(CR^aR^b)_n-C(=O)O-(CR^aR^b)_m-$, $-(CR^aR^b)_n-OC(=O)-(CR^aR^b)_m-$, $-(CR^aR^b)_n-NR^c-(CR^aR^b)_m-$, $-(CR^aR^b)_n-C(=O)NR^c-(CR^aR^b)_m-$, $-(CR^aR^b)_n-NR^cC(=O)-(CR^aR^b)_m-$, or $-(CR^aR^b)_n-NR^cC(=O)NR^d-(CR^aR^b)_m-$;

A1 is $CR^3$ or N;
A2 is C or N;
A3 is C or N;
A4 is $CR^4$ or N;
wherein when one of A2 and A3 is N, then the other of A2 and A3 is C;
W is $CR^5$ or N;
X is $CR^6$ or N;
Y is $CR^7$ or N;
Z is $C_{6-10}$ aryl, $C_{3-10}$ cycloalkyl, or 5-10 membered heteroaryl, or 4-10 membered heterocycloalkyl, each of which is optionally substituted by 1, 2, 3, 4, or 5 $R^Z$;
$R^1$ is H or $C_{1-4}$ alkyl;
$R^2$ is $C_{1-4}$ alkyl, $C_{1-4}$ haloalkyl, or $C_{1-4}$ hydroxyalkyl;
$R^3$ and $R^4$ are each independently selected from H, halo, CN, $NO_2$, $C_{1-6}$ alkyl, $C_{1-6}$ haloalkyl, $C_{2-6}$ alkenyl, and $C_{2-6}$ alkynyl;
$R^5$ is H, halo, $C_{1-6}$ alkyl, or $C_{1-6}$ haloalkyl;
$R^6$ is H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^7$ is H, $C_{1-6}$ alkyl, $C_{1-6}$ haloalkyl, $C_{2-6}$ alkenyl, $C_{2-6}$ alkynyl, $C(O)R^{b2}$, $C(O)NR^{c2}R^{d2}$, $C(O)OR^{a2}$, $S(O)R^{b2}$, $S(O)NR^{c2}R^{d2}$, $S(O)_2R^{b2}$, or $S(O)_2NR^{c2}R^{d2}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^B$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^Z$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^a$ and $R^b$ is independently selected from H, halo, OH, methyl, and ethyl;
each $R^c$ and $R^d$ is independently selected from H, $C_{1-4}$ alkyl, $C_{1-4}$ haloalkyl, $C_{1-4}$ hydroxyalkyl, and cyclopropyl;
each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl is optionally substituted with 1, 2, 3, 4, or 5 substituents independently selected from $C_{1-4}$ alkyl, $C_{1-4}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{e1}$, $R^{e2}$, $R^{e3}$, and $R^{e4}$ is independently selected from H, $C_{1-4}$ alkyl, CN, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

each $R^{a5}$, $R^{b5}$, $R^{c5}$, and $R^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e5}$ is independently selected from H, $C_{1-4}$ alkyl, and CN;

n is 0, 1, or 2;

m is 0, 1, or 2; and p is 1, 2, 3, or 4;

wherein any aforementioned heterocycloalkyl group, including the heterocycloalkyl group of Ring B, is optionally substituted by 1 or 2 oxo groups.

When both A2 and A3 are C, then the symbol ------ represents a double bond, and when one of A2 and A3 is N and the other is C, then the symbol ------ represents a single bond.

In some embodiments, $R^1$ is H.

In some embodiments, $R^2$ is $C_{1-4}$ alkyl.

In some embodiments, $R^2$ is methyl.

In some embodiments, W is $CR^5$.

In some embodiments, X is $CR^6$.

In some embodiments, Y is $CR^7$.

In some embodiments, Y is N.

In some embodiments, the bicyclic ring containing W, X, and Y is selected from:

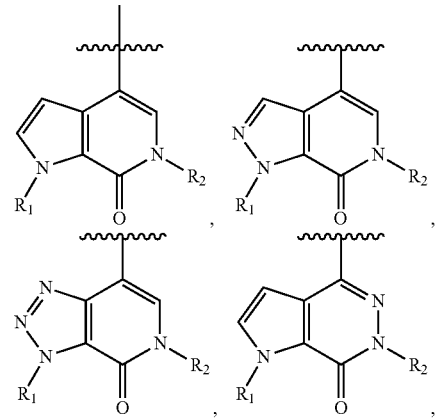

-continued

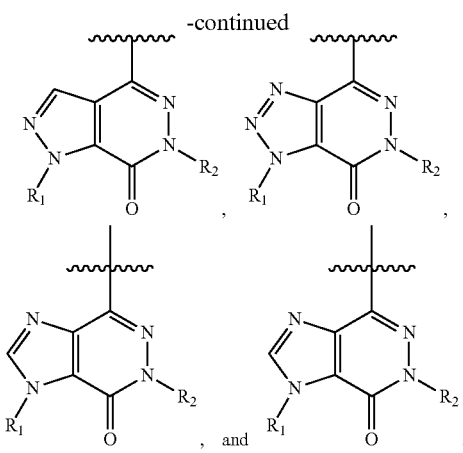
, and

In some embodiments, the bicyclic ring containing W, X, and Y is selected from:

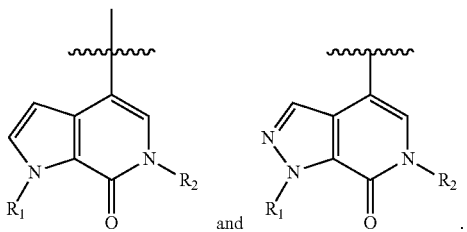
and

In some embodiments, L is —(CR$^a$R$^b$)$_n$—O—(CR$^a$R$^b$)$_m$—.

In some embodiments, L is O or CH$_2$O.

In some embodiments, L is O.

In some embodiments, Z is C$_{6-10}$ aryl, C$_{3-7}$ cycloalkyl, or 5-10 membered heteroaryl, each of which is optionally substituted by 1, 2, 3, 4, or 5 R$^Z$.

In some embodiments, Z is C$_{6-10}$ aryl or 5-10 membered heteroaryl, each of which is optionally substituted by 1, 2, 3, 4, or 5 R$^Z$.

In some embodiments, Z is phenyl optionally substituted by 1, 2, 3, 4, or 5 R$^Z$.

In some embodiments, Z is

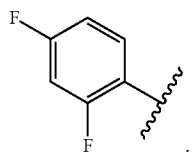

In some embodiments, Z is C$_{3-7}$ cycloalkyl optionally substituted by 1, 2, 3, 4, or 5 R$^Z$.

In some embodiments, Z is cyclobutyl.

In some embodiments, R$^Z$ is independently selected from halo, C$_{1-6}$ alkyl, C$_{2-6}$ alkenyl, C$_{2-6}$ alkynyl, C$_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$.

In some embodiments, R$^Z$ is independently selected from F, Cl, and Br.

In some embodiments, A1 is CR$^3$.
In some embodiments, A2 is C.
In some embodiments, A3 is C.
In some embodiments, A4 is CR$^4$.

In some embodiments, each R$^B$ is independently selected from C$_{1-6}$ alkyl, C$_{6-10}$ aryl, C$_{3-10}$ cycloalkyl, 5-10 membered heteroaryl, 4-10 membered heterocycloalkyl, wherein said C$_{1-6}$ alkyl, C$_{6-10}$ aryl, C$_{3-10}$ cycloalkyl, 5-10 membered heteroaryl, and 4-10 membered heterocycloalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

In some embodiments, each R$^B$ is independently selected from C$_{1-6}$ alkyl, C$_{6-10}$ aryl, C$_{3-10}$ cycloalkyl, and 4-10 membered heterocycloalkyl, wherein said C$_{1-6}$ alkyl is optionally substituted with 1, 2, or 3 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, and C(O)OR$^{a3}$.

In some embodiments, each R$^B$ is independently selected from C$_{1-6}$ alkyl, C$_{3-10}$ cycloalkyl, and 4-10 membered heterocycloalkyl, wherein said C$_{1-6}$ alkyl is optionally substituted with 1 or 2 substituents independently selected from phenyl and C(O)OR$^{a3}$.

In some embodiments, the compounds of the invention have Formula II:

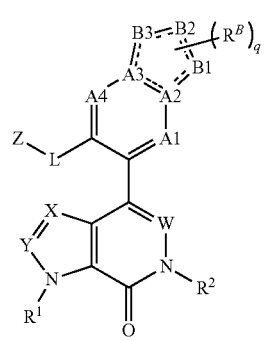

wherein:

the 5-membered ring formed by A2, A3, B1, B2, and B3 is (1) 5-membered heteroaryl wherein B1, B2, and B3 are each independently selected from CH, N, NH, O, and S, (2) C$_5$-cycloalkyl wherein B1, B2, and B3 are each independently selected from CH, CH$_2$, and C(O), or (3) 5-membered heterocycloalkyl wherein B1, B2, and B3 are each independently selected from CH, CH$_2$, C(O), N, NH, O, S, S(O), and S(O)$_2$; and q is 0, 1, 2 or 3.

The floating substituent —(R$^B$)$_q$ depicted in Formula II and other formulae is meant to indicate that there can be q number of R$^B$ groups substituted on any of the B1, B2, and B3 components of the A2, A3, B1, B2, and B3 5-membered ring. For example, when B1 is selected as CH, the hydrogen of the CH can be replaced by R$^B$ when it is substituted.

In some embodiments, B1, B2, and B3 are each independently selected from CH, CH$_2$, C(O), N, and NH.

In some embodiments, B1 is N or NH.

In some embodiments, B1 is NH.

In some embodiments, B2 is N, CH, or C(O).

In some embodiments, B3 is N or NH.

In some embodiments, the compounds of the invention have Formula IIa:

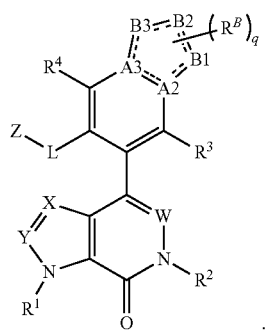

IIa

In some embodiments, the compounds of the invention have Formula IIb:

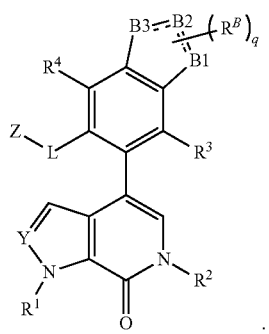

IIb

In some embodiments, the compounds of the invention have Formula IIc:

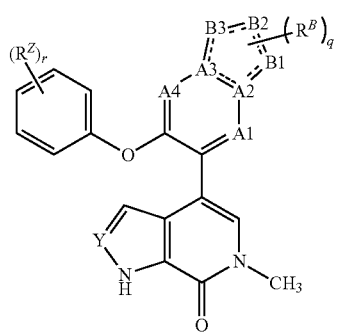

IIc wherein r is 0, 1, 2, 3, 4, or 5.

The floating substituent —(R$^Z$)$_r$ depicted in the phenyl ring of Formula IIc and in other formulae herein is meant to indicate that there can be r number of R$^Z$ groups substituted on the phenyl ring.

In some embodiments, the compounds of the invention have Formula IId, IIe, IIf, or IIg:

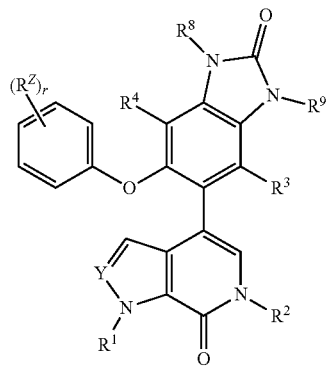

IId

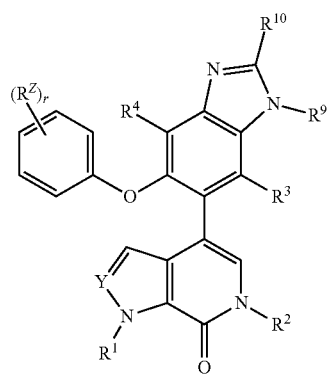

IIe

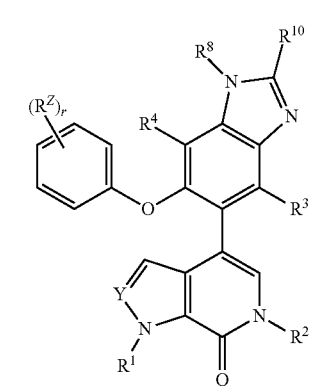

IIf

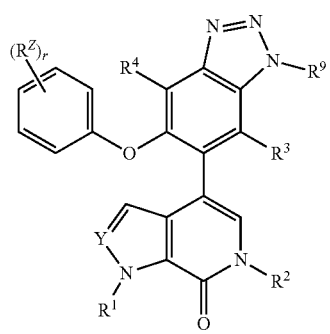

IIg wherein:

r is 0, 1, 2, 3, 4, or 5; and $R^8$, $R^9$, and $R^{10}$ are each independently selected from H, $C_{1-6}$ alkyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, the compounds of the invention have Formula IId, IIe, IIf, or IIg:

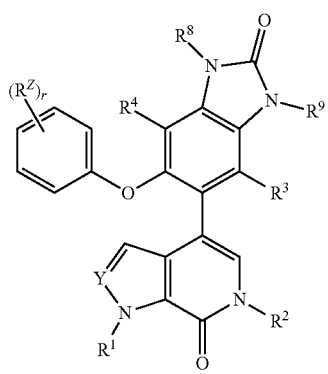

IId

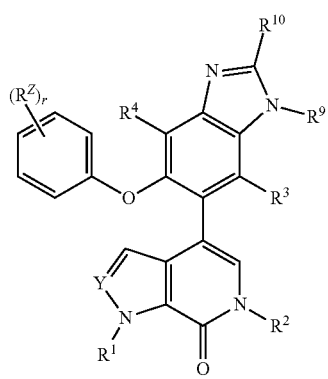

IIe

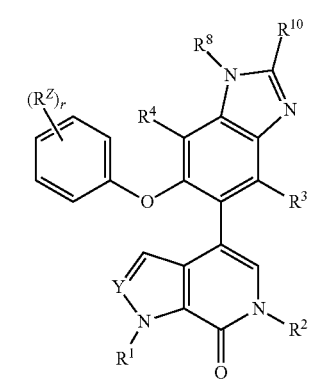

IIf

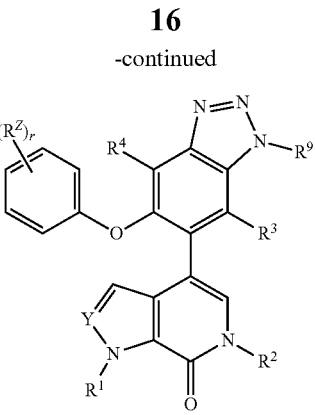

IIg wherein:

r is 0, 1, 2, 3, 4, or 5; and $R^8$, $R^9$, and $R^{10}$ are each independently selected from H, $C_{1-6}$ alkyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, $R^8$, $R^9$, and $R^{10}$ are each independently selected from H, $C_{1-6}$ alkyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, r is 0, 1, 2, or 3.

In some embodiments, the compounds of the invention have Formula IIh:

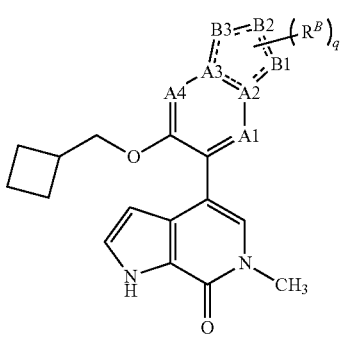

IIh or a pharmaceutically acceptable salt thereof.

In some embodiments, the compounds of the invention have Formula IIi or IIj:

IIi

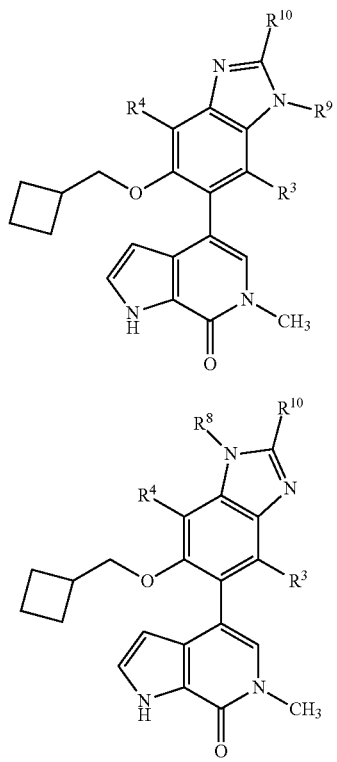

IIj

B5, B6, and B7 are each independently selected from CH and N, (3) $C_6$-cycloalkyl wherein B4, B5, B6, and B7 are each independently selected from CH, $CH_2$, and C(O), or (4) 6-membered heterocycloalkyl wherein B4, B5, B6, and B7 are each independently selected from CH, $CH_2$, C(O), N, NH, O, S, S(O), and $S(O)_2$; and s is 0, 1, 2, 3, or 4.

The floating substituent —$(R^B)_s$ depicted in Formula III and other formulae herein is meant to indicate that there can be s number of $R^B$ groups substituted on any of the B4, B5, B6, and B7 components of the A2, A3, B4, B5, B6, and B7 6-membered ring. For example, when B4 is selected as CH, the hydrogen of the CH can be replaced by $R^B$ when it is substituted.

In some embodiments, the bicyclic moiety containing Ring B has the formula:

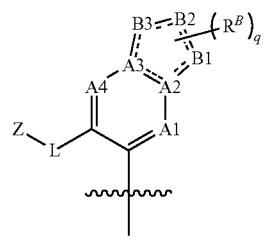

wherein q is 0, 1, 2 or 3.

In some embodiments, the bicyclic moiety containing Ring B has the formula:

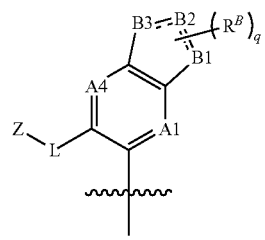

wherein q is 0, 1, 2 or 3.

In some embodiments, the bicyclic moiety containing Ring B has the formula:

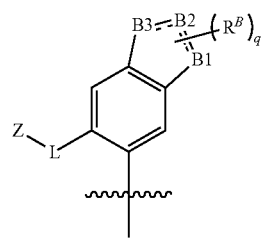

wherein q is 0, 1, 2 or 3.

In some embodiments, the bicyclic moiety containing Ring B has the formula:

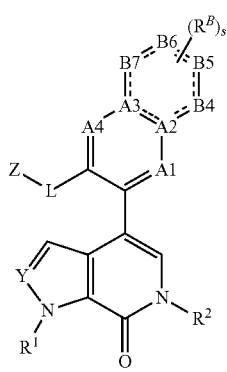

or a pharmaceutically acceptable salt thereof, wherein:

$R^8$, $R^9$, and $R^{10}$ are each independently selected from H, $C_{1-6}$ alkyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{1-6}$ haloalkyl, $C_{6-10}$ aryl, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, the compounds of the invention have Formula III:

III

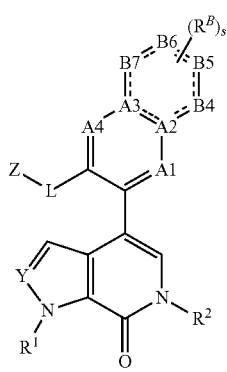

wherein:

the 6-membered ring formed by A2, A3, B4, B5, B6, and B7 is (1) phenyl, (2) 6-membered heteroaryl wherein B4,

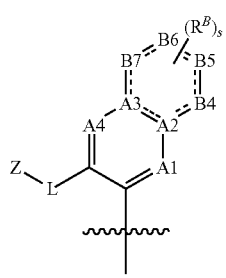
wherein s is 0, 1, 2, 3, or 4.
In some embodiments, the bicyclic moiety containing Ring B has the formula:
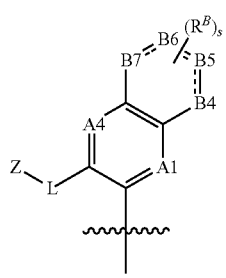
wherein s is 0, 1, 2, 3, or 4.
In some embodiments, the bicyclic moiety containing Ring B has the formula:
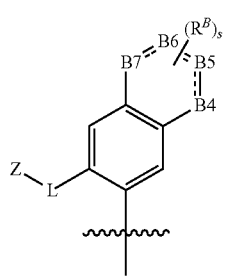
wherein s is 0, 1, 2, 3, or 4.
In some embodiments, the bicyclic moiety containing Ring B is selected from:
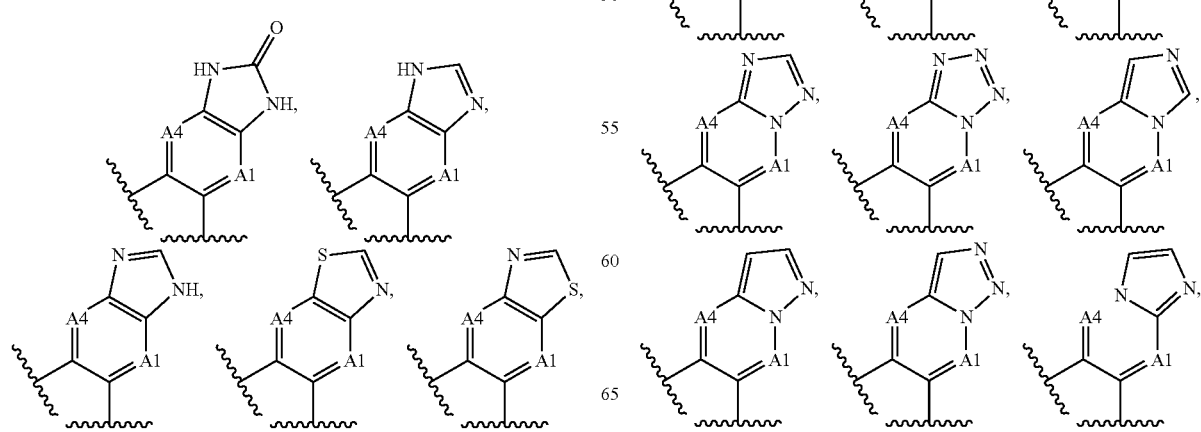
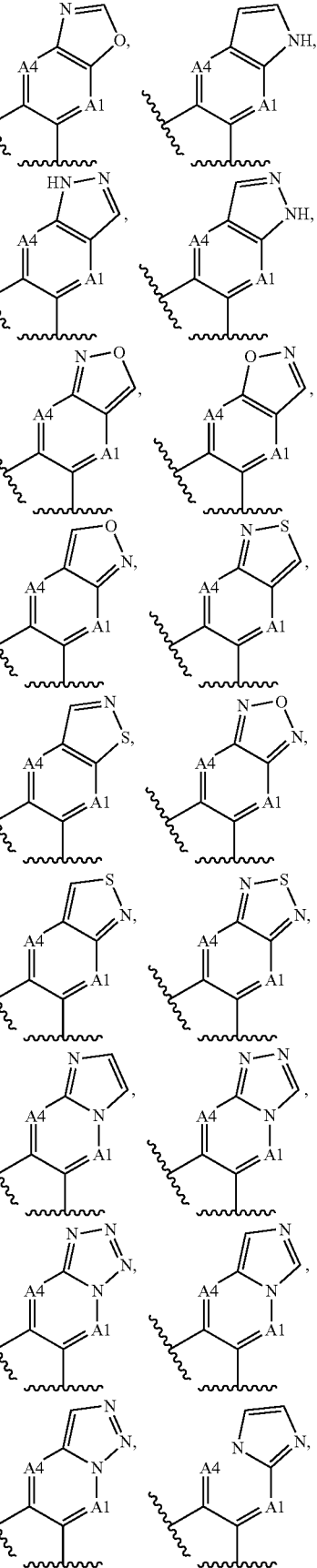

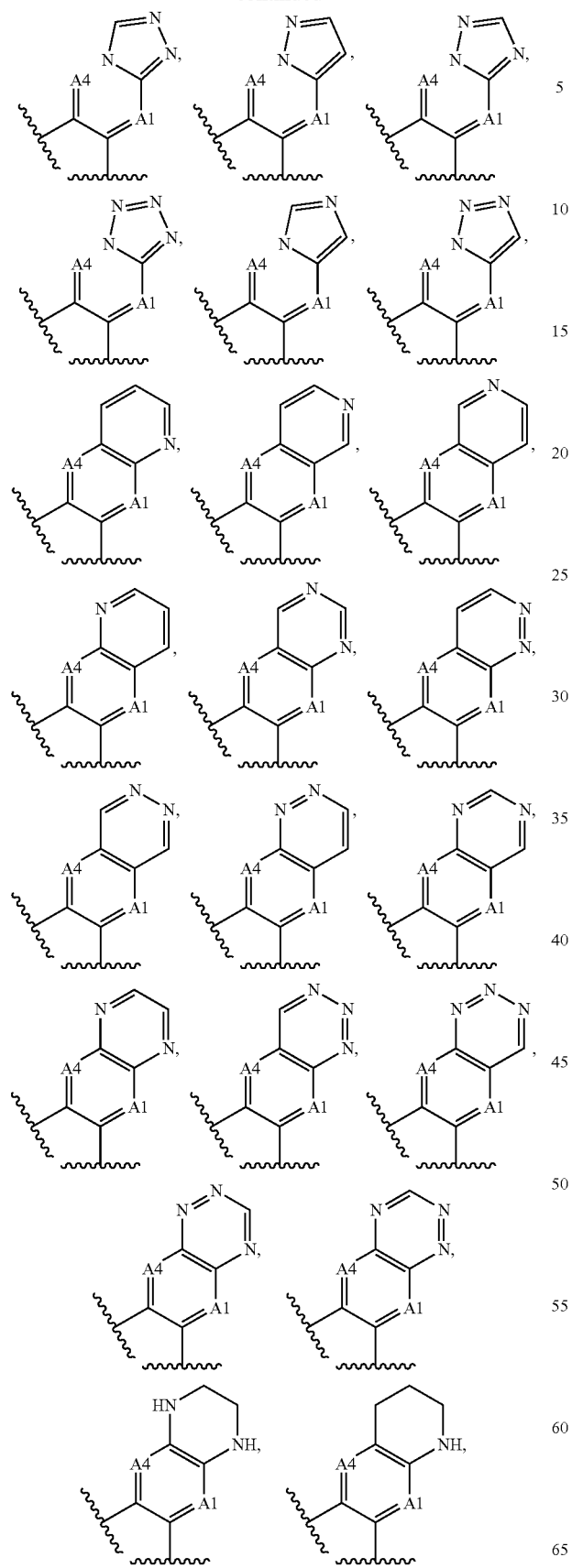
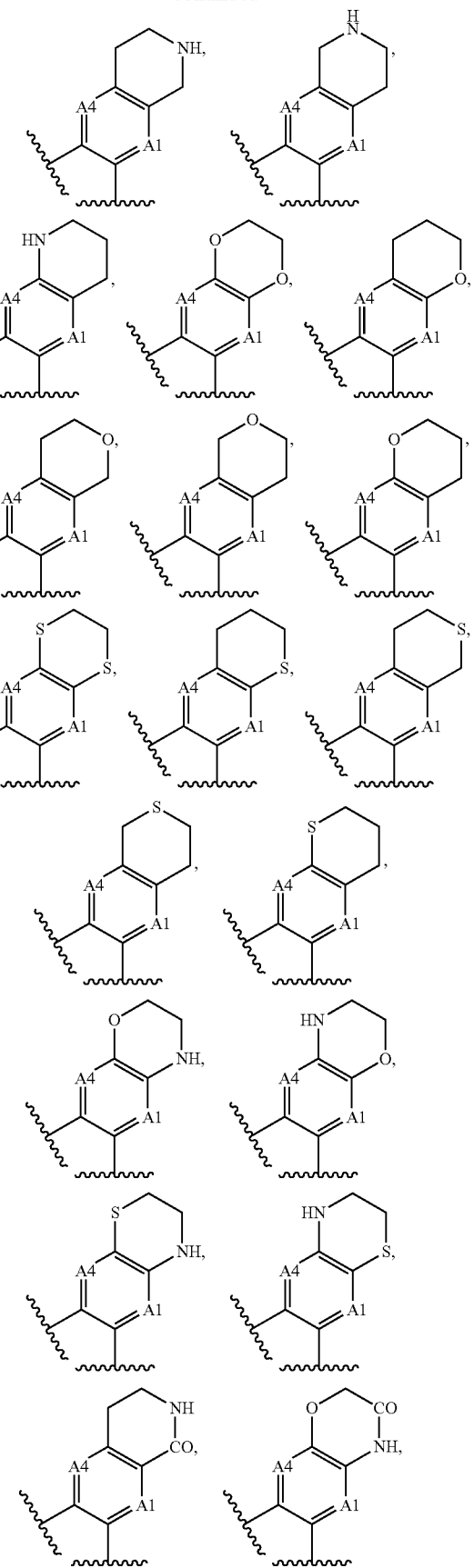

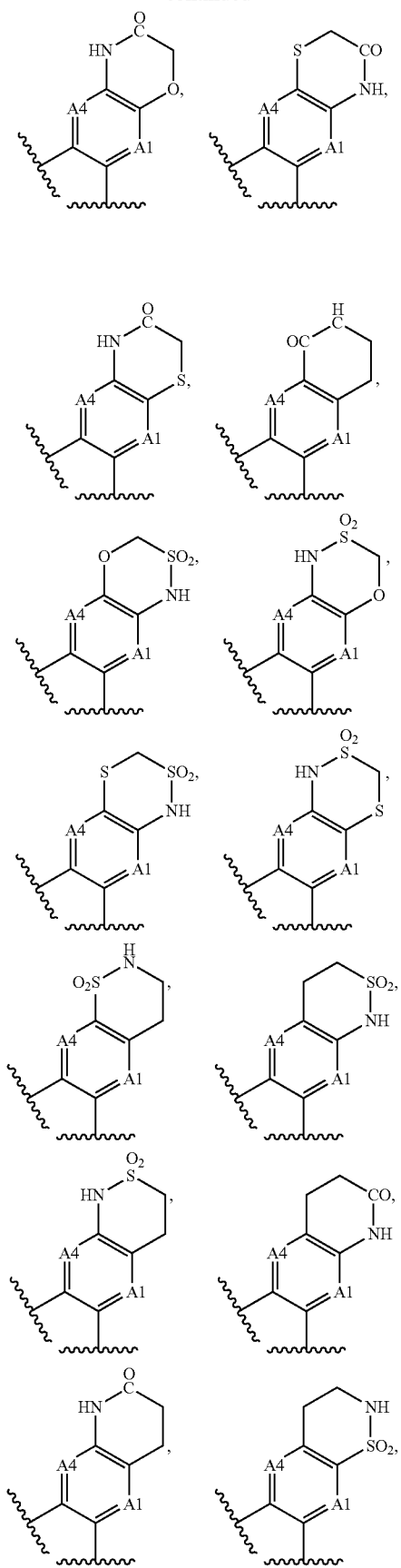

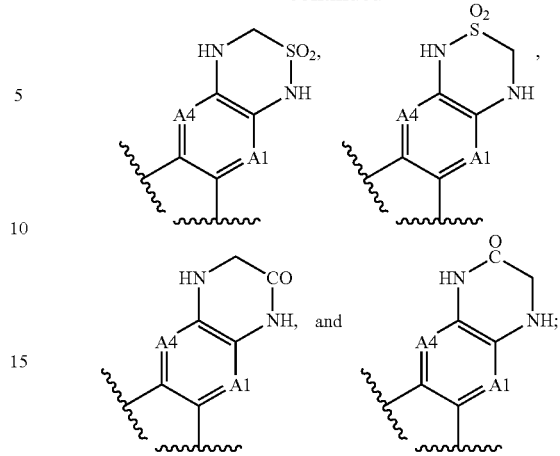

wherein each of the above formulas can be optionally substituted by one or more $R^B$ on the 5- or 6-membered ring corresponding to Ring B by up to 5 substituents or up to the available substitutable valencies, whichever is less. In some embodiments, A1 and A4 are each CH.

In some embodiments, the bicyclic moiety containing Ring B is selected from:

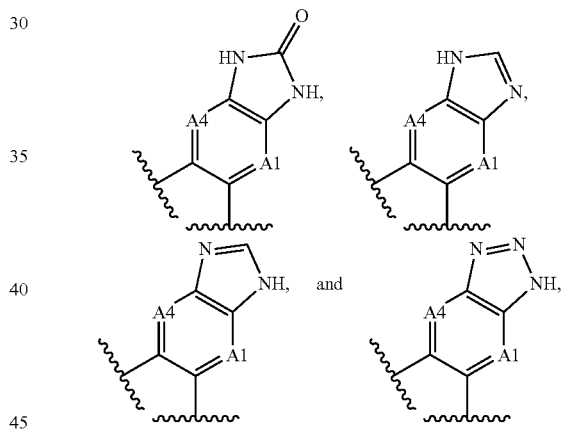

wherein each of the above formulas can be optionally substituted as valency allows by one or two $R^B$ on the 5-membered ring corresponding to Ring B. In some embodiments, A1 and A4 are each CH.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a substituent. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-6}$, and the like.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1, 2, 3, 4-tetrahydro-naphthalene is an example of a 10-membered cycloalkyl group.

As used herein, the term "$C_{i-j}$ alkyl," employed alone or in combination with other terms, refers to a saturated hydrocarbon group that may be straight-chain or branched, having i to j carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{i-j}$ alkoxy," employed alone or in combination with other terms, refers to a group of formula —O-alkyl, wherein the alkyl group has i to j carbons. Example alkoxy groups include methoxy, ethoxy, and propoxy (e.g., n-propoxy and isopropoxy). In some embodiments, the alkyl group has 1 to 3 carbon atoms.

As used herein, "$C_{i-j}$ alkenyl," employed alone or in combination with other terms, refers to an unsaturated hydrocarbon group having one or more double carbon-carbon bonds and having i to j carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{i-j}$ alkynyl," employed alone or in combination with other terms, refers to an unsaturated hydrocarbon group having one or more triple carbon-carbon bonds and having i to j carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{i-j}$ alkylamino," employed alone or in combination with other terms, refers to a group of formula —NH(alkyl), wherein the alkyl group has i to j carbon atoms. In some embodiments, the alkyl group has 1 to 6 or 1 to 4 carbon atoms.

As used herein, the term "di-$C_{i-j}$-alkylamino," employed alone or in combination with other terms, refers to a group of formula —N(alkyl)$_2$, wherein each of the two alkyl groups has, independently, i to j carbon atoms. In some embodiments, each alkyl group independently has 1 to 6 or 1 to 4 carbon atoms.

As used herein, the term "$C_{i-j}$ alkylthio," employed alone or in combination with other terms, refers to a group of formula —S-alkyl, wherein the alkyl group has i to j carbon atoms. In some embodiments, the alkyl group has 1 to 6 or 1 to 4 carbon atoms.

As used herein, the term "amino," employed alone or in combination with other terms, refers to a group of formula —NH$_2$.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "carbonyl", employed alone or in combination with other terms, refers to a —C(O)— group.

As used herein, the term "$C_{i-j}$ cycloalkyl," employed alone or in combination with other terms, refers to a non-aromatic cyclic hydrocarbon moiety having i to j ring-forming carbon atoms, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-7}$ cycloalkyl. Examplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like.

As used herein, "$C_{i-j}$ haloalkoxy," employed alone or in combination with other terms, refers to a group of formula —O-haloalkyl having i to j carbon atoms. An example haloalkoxy group is OCF$_3$. An additional example haloalkoxy group is OCHF$_2$. In some embodiments, the haloalkoxy group is fluorinated only. In some embodiments, the alkyl group has 1 to 6 or 1 to 4 carbon atoms.

As used herein, the term "halo," employed alone or in combination with other terms, refers to a halogen atom selected from F, Cl, I or Br. In some embodiments, "halo" refers to a halogen atom selected from F, Cl, or Br. In some embodiments, the halo substituent is F.

As used herein, the term "$C_{i-j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl," employed alone or in combination with other terms, refers to a monocyclic or polycyclic (e.g., having 2, 3 or 4 fused rings) aromatic heterocylic moiety, having one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1, 2-b] thiazole, purine, triazine. and the like.

A 5-membered heteroaryl is a heteroaryl group having five ring-forming atoms comprising wherein one or more of the ring-forming atoms are independently selected from N, O, and S. In some embodiments, the 5-membered heteroaryl group has 1, 2, or 3 heteroatom ring members. In some embodiments, the 5-membered heteroaryl group has 1 or 2 heteroatom ring members. In some embodiments, the 5-membered heteroaryl group has 1 heteroatom ring member. Example ring-forming members include CH, N, NH, O, and S. Example five-membered ring heteroaryls are thienyl, furyl, pyrrolyl, imidazolyl, thiazolyl, oxazolyl, pyrazolyl, isothiazolyl, isoxazolyl, 1, 2, 3-triazolyl, tetrazolyl, 1, 2, 3-thiadiazolyl, 1, 2, 3-oxadiazolyl, 1, 2, 4-triazolyl, 1, 2, 4-thiadiazolyl, 1, 2, 4-oxadiazolyl, 1, 3, 4-triazolyl, 1, 3, 4-thiadiazolyl, and 1, 3, 4-oxadiazolyl.

A 6-membered heteroaryl is a heteroaryl group having six ring-forming atoms wherein one or more of the ring-forming atoms is N. In some embodiments, the 6-membered heteroaryl group has 1, 2, or 3 heteroatom ring members. In some embodiments, the 6-membered heteroaryl group has 1 or 2 heteroatom ring members. In some embodiments, the 6-membered heteroaryl group has 1 heteroatom ring member. Example ring-forming members include CH and N. Example six-membered ring heteroaryls are pyridyl, pyrazinyl, pyrimidinyl, triazinyl, and pyridazinyl.

As used herein, the term "heterocycloalkyl," employed alone or in combination with other terms, refers to non-aromatic heterocyclic ring system, which may optionally contain one or more unsaturations as part of the ring structure, and which has at least one heteroatom ring member independently selected from nitrogen, sulfur and oxygen. In some embodiments, the heterocycloalkyl group has 1, 2, 3, or 4 heteroatom ring members. In some embodiments, the heterocycloalkyl group has 1, 2, or 3 heteroatom ring members. In some embodiments, the heterocycloalkyl group has 1 or 2 heteroatom ring members. In some embodiments, the heterocycloalkyl group has 1 heteroatom ring member. When the heterocycloalkyl group contains more than one heteroatom in the ring, the heteroatoms may be the same or different. Example ring-forming members include CH, $CH_2$, C(O), N, NH, O, S, S(O), and $S(O)_2$. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused (i.e., having a bond in common with) to the non-aromatic ring, for example, 1, 2, 3, 4-tetrahydro-quinoline, dihydrobenzofuran and the like. The carbon atoms or heteroatoms in the ring(s) of the heterocycloalkyl group can be oxidized to form a carbonyl, sulfinyl, or sulfonyl group (or other oxidized linkage) or a nitrogen atom can be quaternized. In some embodiments, heterocycloalkyl is 5- to 10-membered. Examples of heterocycloalkyl groups include 1, 2, 3, 4-tetrahydro-quinoline, dihydrobenzofuran, azetidine, azepane, pyrrolidine, piperidine, piperazine, morpholine, thiomorpholine, and pyran.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1, 2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1, 2, 4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DIAD (N, N'-diisopropyl azidodicarboxylate); DIPEA (N, N-diisopropylethylamine); DMF (N, N-dimethylformamide); Et (ethyl); EtOAc (ethyl acetate); g (gram(s)); h (hour(s)); HATU (N, N, N', N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); μg (microgram(s)); μL (microliter(s)); μM (micromolar); wt % (weight percent).

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4$^{th}$ Ed., Wiley & Sons, Inc., New York (2006), which is incorporated herein by reference in its entirety. Protecting groups in the synthetic schemes are typically represented by "PG."

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Compounds of Formula I can be formed as shown in Scheme I. The heterocyclic halide (i) (Hal=Cl, Br, or I) can be coupled to M-Het, where M is a boronic acid, boronic ester or an appropriately substituted metal (e.g., Het-M is Het-B(OH)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0)) and a base (e.g., bicarbonate or carbonate base) or standard Negishi conditions (e.g., in the presence of a palladium(0) catalyst, such as tetrakis(triphenylphosphine)palladium(0)), to give a derivative of Formula I (iii).

Alternatively, heterocyclic halide (i) can be converted to a boronic acid or boronate ester (iv) under standard transmetalation conditions (e.g., pinacol boronate, in the presence of a palladium(0) catalyst, such as tetrakis(triphenylphosphine)palladium(0)). The heterocyclic boronate (iv) can be coupled to halo substituted heterocycles (v), (e.g., Hal-Het, where Hal=Cl, Br, or I), under standard Suzuki conditions or standard Stille conditions (e.g., in the presence of a palladium(0) catalyst, such as tetrakis(triphenylphosphine)palladium(0)) and a base (e.g., bicarbonate or carbonate base) or standard Negishi conditions (e.g., in the presence of a palladium(0) catalyst, such as tetrakis(triphenylphosphine)palladium(0)) to give a compound of Formula I (iii).

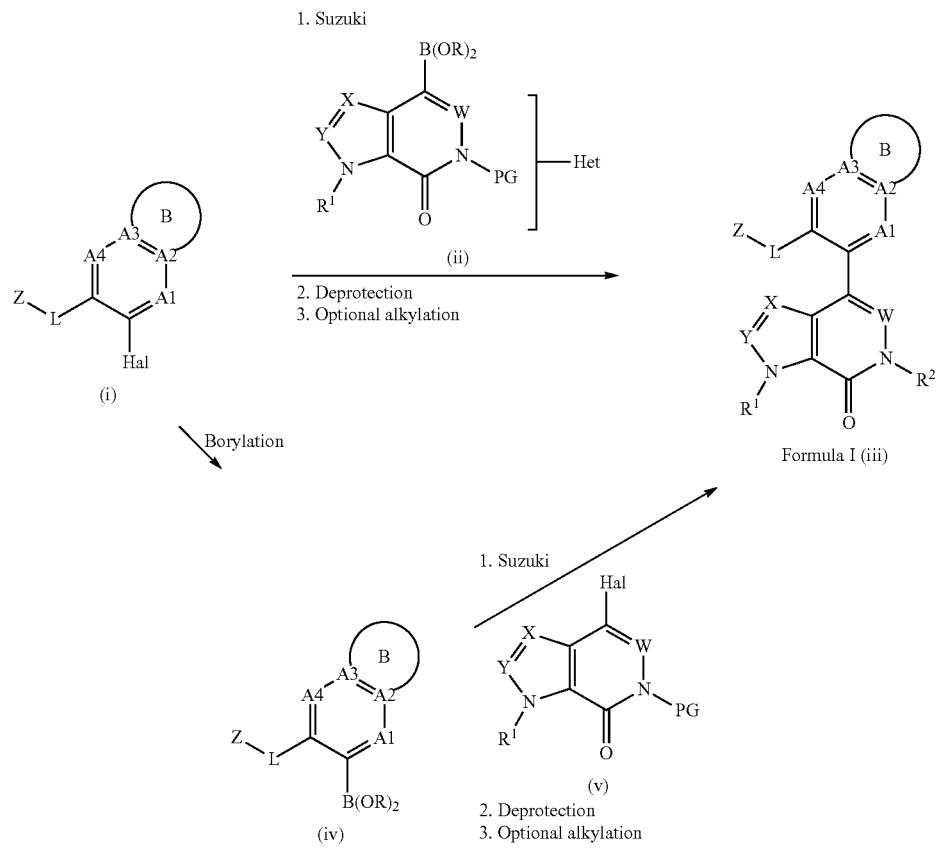

Scheme 1

Synthesis of heterocyclic intermediates useful in the preparation of compounds of Formula I can be formed as shown in Scheme II. The heterocycle (i) can be alkylated (e.g., Z-Hal, where Hal=Br, Cl, or I) with a base (e.g., triethylamine, NaH or $Na_2CO_3$) or under Mitsunobu conditions to afford the heterocycle (ii). Alternatively, heterocycle (i) can be arylated either under Evans' conditions with an aryl-boronic acid (e.g., Z—$B(OR)_2$, in the presence of a palladium(0) catalyst) or Ullman conditions with an aryl halide (e.g., Z-Hal, in the presence of palladium(0)) to afford the heterocycle (ii). Halogenation of heterocycle (ii) under standard conditions ($Br_2$, AcOH or N-chlorosuccinamide, N-bromosuccinamide or N-iodosuccinamide) can give halide (iii) where Hal=Cl, Br or I.

Scheme II

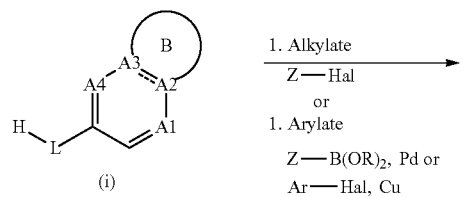

Synthesis of heterocyclic intermediates useful in the preparation of compounds of Formula I can be formed as shown in Scheme III. Halogenation of heterocycle (i) under standard conditions (e.g., $Br_2$, AcOH or N-chlorosuccinamide, N-bromosuccinamide or N-iodosuccinamide) can give halide (ii) where Hal=Cl, Br or I. The heterocycle (ii) can be alkylated (e.g., Z-Hal, where Hal=Br, Cl, or I) with a base, (e.g. triethylamine, NaH or $Na_2CO_3$) or under Mitsunobu conditions to afford the heterocycle (iii). Alternatively, heterocycle (ii) can be arylated either under Evans' conditions with an aryl-boronic acid (e.g., Z—$B(OR)_2$, in the presence of a palladium(0) catalyst) or Ullmann conditions with an aryl halide (e.g., Z-Hal, in the presence of copper) to afford the heterocycle (iii).

Scheme III

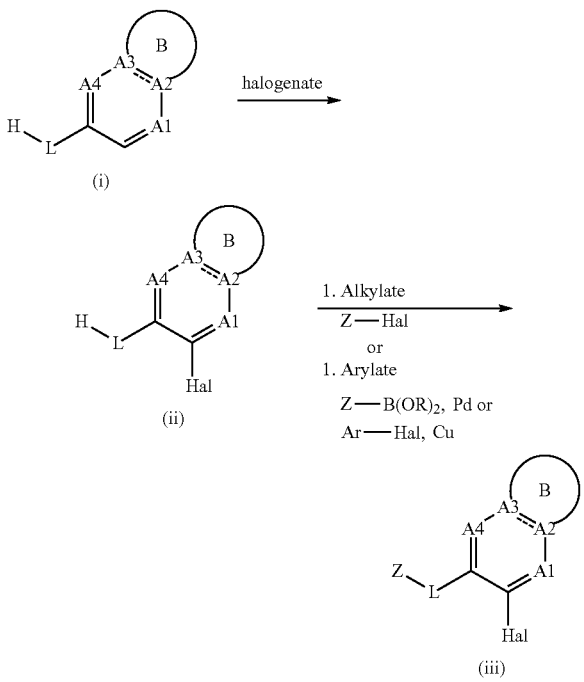

Compounds of Formula I can be formed as shown in Scheme IV. The heterocyclic fluoride (i) can be coupled to Het-M (ii), where M is a boronic acid, boronic ester or an appropriately substituted metal (e.g., Het-M is Het-$B(OH)_2$, Het-$B(OR)_2$, Het-$Sn(Bu)_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)), to give a compound of formula (iii).

Alternatively, heterocyclic halide (i) can be converted to a boronic acid or boronate acid (iv) under standard transmetalation conditions (e.g., pinacol boronate, in the presence of a palladium(0) catalyst, such as tetrakis(triphenylphosphine)palladium(0)). The heterocyclic boronate (iv) can be coupled to halo substituted heterocycle (v) (e.g., Hal-Het, where Hal is a halide (e.g., Hal=Cl, Br, or I)), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give the compounds of formula (iii). Thiols, amines, and alcohols of formula H-L-Z can displace the fluoro group of compounds (iii) using standard conditions (e.g., $Cs_2CO_3$/DMSO) to give thioethers, arylamines, and ethers of Formula I (vi) after deprotection of the nitrogen protecting group and optional alkylation with Hal-$R^2$.

Scheme IV

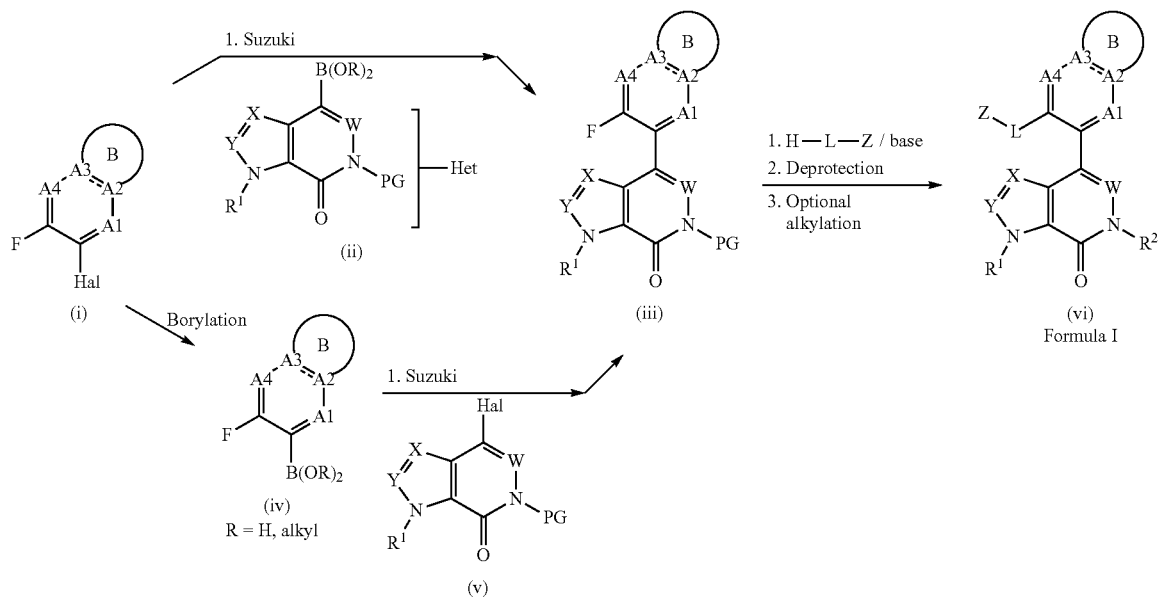

Synthesis of heterocyclic intermediates useful in the preparation of compounds of Formula I can be formed as shown in Scheme V. Conversion of Hal derivative (i) wherein Hal=Br, Cl, or I, with 1,1-dimethoxy-N,N-dimethylmethanamine in the absence or presence of a base can provide enamines (ii). Catalytic hydrogenation of (ii) in the presence of a catalyst (e.g., Raney-Nickel under hydrogen atmosphere) can provide amines that cyclize to form a heterocycle. Protection of the heterocyclic nitrogen atom with a protecting group such as, but not limited to, benzyl, tosyl, and (trimethylsilyl)ethoxy)methyl group can provide heterocycle (iii). Hydrolysis of the methoxy substituent with an acid such as, but not limited to, hydrochloric acid or hydrobromic acid provides heterocycles (iv). Compound (iv) can be alkylated (e.g., $R^2$-Hal and a base (e.g., triethylamine, NaH or $Na_2CO_3$) or under Mitsunobu conditions) to afford the heterocycle (v). The conversion of halide (v) to the boronate ester (vi) or boronic acid (vi) can be performed under standard conditions (e.g., pinacol boronate, in the presence of a palladium(0) catalyst, such as tetrakis(triphenylphosphine)palladium(0)).

Scheme V

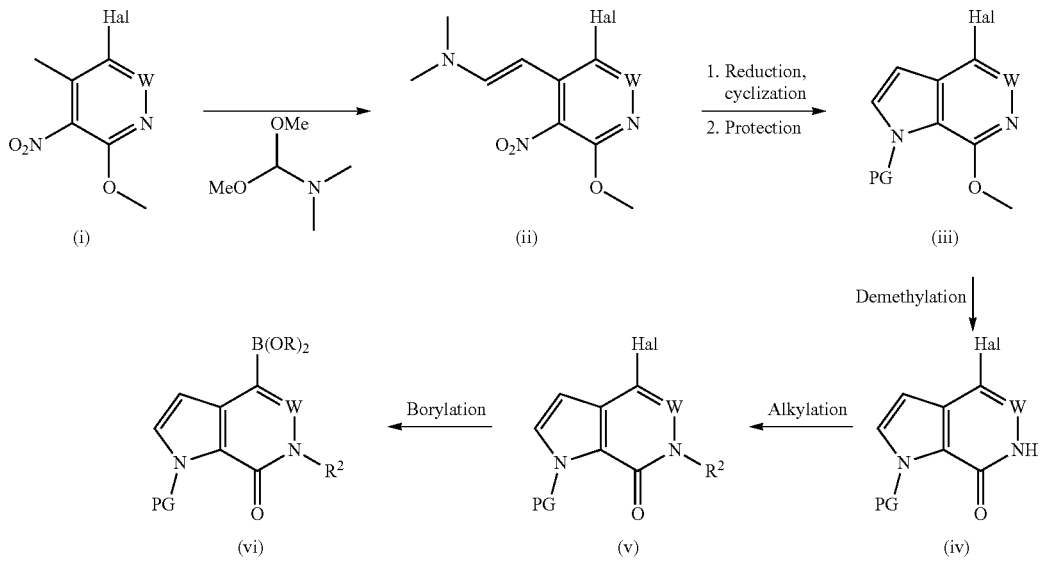

Synthesis of heterocyclic intermediates useful in the preparation of compounds of Formula I can be formed as shown in Scheme VI. Conversion of halo heterocycle (i) with ammonium hydroxide can afford amines (ii). Iodination of amine (ii) with N-iodosuccinimide can afford iodo derivatives (iii). Coupling with (E)-2-(2-ethoxyvinyl)-4,4,5,5-tetramethyl-1,3,2-dioxaborolane utilizing Suzuki coupling reaction conditions (e.g., in the presence of a palladium(0) catalyst, such as tetrakis(triphenylphosphine)palladium(0)

and a base (e.g., bicarbonate or carbonate base)) can provide heterocycles (iv). Cyclization of (iv) in the presence of an acid such as, but not limited to, acetic acid or hydrochloric acid, followed by protection of the nitrogen atom can afford heterocycles (v). The conversion of halide (v) to the boronate ester (vi) or boronic acid (vi) can be performed under standard conditions (e.g., pinacol boronate, in the presence of a palladium(0) catalyst, such as tetrakis(triphenylphosphine)palladium(0)).

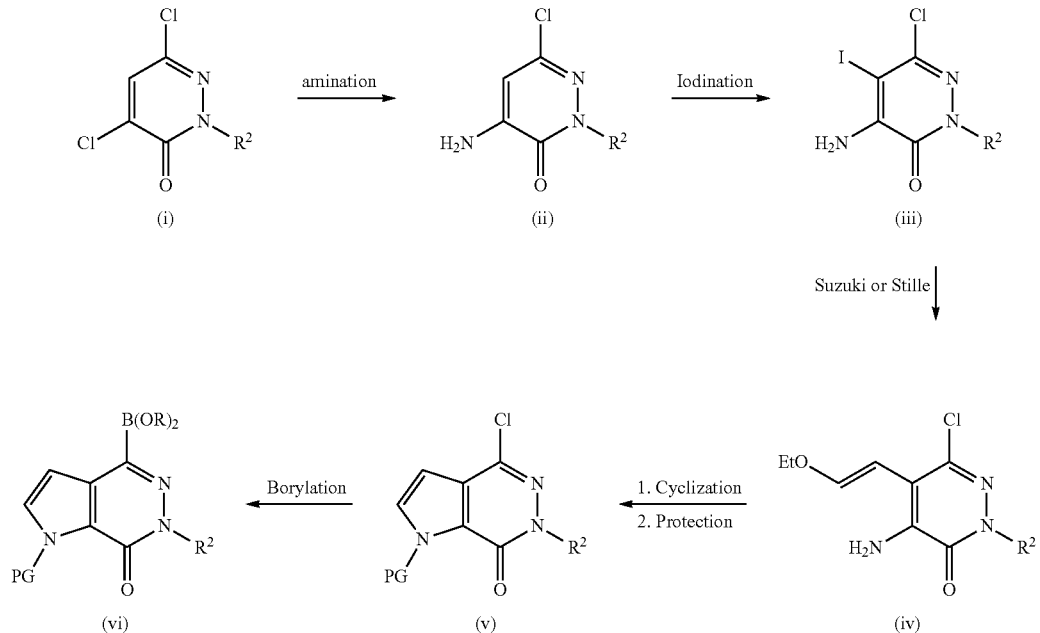

Synthesis of heterocyclic intermediates useful in the preparation of compounds of Formula I can be formed as shown in Scheme VII. Conversion of iodo derivative (i) to heterocyclic acid (ii) can be performed by reacting with pyruvic acid in the presence of a palladium catalyst (e.g., palladium(II)acetate, and a base such as DBU). Esterification of the acid (ii) can be performed by standard reaction conditions such as treatment with an alcohol under acidic condition. Protection of the nitrogen of the heterocycle (iii) can be performed under standard conditions to give N-protected heterocycle (iv). Hydrolysis of the ester to the acid and formation of the amide (v) can be performed under standard peptide coupling conditions, (e.g., amine HNRR in the presence of a coupling reagent, such as, 1,1'-carbonyldiimidazole (CDI) or N,N,N',N'-tetramethyluronium hexafluorophosphate (HATU)). The conversion of halide (v) to the boronate ester (vi) or boronic acid (vi) can be performed under standard condition (e.g., pinacol boronate, in the presence of a palladium(0) catalyst, such as tetrakis (triphenylphosphine)palladium(0)).

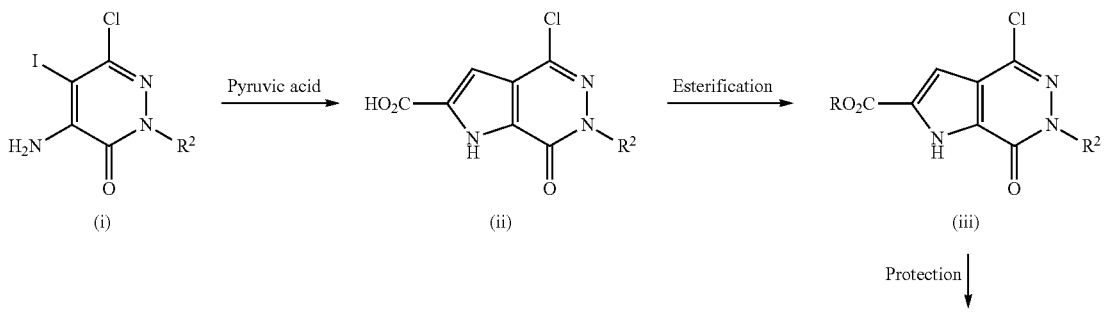

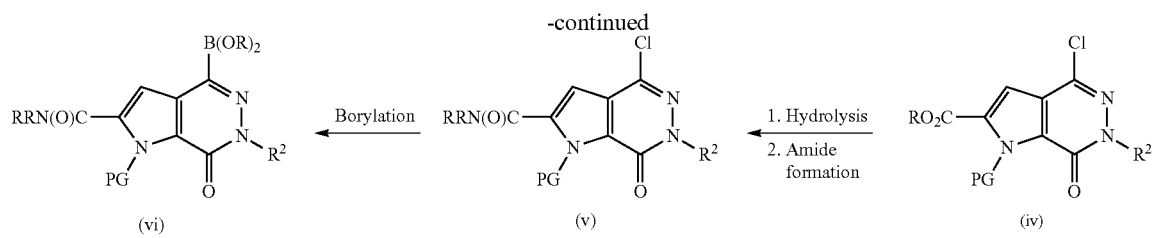

Synthesis of heterocyclic intermediates useful in the preparation of compounds of Formula I can be formed as shown in Scheme VIII. Reaction of heterocycle (i) with an oxalate ester in the presence of a base (e.g., potassium ethoxide) and reduction followed by cyclization of the resulting ester (ii) upon heating and protection of the heterocyclic nitrogen can afford heterocycle (iii). Cleavage of the methyl ether under acidic conditions can afford heterocycle (iv). Compounds of formula (iv) can be alkylated (e.g., $R^2$-Hal, where Hal=Br, Cl, or I) with a base, such as triethylamine, NaH or $Na_2CO_3$ or under Mitsunobu conditions to afford the heterocycle (v). The conversion of halide (v) to the boronate ester (vi) or boronic acid (vi) can be performed under standard condition (e.g., pinacol boronate, in the presence of a palladium(0) catalyst, such as tetrakis(triphenylphosphine)palladium(0)).

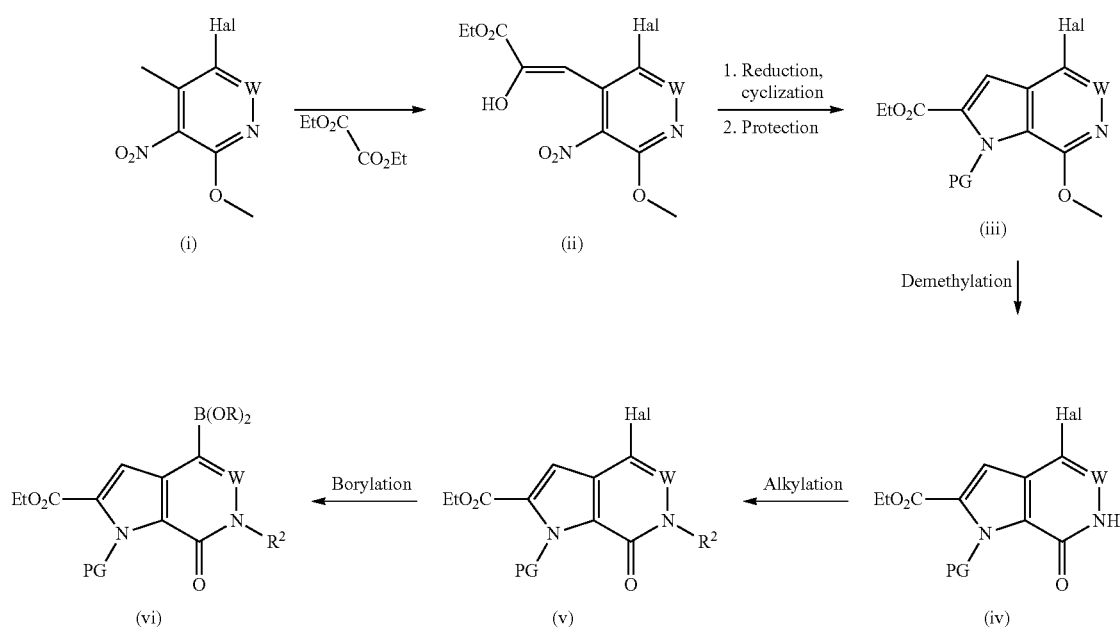

Synthesis of heterocyclic intermediates useful in the preparation of compounds of Formula I can be formed as shown in Scheme IX. Heterocycle (i) can be alkylated with $R^2$-Hal (Hal=Cl, Br, I, or other leaving group, e.g., MeI) and a suitable base (e.g., NaH) to give compound (ii). Selective reduction of the nitro heterocycle (ii) (e.g., Hal=Cl, Br or I using iron with AcOH or HCl) can give the amine (iii). Cyclization of (iii) to (iv) can be accomplished by isoamylnitrite. Protection of the nitrogen of (iv) can be accomplished using standard conditions (e.g., tosylchloride and NaH) to give (v). The conversion of halide (v) to the boronate ester (vi) or boronic acid (vi) can be performed under standard condition (e.g., pinacol boronate, in the presence of a palladium(0) catalyst, such as tetrakis(triphenylphosphine)palladium(0)).

Scheme IX

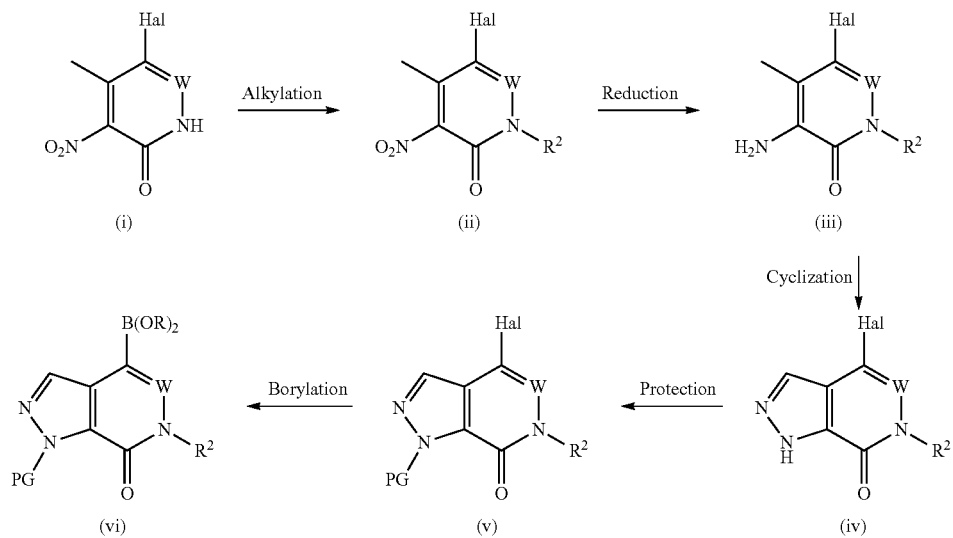

Synthesis of compounds of Formula I can be formed as shown in Scheme X. Thiols, amines, and alcohols of formula H-L-Z can displace the fluoro group of compounds (i) using standard conditions (e.g., $Cs_2CO_3$/DMSO) to give thioethers, arylamines, and ethers of formula (ii) where L=S, NR, and O, respectively. Selective reduction of the nitro benzene (ii) (when Hal=Cl, Br or I) using iron/AcOH can give the bis-aniline (iii). Conversion of bis-aniline to urea can occur under standard conditions (e.g., carbonyl diimidazole or triphosgene) to give (iv). The heterocyclic halide (iv) can be coupled to Het-M (v), where M is a boronic acid, boronic ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0)) and a base (e.g., bicarbonate or carbonate base) or standard Negishi conditions (e.g., in the presence of a palladium(0) catalyst, such as tetrakis(triphenylphosphine)palladium(0)) to give compounds (vi). Deprotection of (vi) can give compounds of Formula I (vii).

Scheme X

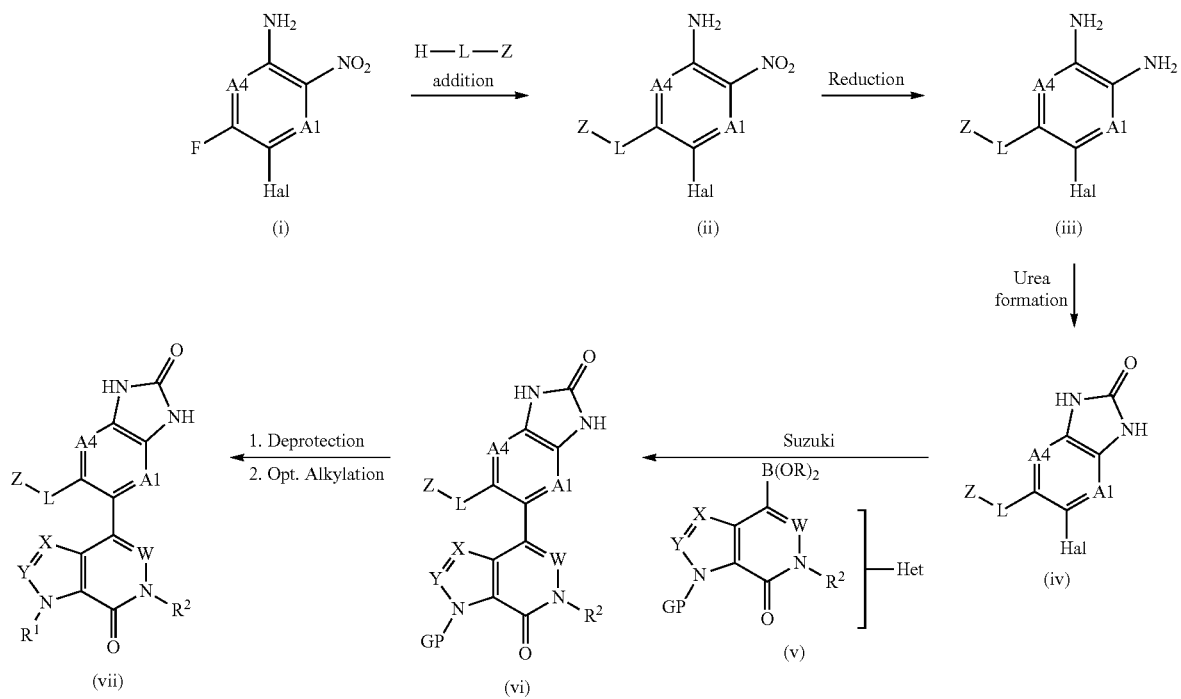

Compounds of Formula I can be formed as shown in Scheme XI. Aniline (i) (from Scheme X) can be converted to the trifluoroacetamide using standard conditions (e.g., trifluoroacetic anhydride) and then alkylated with $R^B$-Hal (e.g., Hal=Cl, Br, I, or other leaving group, e.g., MeI) and a suitable base (e.g., NaH) to give compound (ii). Removal of the trifluoroacetamide followed by selective reduction of the nitro (when Hal=Cl, Br or I) using iron/AcOH can give the bis-aniline (iii). Conversion of bis-aniline to urea can occur under standard conditions (e.g., carbonyl diimidazole or triphosgene) to give (iv). The heterocyclic halide (iv) can be coupled to Het-M (v), where M is a boronic acid, boronic ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds (vi). Deprotection of (vi) can give compounds of the invention (vii).

Compounds of Formula I can be formed as shown in Scheme XII. The aniline (i) can be coupled to Het-M (ii), where M is a boronic acid, boronic ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds (iii). The nitro group of (iii) can be reduced to give the bis-aniline which can be converted to the urea under standard conditions (e.g., carbonyl diimidazole or triphosgene) to give (vii). Deprotection of (vii) can give compounds of the invention (vi).

Alternatively, the aniline of compound (iii) can be converted to the trifluoroacetamide using standard conditions (e.g., trifluoroacetic anhydride) and then alkylated with $R^B$-Hal (Hal=Cl, Br, I, or other leaving group, eg. MeI) and a suitable base (e.g., NaH) to give compound (iv). Removal of the trifluoroacetamide followed by reduction of the nitro under standard conditions (e.g., hydrogenation with palladium, iron/AcOH, or zinc) can give the bis-aniline which can be converted to the urea under standard conditions (e.g., carbonyl diimidazole or triphosgene) to give (v). Finally deprotection of (v) can give compounds of the invention (vi).

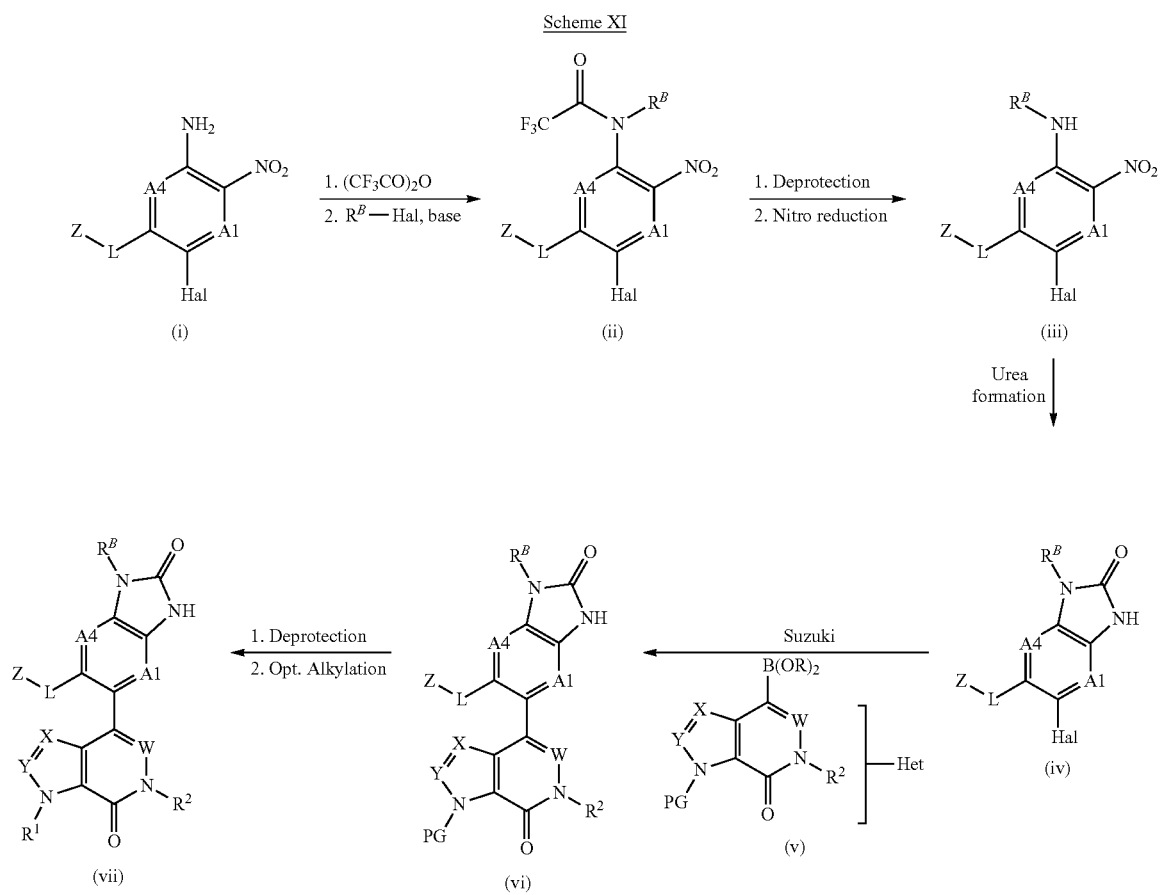

Scheme XI

Scheme XII

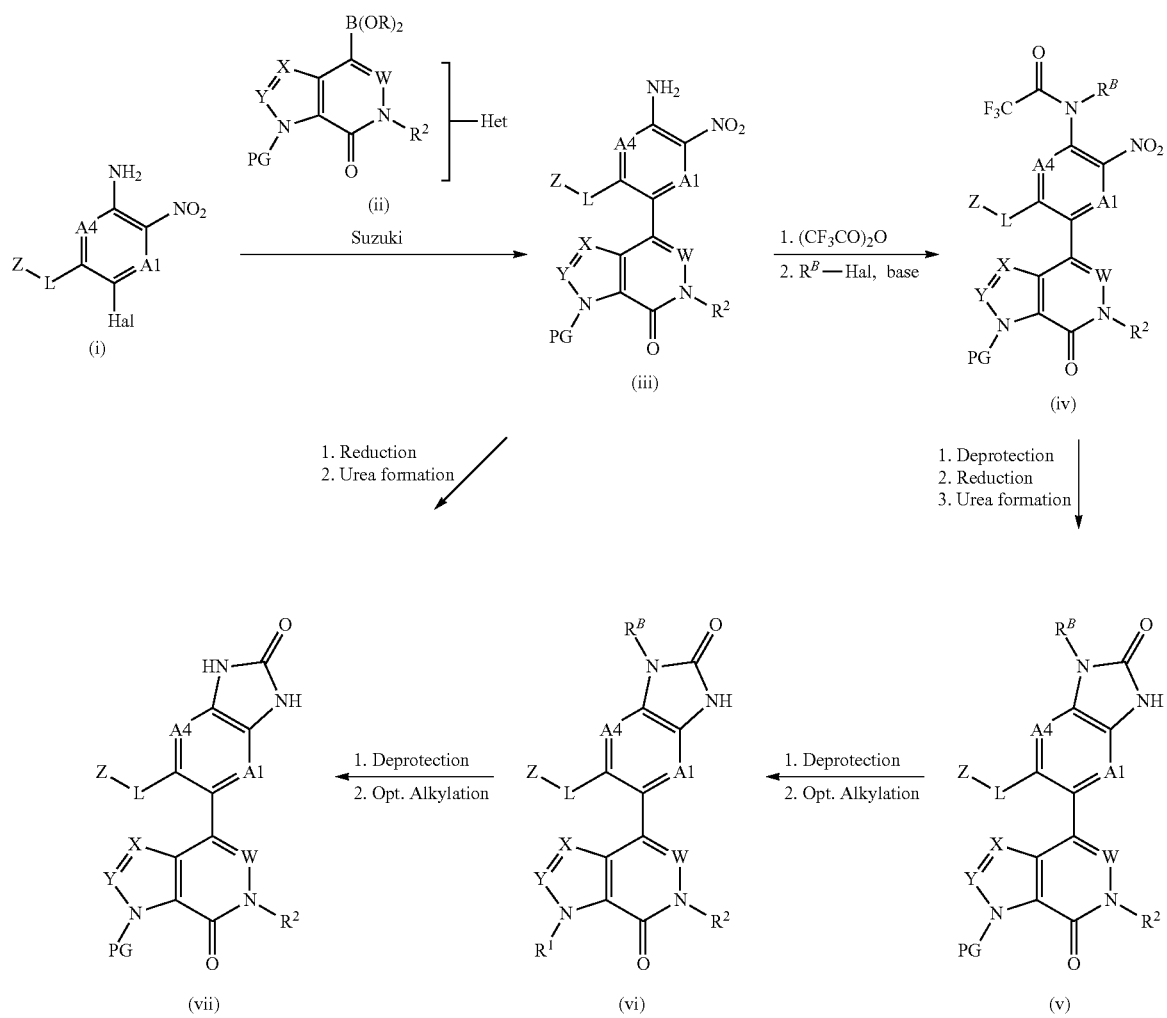

Compounds of Formula I can be formed as shown in Scheme XIII. Selective reduction of the nitro benzene (i) (when Hal=Cl, Br or I) using iron/AcOH can give the bis-aniline which can be converted under standard conditions (e.g., $(EtO)_3CR^B$ with p-TsOH, $R^BCHO$ with TMSCl or peroxide/HCL or copper catalyzed, or $R^BCO_2H$ with borane) to give benzimidazole (ii). The benzimidazole (ii) can be coupled to Het-M (iii), where M is a boronic acid, boronate ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds (iv). Finally deprotection of (iv) can give compounds of the invention (v).

Alternatively, aniline (i) can be converted to the trifluoroacetamide using standard conditions (e.g., trifluoroacetic anhydride) and then alkylated with $R^B$-Hal (Hal=Cl, Br, I, or other leaving group, eg. MeI) and a suitable base (e.g., NaH) to give compound (vi). Removal of the trifluoroacetamide followed by selective reduction of the nitro (when Hal=Cl, Br or I) using iron/AcOH can give the bis-aniline which can be converted under standard conditions (e.g., $(EtO)_3CR^B$ with p-TsOH, $R^BCHO$ with TMSCl or peroxide/HCL or copper catalyzed, or $R^BCO_2H$ with borane) to give benzimidazole (vii). The benzimidazole (vii) can be coupled to Het-M (iii), where M is a boronic acid, boronic ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds of the invention (v) after deprotection and optional alkylation.

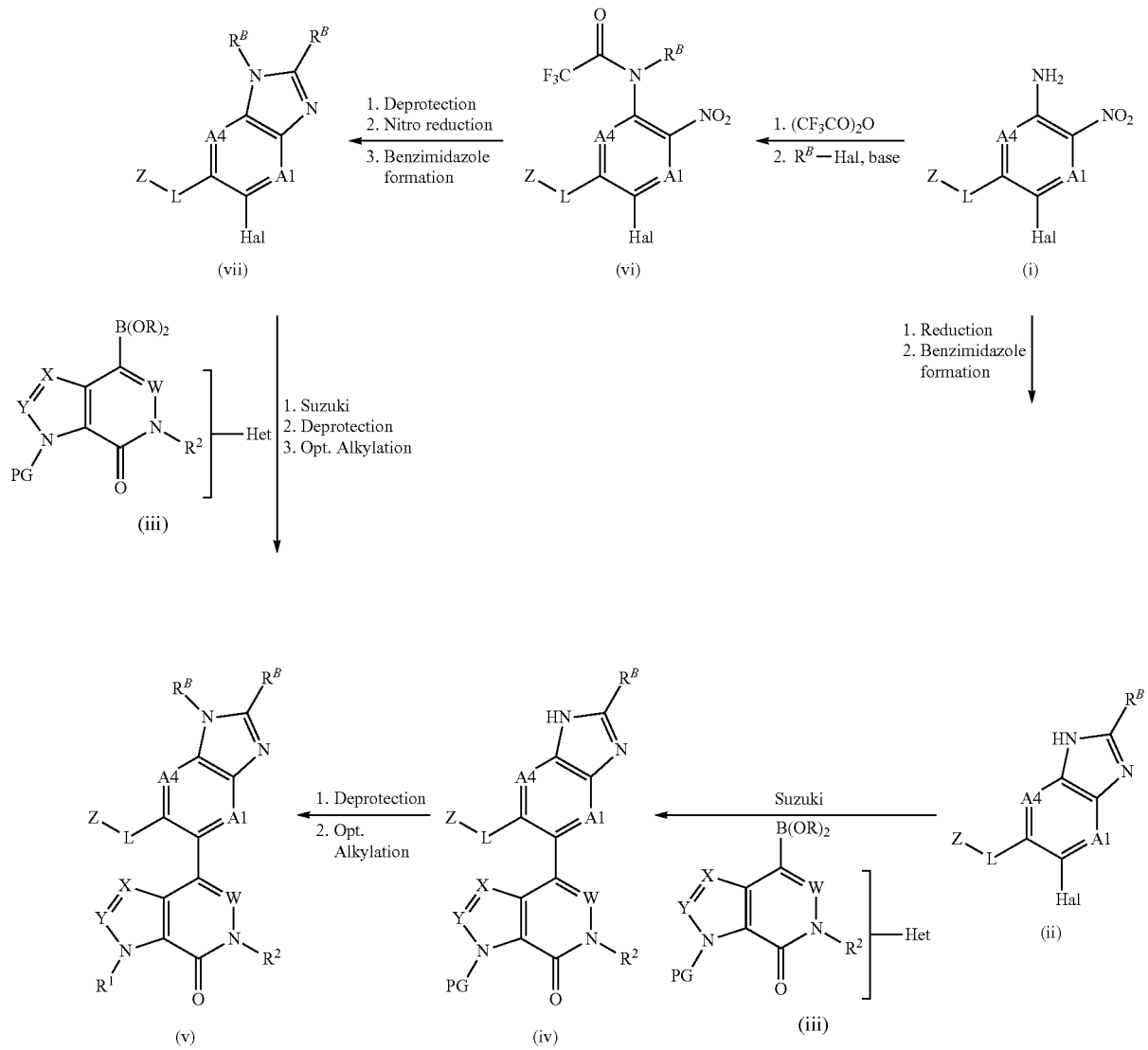

Scheme XIII

Compounds of Formula I can be formed as shown in Scheme XIV. Selective reduction of the nitro benzene (i) (when Hal=Cl, Br or I) using iron/AcOH can give the bis-aniline which can be converted (e.g., sodium nitrite/acetic acid) to benzotriazole (ii). The benzotriazole (ii) can be coupled to Het-M (iii), where M is a boronic acid, boronate ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds (iv). Finally deprotection of (iv) can give compounds of the invention (v).

Alternatively, aniline (i) can be converted to the trifluoroacetamide using standard conditions (e.g., trifluoroacetic anhydride) and then alkylated with $R^B$-Hal (Hal=Cl, Br, I, or other leaving group, eg. MeI) and a suitable base (e.g., NaH) to give compound (vi). Removal of the trifluoroacetamide followed by selective reduction of the nitro (when Hal=Cl, Br or I) using iron/AcOH can give the bis-aniline which can be converted (e.g., sodium nitrite with acetic acid) to benzotriazole (vii). The benzotriazole (vii) can be coupled to Het-M (iii), where M is a boronic acid, boronic ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds of the invention (v) after deprotection and optional alkylation.

Scheme XIV

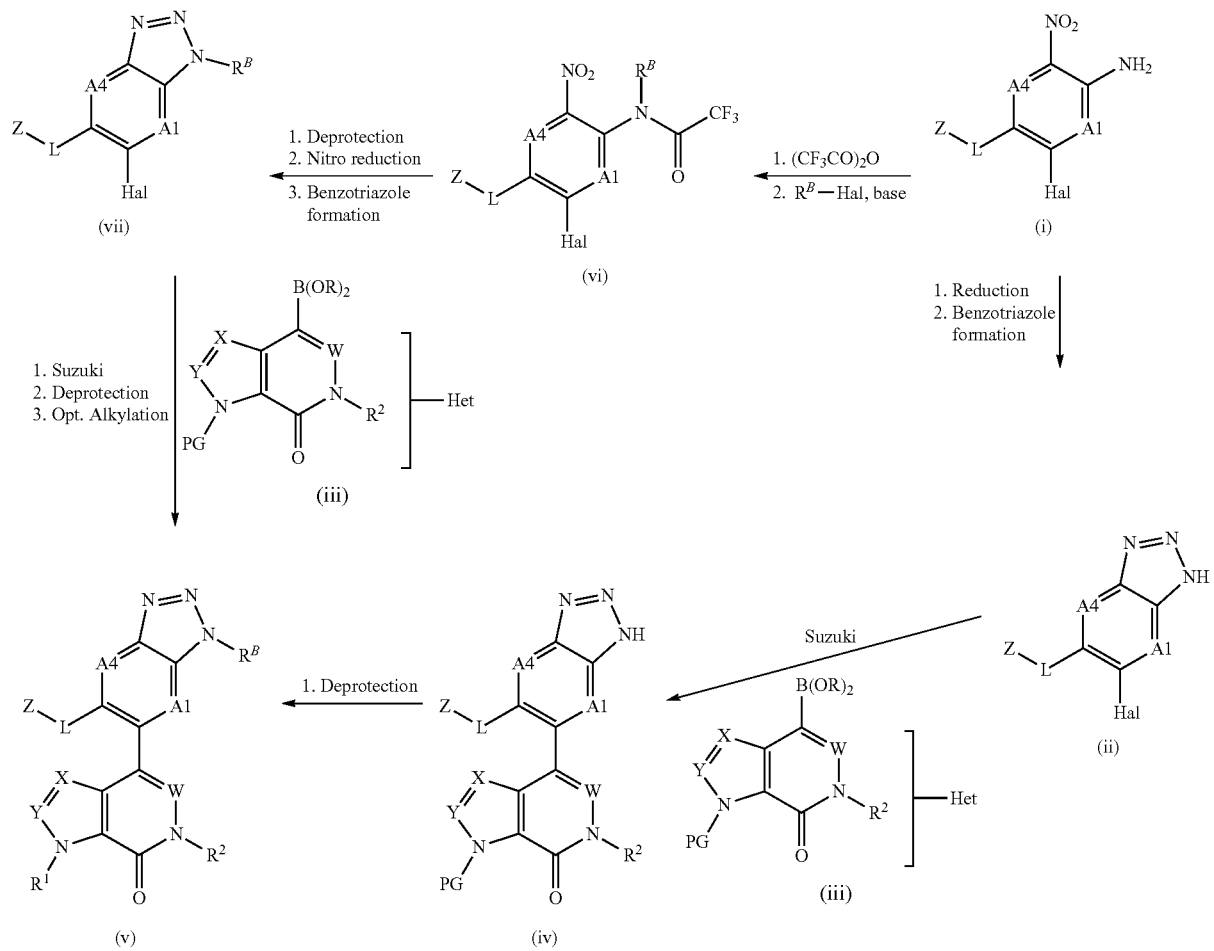

Methods of Use

Compounds of the invention are BET protein inhibitors and, thus, are useful in treating diseases and disorders associated with activity of BET proteins. For the uses described herein, any of the compounds of the invention, including any of the embodiments thereof, may be used.

The compounds of the invention can inhibit one or more of BET proteins BRD2, BRD3, BRD4, and BRD-t. In some embodiments, the BET protein is BRD2. In some embodiments, the BET protein is BRD3. In some embodiments, the BET protein is BRD4. In some embodiments, the BET protein is BRD-t. In some embodiments, the compounds of the invention selectively inhibit one or more BET proteins over another. "Selective" means that the compound binds to or inhibits a BET protein with greater affinity or potency, respectively, compared to a reference, such as another BET protein. For example, the compounds can be selective for BRD2 over BRD3, BRD4 and BRD-t, selective for BRD3 over BRD2, BRD4 and BRD-t, selective for BRD4 over BRD2, BRD3 and BRD-t, or selective for BRD-t over BRD2, BRD3 and BRD4. In some embodiments, the compounds inhibit two or more of the BET proteins, or all of the BET proteins. In general, selectivity can be at least about 5-fold, at least about 10-fold, at least about 20-fold, at least about 50-fold, at least about 100-fold, at least about 200-fold, at least about 500-fold or at least about 1000-fold.

In some embodiments, the present invention is directed to a method of inhibiting BRD2 comprising contacting a compound of the invention with BRD2. In some embodiments, the present invention is directed to a method of inhibiting BRD3 comprising contacting a compound of the invention with BRD3. In some embodiments, the present invention is directed to a method of inhibiting BRD4 comprising contacting a compound of the invention with BRD4. In some embodiments, the present invention is directed to a method of inhibiting BRD-t comprising contacting a compound of the invention with BRD-t.

The compounds of the invention are therefore useful for treating BET protein mediated disorders. The term "BET-mediated" refers to any disease or condition in which one or more of the BET proteins, such as BRD2, BRD3, BRD4 and/or BRD-t, or a mutant thereof, plays a role, or where the disease or condition is associated with expression or activity of one or more of the BET proteins. The compounds of the invention can therefore be used to treat or lessen the severity of diseases and conditions where BET proteins, such as BRD2, BRD3, BRD4, and/or BRD-t, or a mutant thereof, are known to play a role.

Diseases and conditions treatable using the compounds of the invention include, but are not limited to, cancer and other proliferative disorders, autoimmune disease, chronic inflammatory diseases, acute inflammatory diseases, sepsis, and viral infection. The diseases can be treated by administering to an individual (e.g., a patient) in need of the treatment a therapeutically effective amount or dose of a compound of the invention, or any of the embodiments thereof, or a pharmaceutical composition thereof. The present disclosure also provides a compound of the invention, or any of the embodiments thereof, or a pharmaceutical composition thereof, for use in treating a BET-mediated disease or disorder. Also provided is the use of a compound of the invention, or any of the embodiments thereof, or a pharmaceutical composition thereof, in the manufacture of a medicament for treating a BET-mediated disease or disorder.

Diseases that can be treated with the compounds of the invention include cancers. The cancers can include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In some embodiments, the cancer can be adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

The diseases treatable using the compounds of the invention also include MYC dependent cancers wherein the cancer is associated with at least one of myc RNA expression or MYC protein expression. A patient can be identified for such treatment by determining myc RNA expression or MYC protein expression in the cancerous tissue or cells.

Diseases that can be treated with compounds of the invention also include non-cancerous proliferative disorders. Examples of proliferative disorders that can be treated include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The diseases and conditions that can be treated with the compounds of the invention also include chronic autoimmune and inflammatory conditions. Examples of autoimmune and inflammatory conditions that can be treated include acute, hyperacute or chronic rejection of transplanted organs, acute gout, acute inflammatory responses (such as acute respiratory distress syndrome and ischemia/reperfusion injury), Addison's disease, agammaglobulinemia, allergic rhinitis, allergy, alopecia, Alzheimer's disease, appendicitis, atherosclerosis, asthma, osteoarthritis, juvenile arthritis, psoriatic arthritis, rheumatoid arthriti, satopic dermatitis, autoimmune alopecia, autoimmune hemolytic and thrombocytopenic states, autoimmune hypopituitarism, autoimmune polyglandular disease, Behcet's disease, bullous skin diseases, cholecystitis, chronic idiopathic thrombocytopenic purpura, chronic obstructive pulmonary disease (COPD), cirrhosis, degenerative joint disease, depression, dermatitis, dermatomyositis, eczema, enteritis, encephalitis, gastritis glomerulonephritis, giant cell arteritis, Goodpasture's syndrome, Guillain-Barre syndrome, gingivitis, Graves' disease, Hashimoto's thyroiditis, hepatitis, hypophysitis, inflammatory bowel disease (Crohn's disease and ulcerative colitis), inflammatory pelvic disease, irritable bowel syndrome, Kawasaki disease, LPS-induced endotoxic shock, meningitis, multiple sclerosis, myocarditis, myasthenia gravis, mycosis fungoides, myositis, nephritis, osteomyelitis, pancreatitis, Parkinson's disease, pericarditis, pernicious anemia, pneumonitis, primary biliary sclerosing cholangitis, polyarteritis nodosa, psoriasis, retinitis, scleritis, scleracierma, scleroderma, sinusitis, Sjogren's disease, sepsis, septic shock, sunburn, systemic lupus erythematosus, tissue graft rejection, thyroiditis, type I diabetes, Takayasu's arteritis, urethritis, uveitis, vasculitis, vasculitis including giant cell arteritis, vasculitis with organ involvement such as glomerulonephritis, vitiligo, Waldenstrom macroglobulinemia and Wegener's granulomatosis.

The diseases and conditions that can be treated with the compounds of the invention also include diseases and conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Other diseases that can be treated with the compounds of the invention include viral infections. Examples of viral infections that can be treated include Epstein-Barr virus, hepatitis B virus, hepatitis C virus, herpes virus, human immunodeficiency virus, human papilloma virus, adenovirus, poxvirus and other episome-based DNA viruses. The compounds can therefore be used to treat disease and conditions such as herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus. In one particular embodiment, the compounds of the invention are indicated for the treatment of human papilloma virus infections of skin or cervical epithelia.

The diseases and conditions that can be treated with the compounds of the invention also include conditions that are associated with ischaemia-reperfusion injury. Examples of such conditions include, but are not limited to conditions such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

The compounds of the invention are also useful in the treatment of disorders of lipid metabolism via the regulation of APO-A1 such as hypercholesterolemia, atherosclerosis and Alzheimer's disease.

The compounds of the invention are also useful in the treatment of fibrotic conditions such as idiopathic pulmonary fibrosis, renal fibrosis, post-operative stricture, keloid formation, scleroderma and cardiac fibrosis.

The compounds of the invention can also be used to treat ophthamological indications such as dry eye.

The compounds of the invention can also be used to treat heart disease such as heart failure.

As used herein, the term "contacting" refers to the bringing together of indicated moieties in an in vitro system or an in vivo system. For example, "contacting" a BET protein with a compound of the invention includes the administration of a compound of the present invention to an individual or patient, such as a human, having a BET protein, as well as, for example, introducing a compound of the invention into a sample containing a cellular or purified preparation containing the BET protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "preventing" or "prevention" refers to preventing the disease; for example, preventing a disease, condition or disorder in an individual who may be predisposed to the disease, condition or disorder but does not yet experience or display the pathology or symptomatology of the disease.

Combination Therapies

The compounds of the invention can be used in combination treatments where the compound of the invention is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, and JAK kinase inhibitors for treatment of BET protein-associated diseases, disorders or conditions. The one or more additional pharmaceutical agents can be administered to a patient simultaneously or sequentially.

In some embodiments, the compounds of the invention can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the compounds of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating cancer and other proliferative diseases, the compounds of the invention can be used in combination with ruxolitinib.

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), $CF_{101}$ (2S, 3S, 4R, 5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the compound of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

Formulation, Dosage Forms and Administration

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

The compounds of the invention can be provided with or used in combination with a companion diagnostic. As used herein, the term "companion diagnostic" refers to a diagnostic device useful for determining the safe and effective use of a therapeutic agent. For example, a companion diagnostic may be used to customize dosage of a therapeutic agent for a given subject, identify appropriate subpopulations for treatment, or identify populations who should not receive a particular treatment because of an increased risk of a serious side effect.

In some embodiments, the companion diagnostic is used to monitor treatment response in a patient. In some embodiments, the companion diagnostic is used to identify a subject that is likely to benefit from a given compound or therapeutic agent. In some embodiments, the companion diagnostic is used to identify a subject having an increased risk of adverse side effects from administration of a therapeutic agent, compared to a reference standard. In some embodiments, the companion diagnostic is an in-vitro diagnostic or imaging tool selected from the list of FDA cleared or approved companion diagnostic devices. In some embodiments, the companion diagnostic is selected from the list of tests that have been cleared or approved by the Center for Devices and Radiological Health.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating BET proteins in tissue samples, including human, and for identifying BET protein ligands by inhibition binding of a labeled compound. Accordingly, the present invention includes BET protein assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro BET protein labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a BET protein by monitoring its concentration variation when contacting with the BET protein, through tracking of the labeling. For example, a test compound (labeled) can be evaluated for its ability to reduce binding of another compound which is known to bind to a BET protein (i.e., standard compound). Accordingly, the ability of a test compound to compete with the standard compound for binding to the BET protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more BET proteins as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm, 2.1×5.0 mm, Buffers: mobile phase A: 0.025% TFA in water and mobile phase B: 0.025% TFA in acetonitrile; gradient 2% to 80% ofB in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 μm, 19×100 mm column, eluting with mobile phase A: 0.15% $NH_4OH$ in water and mobile phase B: 0.15% $NH_4OH$ in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1

5-(2,4-Difluorophenoxy)-6-(6-methyl-7-oxo-6,7-dihydro-1H-pyrrolo[2,3-c]pyridin-4-yl)-1,3-dihydro-2H-benzimidazol-2-one

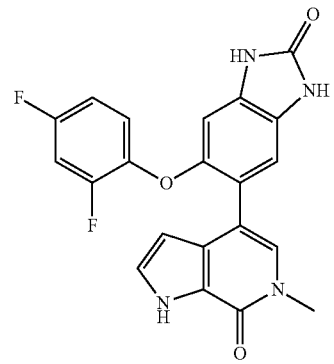 [SMILES: Cn1cc(-c2cc3[nH]c(=O)[nH]c3cc2Oc2ccc(F)cc2F)c2cc[nH]c2c1=O]

Step 1.
4-Bromo-5-(2,4-difluorophenoxy)-2-nitroaniline

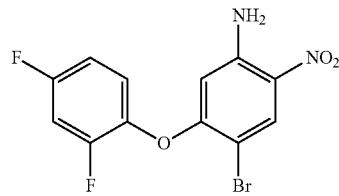 [SMILES: Nc1cc(Oc2ccc(F)cc2F)c(Br)cc1[N+](=O)[O-]]

A solution of 4-bromo-5-fluoro-2-nitroaniline (1.08 g, 4.60 mmol) [Combi-Blocks, AN-1501] and cesium carbonate (1.80 g, 5.52 mmol) in dimethyl sulfoxide (5.0 mL) was treated with 2,4-difluorophenol (0.90 mL, 5.53 mmol) [Acros Organics, 24320] and stirred at 80° C. for 30 min. The reaction mixture was diluted with ethyl acetate and water. The organic layer was separated and washed with water and brine, dried with magnesium sulfate, filtered, and concentrated to give the desired product (1.50 g, 95%) as a yellow solid that was used without further purification. LCMS calculated for $C_{12}H_8BrF_2N_2O_3$ (M+H)$^+$: m/z=345.0, 347.0. found: 345.0, 346.9.

Step 2.
4-Bromo-5-(2,4-difluorophenoxy)benzene-1,2-diamine

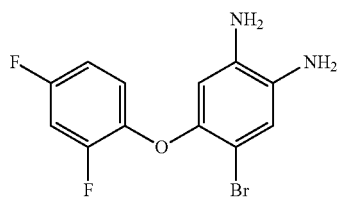 [SMILES: Nc1cc(Br)c(Oc2ccc(F)cc2F)cc1N]

A suspension of 4-bromo-5-(2,4-difluorophenoxy)-2-nitroaniline (0.406 g, 1.18 mmol) in tetrahydrofuran (5.0 mL) was treated with iron (0.657 g, 11.8 mmol), followed by acetic acid (4.9 mL, 87 mmol) and stirred at 60° C. for 1 h. The reaction mixture was diluted with ethyl acetate and quenched carefully with saturated sodium bicarbonate. The organic layer was separated and washed again with saturated sodium bicarbonate and brine, dried with magnesium sulfate, filtered, and concentrated to give the desired product (371 mg, quantitative) that was used immediately without further purification. LCMS calculated for $C_{12}H_{10}BrF_2N_2O$ (M+H)$^+$: m/z=315.0, 317.0. found: 315.0, 316.9.

Step 3. 5-Bromo-6-(2,4-difluorophenoxy)-1,3-dihydro-2H-benzimidazol-2-one

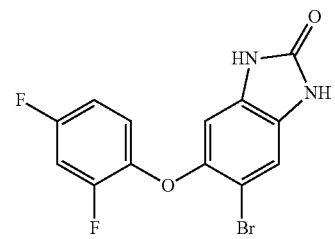 [SMILES: O=c1[nH]c2cc(Br)c(Oc3ccc(F)cc3F)cc2[nH]1]

A solution of 4-bromo-5-(2,4-difluorophenoxy)benzene-1,2-diamine (0.371 g, 1.18 mmol) in ethyl acetate (5.20 mL) was treated with N,N-carbonyldiimidazole (0.23 g, 1.4 mmol) and stirred at 50° C. for 30 min. The reaction mixture was treated with additional N,N-carbonyldiimidazole (1.2 eq) and stirred at 50° C. for 1 h. The reaction mixture was cooled to 20° C. and the heterogeneous mixture was filtered to give the desired product (156 mg, 39%) as a light grey solid. LCMS calculated for $C_{13}H_8BrF_2N_2O_2$ (M+H)$^+$: m/z=341.0, 343.0. found: 341.0, 342.9.

Step 4. 5-(2,4-Difluorophenoxy)-6-{6-methyl-1-[(4-methylphenyl)sulfonyl]-7-oxo-6,7-dihydro-1H-pyrrolo[2,3-c]pyridin-4-yl}-1,3-dihydro-2H-benzimidazol-2-one

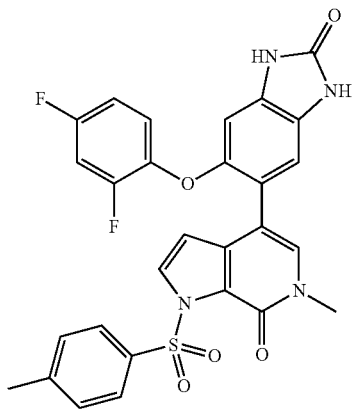

A suspension of 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (85.0 mg, 0.20 mmol), 5-bromo-6-(2,4-difluorophenoxy)-1,3-dihydro-2H-benzimidazol-2-one (74.5 mg, 0.218 mmol), potassium phosphate (0.10 g, 0.50 mmol), tris(dibenzylideneacetone) dipalladium (0) (5.0 mg, 0.006 mmol), and 1,3,5,7-tetramethyl-8-phenyl-2,4,6-trioxa-8-phosphatricyclo[3.3.1.13,7] decane (6.8 g, 0.0232 mmol) in 1,4-dioxane (2 mL) and water (0.4 mL) was degassed with nitrogen for 5 min and stirred at 80° C. for 1 h. The reaction mixture was diluted with ethyl acetate and water and filtered over celite. The organic layer was separated, washed with brine, dried with magnesium sulfate, filtered, and concentrated to give a crude residue. Purification via preparative LCMS (XBridge C18 column, eluting with a gradient of acetonitrile/water containing 0.1% trifluoroacetic acid, at flow rate of 60 mL/min) gave the desired product (24 mg, 18%) as an off-white foam. LCMS calculated for $C_{28}H_{21}F_2N_4O_5S$ (M+H)$^+$: m/z=563.1. found: 563.1.

Step 5. 5-(2,4-Difluorophenoxy)-6-(6-methyl-7-oxo-6,7-dihydro-1H-pyrrolo[2,3-c]pyridin-4-yl)-1,3-dihydro-2H-benzimidazol-2-one A solution of 5-(2,4-difluorophenoxy)-6-{6-methyl-1-[(4-methylphenyl)sulfonyl]-7-oxo-6,7-dihydro-1H-pyrrolo[2,3-c]pyridin-4-yl}-1,3-dihydro-2H-benzimidazol-2-one (0.024 g, 0.035 mmol) in ethanol (0.4 mL, 7 mmol) was treated with 1.0 M sodium hydroxide in water (0.18 mL, 0.18 mmol) and stirred at 80° C. for 30 min. Purification via preparative LCMS (XBridge C18 column, eluting with a gradient of acetonitrile/water 0.1% ammonium hydroxide, at flow rate of 30 mL/min) gave the desired product (3 mg, 20%). $^1$H NMR (500 MHz, DMSO-$d_6$) δ 11.93 (br s, 1H), 10.62 (br s, 2H), 7.34-7.26 (m, 1H), 7.22 (d, J=2.8 Hz, 1H), 7.17 (s, 1H), 7.02-6.87 (m, 3H), 6.52 (s, 1H), 6.17 (d, J=2.7 Hz, 1H), 3.50 (s, 3H); LCMS calculated for $C_{21}H_{15}F_2N_4O_3$ (M+H)$^+$: m/z=409.1. found: 409.1.

Example 2

6-(2,4-Difluorophenoxy)-1-methyl-5-(6-methyl-7-oxo-6,7-dihydro-1H-pyrrolo[2,3-c]pyridin-4-yl)-1,3-dihydro-2H-benzimidazol-2-one

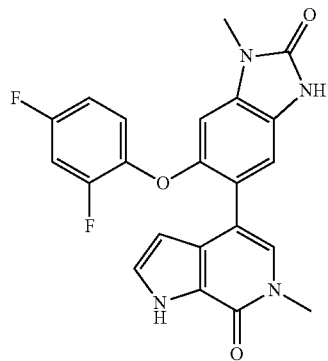 [SMILES: Cn1cc(-c2cc3[nH]c(=O)n(C)c3cc2Oc2ccc(F)cc2F)c2cc[nH]c2c1=O]

Step 1. N-[4-Bromo-5-(2,4-difluorophenoxy)-2-nitrophenyl]-2, 2, 2-trifluoroacetamide

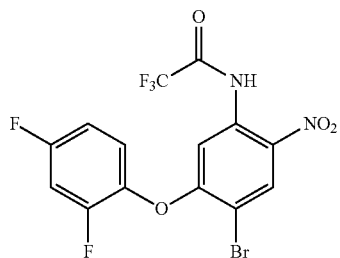 [SMILES: O=C(Nc1cc(Oc2ccc(F)cc2F)c(Br)cc1[N+](=O)[O-])C(F)(F)F]

A suspension of 4-bromo-5-(2,4-difluorophenoxy)-2-nitroaniline (0.500 g, 1.45 mmol) and triethylamine (0.404 mL, 2.90 mmol) in methylene chloride (7.0 mL) at 0° C. was treated with trifluoroacetic anhydride (0.409 mL, 2.90 mmol) dropwise. The reaction mixture was stirred at rt for 30 min, diluted with water (50 mL) and was extracted with dichloromethane (2×50 mL). The combined organic extracts were washed with brine, dried with sodium sulfate, filtered, and concentrated to give a light brown solid. Purification by flash column chromatography (100% hexanes to 20% EtOAc/hexanes) gave the desired product (0.637 g, 100%) as a yellow solid. LCMS calculated for $C_{14}H_7BrF_5N_2O_4$ (M+H)$^+$: m/z=440.9, 442.9. found: 440.6, 442.7.

Step 2. 4-Bromo-5-(2,4-difluorophenoxy)-N-methyl-2-nitroaniline

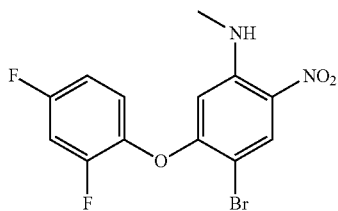 [SMILES: CNc1cc(Oc2ccc(F)cc2F)c(Br)cc1[N+](=O)[O-]]

A solution of N-[4-bromo-5-(2,4-difluorophenoxy)-2-nitrophenyl]-2,2,2-trifluoroacetamide (0.620 g, 1.40 mmol) in N,N-dimethylformamide (4.2 mL) was treated with cesium carbonate (1.37 g, 4.22 mmol) and methyl iodide (0.219 mL, 3.51 mmol) and stirred at 60° C. for 12 h. The reaction mixture was diluted with ethyl acetate (100 mL) and washed with water (75 mL) and brine, dried with sodium sulfate, filtered, and concentrated to give the intermediate methyl trifluoroacetamide which was used immediately without further purification. The intermediate methyl trifluoroacetamide was dissolved in tetrahydrofuran (11.8 mL) and methanol (2.8 mL), treated with 1.0 M sodium hydroxide in water (4.22 mL, 4.22 mmol), and stirred at 60° C. for 15 min. The reaction mixture was concentrated to remove THF and MeOH, diluted with ethyl acetate (100 mL) and washed with water (75 ml) and brine, dried with sodium sulfate, filtered, and concentrated to give a yellow solid. Purification by flash column chromatography (100% hexanes to 30% EtOAc/hexanes) gave the desired product (0.414 g, 82%) as a yellow solid. LCMS calculated for $C_{13}H_{10}BrF_2N_2O_3$ (M+H)$^+$: m/z=359.0, 361.0. found: 358.8, 360.8.

Step 3. 4-[2-(2,4-difluorophenoxy)-4-(methylamino)-5-nitrophenyl]-6-methyl-1-[(4-methylphenyl)sulfonyl]-1,6-dihydro-7H-pyrrolo[2,3-c]pyridin-7-one

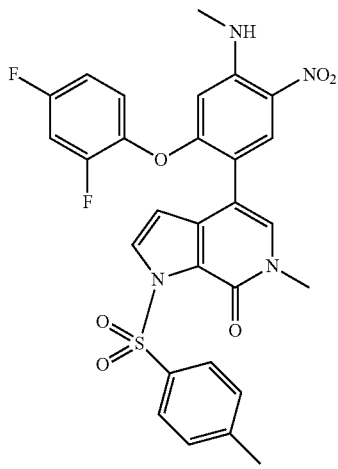 [SMILES: CNc1cc(Oc2ccc(F)cc2F)c(-c2cn(C)c(=O)c3c2ccn3S(=O)(=O)c2ccc(C)cc2)cc1[N+](=O)[O-]]

This compound was synthesized according to the procedure of Example 1, step 4, using 4-bromo-5-(2,4-difluorophenoxy)-N-methyl-2-nitroaniline instead of 5-bromo-6-(2,4-difluorophenoxy)-1,3-dihydro-2H-benzimidazol-2-one. LCMS calculated for $C_{28}H_{23}F_2N_4O_6S$ (M+H)$^+$: m/z=581.1. found: 580.9.

Step 4. 4-(5-amino-2-(2,4-difluorophenoxy)-4-(methylamino)phenyl)-6-methyl-1-tosyl-1H-pyrrolo[2,3-c]pyridin-7(6H)-one

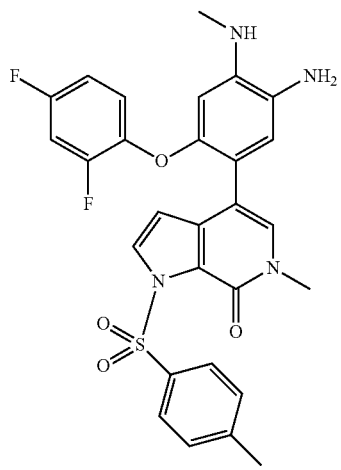 [SMILES: CNc1cc(Oc2ccc(F)cc2F)c(-c2cn(C)c(=O)c3c2ccn3S(=O)(=O)c2ccc(C)cc2)cc1N]

A solution of 4-[2-(2,4-difluorophenoxy)-4-(methylamino)-5-nitrophenyl]-6-methyl-1-[(4-methylphenyl)sulfonyl]-1,6-dihydro-7H-pyrrolo[2,3-c]pyridin-7-one (0.150 g, 0.258 mmol) in ethyl acetate (1.0 mL) was treated with methanol (1.0 mL) and saturated aqueous ammonium chloride solution (0.225 mL, 3.36 mmol) and cooled to 0° C. The reaction mixture was treated with zinc (0.135 g, 2.07 mmol) in two portions over 5 minutes. The reaction mixture was heated at 55° C. for 10 min, diluted with dichloromethane, filtered over Celite, and washed with dichloromethane. The filtrate was concentrated to residue. The residue was dissolved in dichloromethane (30 mL), washed with saturated sodium bicarbonate solution (20 mL), dried with sodium sulfate, filtered, and concentrated to give the desired product (0.141 g, 99%), which was used without further purification. LCMS calculated for $C_{28}H_{25}F_2N_4O_4S$ (M+H)$^+$: m/z=551.2. found: 550.9.

Step 5. 6-(2,4-Difluorophenoxy)-1-methyl-5-{6-methyl-1-[(4-methylphenyl)sulfonyl]-7-oxo-6,7-dihydro-1H-pyrrolo[2,3-c]pyridin-4-yl}-1,3-dihydro-2H-benzimidazol-2-one

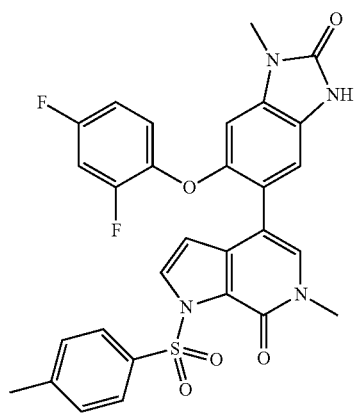

This compound was synthesized according to the procedure of Example 1, step 3, using 4-[5-amino-2-(2,4-difluorophenoxy)-4-(methylamino)phenyl]-6-methyl-1-[(4-methylphenyl)sulfonyl]-1,6-dihydro-7H-pyrrolo[2,3-c]pyridin-7-one instead of 4-bromo-5-(2,4-difluorophenoxy)benzene-1,2-diamine. LCMS calculated for $C_{29}H_{23}F_2N_4O_5S$ (M+H)$^+$: m/z=577.1. found: 576.9.

Step 6. 6-(2,4-Difluorophenoxy)-1-methyl-5-(6-methyl-7-oxo-6,7-dihydro-1H-pyrrolo[2,3-c]pyridin-4-yl)-1,3-dihydro-2H-benzimidazol-2-one This compound was synthesized according to the procedure of Example 1, Step 5, using 6-(2,4-difluorophenoxy)-1-methyl-5-{6-methyl-1-[(4-methylphenyl)sulfonyl]-7-oxo-6,7-dihydro-1H-pyrrolo[2,3-c]pyridin-4-yl}-1,3-dihydro-2H-benzimidazol-2-one instead of 5-(2,4-difluorophenoxy)-6-{6-methyl-1-[(4-methylphenyl)sulfonyl]-7-oxo-6,7-dihydro-1H-pyrrolo[2,3-c]pyridin-4-yl}-1,3-dihydro-2H-benzimidazol-2-one trifluoroacetate. $^1$H NMR (400 MHz, DMSO-d$_6$) δ 11.97 (s, 1H), 10.93 (s, 1H), 7.31-7.24 (m, 1H), 7.22 (dd, J=2.8, 2.8 Hz, 1H), 7.18 (s, 1H), 7.01 (s, 1H), 6.93-6.81 (m, 3H), 6.19-6.12 (m, 1H), 3.49 (s, 3H), 3.24 (s, 3H); LCMS calculated for $C_{22}H_{17}F_2N_4O_3$(M+H)$^+$: m/z=423.1. found: 423.0.

Example 3

4-[6-(2,4-Difluorophenoxy)-1-methyl-1H-benzimidazol-5-yl]-6-methyl-1,6-dihydro-7H-pyrrolo[2,3-c]pyridin-7-one

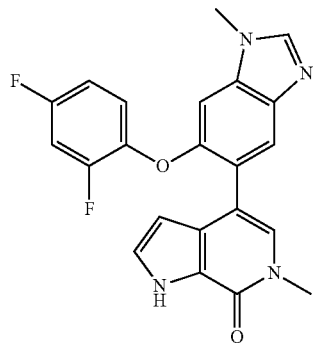 [SMILES: Cn1cc(-c2cc3ncn(C)c3cc2Oc2ccc(F)cc2F)c2cc[nH]c2c1=O]

A suspension of 4-[5-amino-2-(2,4-difluorophenoxy)-4-(methylamino)phenyl]-6-methyl-1-[(4-methylphenyl)sulfonyl]-1,6-dihydro-7H-pyrrolo[2,3-c]pyridin-7-one (0.045 g, 0.082 mmol) in tetrahydrofuran (0.80 mL) was treated with ethyl orthoformate (0.041 mL, 0.245 mmol) and p-toluenesulfonic acid monohydrate (1.6 mg, 8.2 μmol) and at 50° C. for 1 h. The reaction mixture was concentrated to give a residue. This residue was diluted with ethyl acetate (30 mL), washed with saturated sodium bicarbonate solution (20 mL), dried with sodium sulfate, filtered, and concentrated to give the intermediate benzimidazole which was used immediately without further purification. The intermediate benzimidazole was dissolved in ethanol (1.00 mL), treated with 1.0 M sodium hydroxide in water (0.327 mL, 0.327 mmol), and heated at 80° C. for 1 h. The reaction mixture was purified via preparative LCMS (XBridge C18 column, eluting with a gradient of acetonitrile/water 0.1% ammonium hydroxide, at flow rate of 30 mL/min) to give the desired product (19.5 mg, 59%). $^1$H NMR (300 MHz, DMSO-d$_6$) δ

11.97 (br s, 1H), 8.19 (s, 1H), 7.68 (s, 1H), 7.40-7.28 (m, 1H), 7.26-7.21 (m, 2H), 7.17 (s, 1H), 7.08-6.88 (m, 2H), 6.24-6.10 (m, 1H), 3.77 (s, 3H), 3.52 (s, 3H); LCMS calculated for $C_{22}H_{17}F_2N_4O_2$ (M+H)$^+$: m/z=407.1. found: 407.1.

Example 4

4-[6-(2,4-Difluorophenoxy)-1,2-dimethyl-1H-benzimidazol-5-yl]-6-methyl-1,6-dihydro-7H-pyrrolo[2,3-c]pyridin-7-one

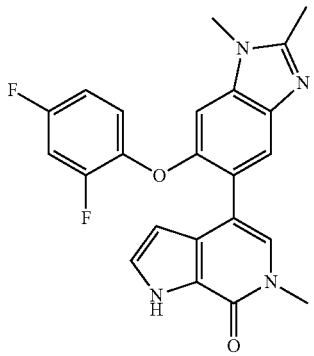 [SMILES: Cc1nc2cc(-c3cn(C)c(=O)c4[nH]ccc34)c(Oc3ccc(F)cc3F)cc2n1C]

This compound was synthesized according to the procedure of Example 3 using triethyl orthoacetate instead of ethyl orthoformate. $^1$H NMR (300 MHz, DMSO-d$_6$) δ 11.96 (br s, 1H), 7.54 (s, 1H), 7.37-7.26 (m, 1H), 7.24-7.21 (m, 1H), 7.19 (s, 1H), 7.16 (s, 1H), 6.96-6.84 (m, 2H), 6.20-6.09 (m, 1H), 3.67 (s, 3H), 3.51 (s, 3H), 2.51 (s, 3H); LCMS calculated for $C_{23}H_{19}F_2N_4O_2$(M+H)$^+$: m/z=421.1. found: 421.1.

Example 5

4-[5-(2,4-Difluorophenoxy)-1H-benzimidazol-6-yl]-6-methyl-1,6-dihydro-7H-pyrrolo[2,3-c]pyridin-7-one trifluoroacetate

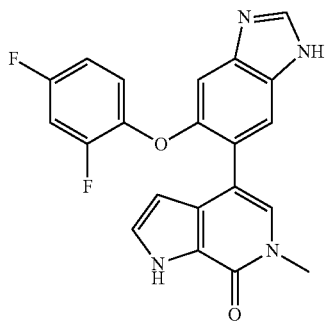 [SMILES: Cn1cc(-c2cc3[nH]cnc3cc2Oc2ccc(F)cc2F)c2cc[nH]c2c1=O]

Step 1. 4-[4,5-Diamino-2-(2,4-difluorophenoxy)phenyl]-6-methyl-1-[(4-methylphenyl)sulfonyl]-1,6-dihydro-7H-pyrrolo[2,3-c]pyridin-7-one

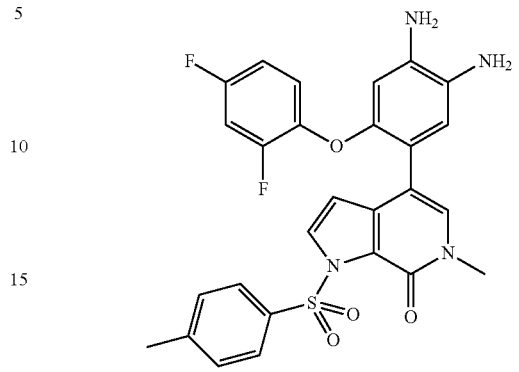

This compound was synthesized according to the procedure of Example 1, Step 4, using 4-bromo-5-(2,4-difluorophenoxy)benzene-1,2-diamine instead of 5-bromo-6-(2,4-difluorophenoxy)-1,3-dihydro-2H-benzimidazol-2-one. LCMS calculated for $C_{27}H_{23}F_2N_4O_4S$ (M+H)$^+$: m/z=537.1. found: 537.1.

Step 2. 4-[5-(2,4-Difluorophenoxy)-1H-benzimidazol-6-yl]-6-methyl-1,6-dihydro-7H-pyrrolo[2,3-c]pyridin-7-one trifluoroacetate This compound was synthesized according to the procedure of Example 3, using 4-[4,5-diamino-2-(2,4-difluorophenoxy)phenyl]-6-methyl-1-[(4-methylphenyl)sulfonyl]-1,6-dihydro-7H-pyrrolo[2,3-c]pyridin-7-one instead of 4-[5-amino-2-(2,4-difluorophenoxy)-4-(methylamino)phenyl]-6-methyl-1-[(4-methylphenyl)sulfonyl]-1,6-dihydro-7H-pyrrolo[2,3-c]pyridin-7-one. $^1$H NMR (500 MHz, DMSO-d$_6$) δ 12.01 (s, 1H), 8.99 (br s, 1H), 7.79 (s, 1H), 7.49-7.36 (m, 1H), 7.30 (s, 1H), 7.28-7.24 (m, 1H), 7.22-7.12 (m, 2H), 7.08-6.99 (m, 1H), 6.28-6.16 (m, 1H), 3.55 (s, 3H); LCMS calculated for $C_{21}H_{15}F_2N_4O_2$(M+H)$^+$: m/z=393.1. found: 393.1.

Example 6

4-[5-(2,4-Difluorophenoxy)-2-methyl-1H-benzimidazol-6-yl]-6-methyl-1,6-dihydro-7H-pyrrolo[2,3-c]pyridin-7-one trifluoroacetate

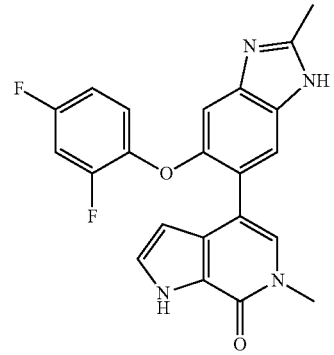 [SMILES: Cc1nc2cc(Oc3ccc(F)cc3F)c(-c3cn(C)c(=O)c4[nH]ccc34)cc2[nH]1]

This compound was synthesized according to the procedure of Example 3, using 4-[4,5-diamino-2-(2,4-difluorophenoxy)phenyl]-6-methyl-1-[(4-methylphenyl)sulfonyl]-1,6-dihydro-7H-pyrrolo[2,3-c]pyridin-7-one and triethyl orthoacetate instead of 4-[5-amino-2-(2,4-difluorophenoxy)-4-(methylamino)phenyl]-6-methyl-1-[(4-methylphenyl)sulfonyl]-1,6-dihydro-7H-pyrrolo[2,3-c]pyridin-7-one and ethyl orthoformate. $^1$H NMR (500 MHz, DMSO-$d_6$) δ 12.02 (s, 1H), 7.75 (s, 1H), 7.46-7.35 (m, 1H), 7.29 (s, 1H), 7.27-7.24 (m, 1H), 7.18-7.09 (m, 2H), 7.07-7.00 (m, 1H), 6.22-6.13 (m, 1H), 3.54 (s, 3H), 2.71 (s, 3H); LCMS calculated for $C_{22}H_{17}F_2N_4O_2$(M+H)$^+$: m/z=407.1. found: 407.1.

Example 7

5-(2,4-Difluorophenoxy)-1,3-dimethyl-6-(6-methyl-7-oxo-6,7-dihydro-1H-pyrrolo[2,3-c]pyridin-4-yl)-1,3-dihydro-2H-benzimidazol-2-one

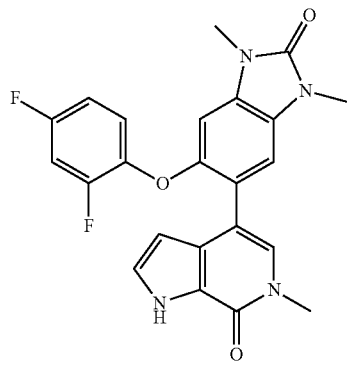 [SMILES: Cn1cc(-c2cc3c(cc2Oc2ccc(F)cc2F)n(C)c(=O)n3C)c2cc[nH]c2c1=O]

A solution of 6-(2,4-difluorophenoxy)-1-methyl-5-{6-methyl-1-[(4-methylphenyl)sulfonyl]-7-oxo-6,7-dihydro-1H-pyrrolo[2,3-c]pyridin-4-yl}-1,3-dihydro-2H-benzimidazol-2-one (50.4 mg, 0.0874 mmol) in N,N-dimethylformamide (0.415 mL) was treated with sodium hydride (7.0 mg, 0.175 mmol) and stirred rt for 30 min. The reaction mixture was treated with methyl iodide (8.2 μL, 0.131 mmol) and stirred for 1 h. The reaction mixture was quenched with saturated ammonium chloride (20 mL) and extracted with ethyl acetate (30 mL). The organic layer was separated, washed with brine, dried with sodium sulfate, filtered, and concentrated to give the intermediate dimethylurea which was used immediately without further purification. The intermediate dimethylurea was dissolved in ethanol (1.0 mL), treated with 1.0 M sodium hydroxide in water (0.350 mL, 0.350 mmol), and heated at 80° C. for 30 min. The reaction mixture was quenched with acetic acid (0.0224 mL, 0.393 mmol) and purified via preparative LCMS (XBridge C18 column, eluting with a gradient of acetonitrile/water containing 0.1% trifluoroacetic acid, at flow rate of 60 mL/min) to give the desired product which still contained an impurity. This material was re-purified via preparative LCMS (XBridge C18 column, eluting with a gradient of methanol/water containing 0.1% trifluoroacetic acid, at flow rate of 60 mL/min) to give the desired product (7.3 mg, 19%) as a white solid. $^1$H NMR (500 MHz, DMSO-$d_6$) δ 11.97 (s, 1H), 7.32-7.26 (m, 1H), 7.26-7.22 (m, 2H), 7.19 (s, 1H), 6.95 (s, 1H), 6.92-6.83 (m, 2H), 6.19 (s, 1H), 3.50 (s, 3H), 3.34 (s, 3H), 3.29 (s, 3H); LCMS calculated for $C_{23}H_{19}F_2N_4O_3$(M+H)$^+$: m/z=437.1. found: 437.1.

Example 8

4-(5-(2,4-difluorophenoxy)-1H-benzo[d][1,2,3]triazol-6-yl)-6-methyl-1H-pyrrolo[2,3-c]pyridin-7(6H)-one

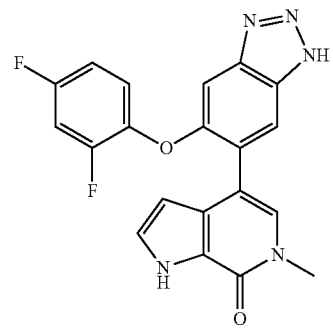 [SMILES: Cn1cc(-c2cc3[nH]nnc3cc2Oc2ccc(F)cc2F)c2cc[nH]c2c1=O]

Step 1. 6-Bromo-5-(2,4-difluorophenoxy)-1H-1,2,3-benzotriazole

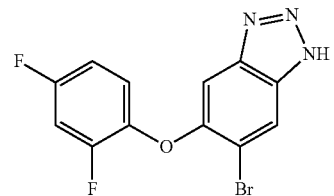 [SMILES: Fc1ccc(Oc2cc3nn[nH]c3cc2Br)c(F)c1]

A solution of 4-bromo-5-(2,4-difluorophenoxy)benzene-1,2-diamine (0.071 g, 0.22 mmol) in acetic acid (0.4 mL) was treated with water (1.1 mL) followed by sodium nitrite (0.078 g, 1.1 mmol) and stirred at 20° C. for 30 min. The reaction mixture was diluted with ethyl acetate and water. The organic layer was separated, washed with saturated sodium bicarbonate (2×) and brine, dried with magnesium sulfate, filtered, and concentrated to give a crude brown oil. Purification by flash column chromatography (100% hexanes to 60% EtOAc/hexanes) gave the desired product (57 mg, 78%) as a yellow solid. LCMS calculated for $C_{12}H_7BrF_2N_3O$ (M+H)$^+$: m/z=326.0, 328.0. found: 325.9, 327.9.

Step 2. 6-Bromo-5-(2,4-difluorophenoxy)-1-(tetrahydro-2H-pyran-2-yl)-1H-1,2,3-benzotriazole

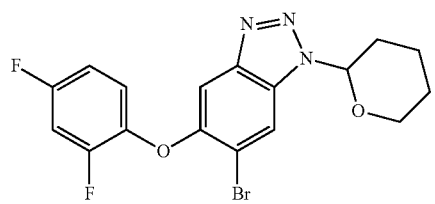 [SMILES: Fc1ccc(Oc2cc3nnn(C4CCCCO4)c3cc2Br)c(F)c1]

A solution of 6-bromo-5-(2,4-difluorophenoxy)-1H-1,2,3-benzotriazole (0.047 g, 0.14 mmol) and p-toluenesulfonic acid monohydrate (0.0027 g, 0.014 mmol) in chloroform (0.65 mL) was treated with dihydropyran (0.0197 mL, 0.216 mmol) and stirred at 60° C. for 1 h. The reaction mixture was diluted with dichloromethane and washed with saturated sodium bicarbonate. The aqueous layer was separated and re-extracted with dichloromethane. The combined organic layers were separated, washed with water and brine, dried with magnesium sulfate, filtered, and concentrated to a crude oil. Purification by flash column chromatography (100% hexanes to 60% EtOAc/hexanes) gave the desired product as a mixture of isomers that was used without further purification.

Step 3. 4-(5-(2,4-difluorophenoxy)-1-(tetrahydro-2H-pyran-2-yl)-1H-benzo[d][1,2,3]triazol-6-yl)-6-methyl-1-tosyl-1H-pyrrolo[2,3-c]pyridin-7(6H)-one

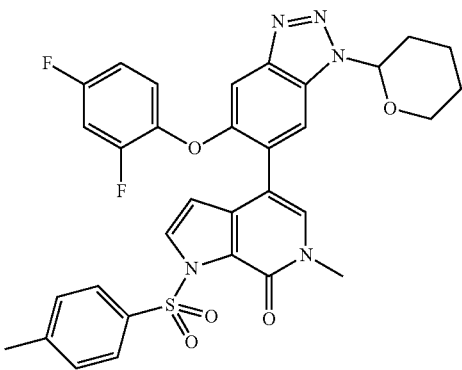 [SMILES: Cc1ccc(S(=O)(=O)n2ccc3c(-c4cc5c(cc4Oc4ccc(F)cc4F)nnn5C4CCCCO4)cn(C)c(=O)c32)cc1]

A solution of 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (0.0720 g, 0.168 mmol), 6-bromo-5-(2,4-difluorophenoxy)-1-(tetrahydro-2H-pyran-2-yl)-1H-1,2,3-benzotriazole (0.069 g, 0.17 mmol), 4-(di-tert-butylphosphino)-N,N-dimethylaniline-dichloropalladium (2:1) (1.8 mg, 0.00252 mmol), and cesium fluoride (0.0894 g, 0.589 mmol) in 1-butanol (0.765 mL) and water (0.18 mL) was degassed with nitrogen for 5 min and stirred at 110° C. for 1 h. The reaction mixture was diluted with ethyl acetate and water. The organic layer was separated and washed with brine, dried with magnesium sulfate, filtered, and concentrated to give a crude residue. Purification by flash column chromatography (100% hexanes to 80% EtOAc/hexanes) gave the desired product (77 mg, 72%) as a yellow solid that was not entirely pure. This material was used without further purification. LCMS calculated for $C_{32}H_{28}F_2N_5O_5S$ (M+H)$^+$: m/z=632.2. found: 632.1.

Step 4. 4-[5-(2,4-Difluorophenoxy)-1H-1,2,3-benzotriazol-6-yl]-6-methyl-1-[(4-methylphenyl)sulfonyl]-1,6-dihydro-7H-pyrrolo[2,3-c]pyridin-7-one

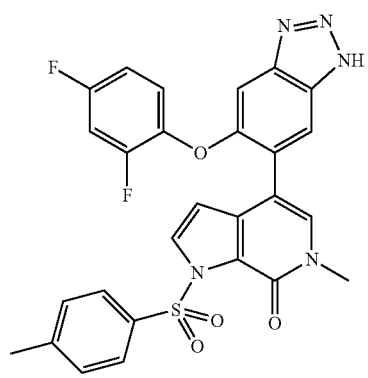

A solution of 4-[5-(2,4-difluorophenoxy)-1-(tetrahydro-2H-pyran-2-yl)-1H-1,2,3-benzotriazol-6-yl]-6-methyl-1-[(4-methylphenyl)sulfonyl]-1,6-dihydro-7H-pyrrolo[2,3-c]pyridin-7-one (0.077 g, 0.12 mmol) in methanol (0.34 mL) was treated with 6.0 M hydrogen chloride in water (0.102 mL, 0.610 mmol) and stirred at 20° C. for 22 h. The reaction mixture was concentrated to give a crude residue that was used immediately without further purification.

Step 5. 4-(5-(2,4-difluorophenoxy)-1H-benzo[d][1,2,3]triazol-6-yl)-6-methyl-1H-pyrrolo[2,3-c]pyridin-7(6H)-one A solution of 4-[5-(2,4-difluorophenoxy)-1H-1,2,3-benzotriazol-6-yl]-6-methyl-1-[(4-methylphenyl)sulfonyl]-1,6-dihydro-7H-pyrrolo[2,3-c]pyridin-7-one (67 mg, 0.12 mmol) in ethanol (7.1 mL) was treated with 3.0 M sodium hydroxide in water (408 µL, 1.22 mmol) and stirred at 20° C. overnight. Purification via preparative LCMS (XBridge C18 column, eluting with a gradient of acetonitrile/water containing 0.1% trifluoroacetic acid, at flow rate of 60 mL/min) gave the desired product (21 mg, 34%). $^1$H NMR (400 MHz, DMSO-$d_6$) δ 12.06 (s, 1H), 8.01 (br s, 1H), 7.53-7.41 (m, 1H), 7.36 (s, 1H), 7.33-7.21 (m, 2H), 7.16-6.98 (m, 2H), 6.24 (d, J=2.0 Hz, 1H), 3.56 (s, 3H); LCMS calculated for $C_{20}H_{14}F_2N_5O_2$ (M+H)$^+$: m/z=394.1. found: 394.1.

Example 9

4-[6-(2,4-Difluorophenoxy)-1H-benzimidazol-5-yl]-6-methyl-1,6-dihydro-7H-pyrazolo[3,4-c]pyridin-7-one trifluoroacetate

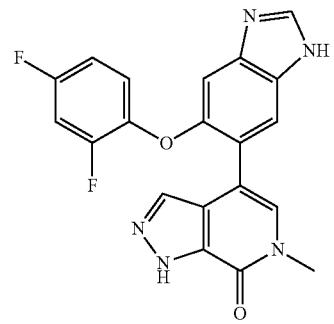 [SMILES: Cn1cc(-c2cc3[nH]cnc3cc2Oc2ccc(F)cc2F)c2cn[nH]c2c1=O]

Step 1.
5-Bromo-1,4-dimethyl-3-nitropyridin-2(1H)-one

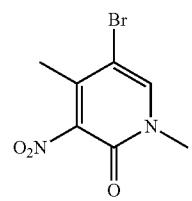

A solution of 5-bromo-4-methyl-3-nitropyridin-2-ol (15.00 g, 64.37 mmol) [Combi-Blocks, AN-1086] in N,N-dimethylformamide (250 mL) was treated with sodium hydride (3.09 g, 77.3 mmol) (60% dispersion on mineral oil) slowly and portionwise, and stirred at RT for 30 min. The reaction mixture was treated with methyl iodide (4.81 mL, 77.2 mmol) dropwise and stirred at RT for 3 h. LCMS indicated a clean peak for methylated product. The reaction mixture was poured over water/ice (~400 mL) and allowed to stir while the ice melted. The aqueous mixture was extracted with EA. The organic layer was washed with water (3×) and brine, dried with magnesium sulfate, filtered, and concentrated to give the desired product (14.9 g, 93%) that was used without further purification. LCMS calculated for $C_7H_8BrN_2O_3$ (M+H)$^+$: m/z=247.0, 249.0. found: 247.0, 248.9.

Step 2. 4-Bromo-6-methyl-1,6-dihydro-7H-pyrazolo [3,4-c]pyridin-7-one

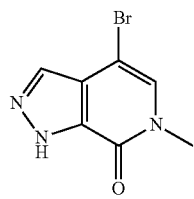

A solution of 3-amino-5-bromo-1,4-dimethylpyridin-2 (1H)-one (12.1 g, 55.9 mmol) in toluene (300 mL) was treated with acetic anhydride (15.8 mL, 168 mmol) followed by potassium acetate (6.58 g, 67.1 mmol) and stirred at RT overnight. The reaction mixture was treated with amyl nitrite (11.3 mL, 83.8 mmol) and heated at 80° C. overnight. The reaction mixture was diluted with ethyl acetate, washed with water and brine, dried with magnesium sulfate, filtered, and concentrated to give a mixture of the desired product along with the acetylated desired product. This mixture was diluted with methanol (490 mL) and treated with 1.0 M sodium hydroxide in water (280 mL) and stirred at RT for 1 h. The reaction mixture was diluted with ethyl acetate, washed with water and brine, dried with magnesium sulfate, filtered, and concentrated to give crude product. Purification by flash column chromatography (100% hexanes to 100% EtOAc) gave the desired product (8.4 g, 66%). LCMS calculated for $C_7H_7BrN_3O$ (M+H)$^+$: m/z=228.0, 230.0. found: 227.9, 229.9.

Step 3. 4-Bromo-6-methyl-1-{[2-(trimethylsilyl) ethoxy]methyl}-1,6-dihydro-7H-pyrazolo[3,4-c] pyridin-7-one and 4-bromo-6-methyl-2-{[2-(trimethylsilyl)ethoxy]methyl}-2,6-dihydro-7H-pyrazolo [3,4-c]pyridin-7-one

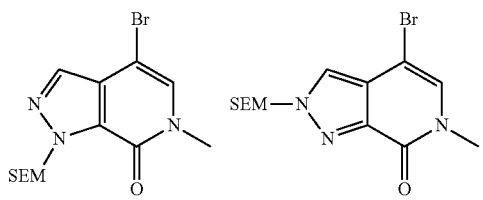 [SMILES: Cn1cc(Br)c2cnn(COCC[Si](C)(C)C)c2c1=O ; Cn1cc(Br)c2cn(COCC[Si](C)(C)C)nc2c1=O]

A solution of 4-bromo-6-methyl-1,6-dihydro-7H-pyrazolo[3,4-c]pyridin-7-one (5.40 g, 23.7 mmol) in N,N-dimethylformamide (170 mL) at 0° C. was treated with sodium hydride (1.42 g, 35.5 mmol) and stirred at 0° C. for 30 min. The reaction mixture was treated with [β-(trimethylsilyl) ethoxy]methyl chloride (7.90 g, 47.4 mmol) and stirred at 0° C. for 1 h. The reaction mixture was poured into ethyl acetate (200 mL) and washed with saturated sodium bicarbonate solution. The aqueous layer was separated and extracted with ethyl acetate (2×100 mL). The combined organic layers were washed with water (3×) and brine, dried with magnesium sulfate, filtered, and concentrated to give the crude product. Purification by flash column chromatography (100% hexanes to 100% EtOAc) gave a major product and a minor product (8.5 g total yield, quantitative) as a ~4:1 mixture of SEM-protected isomers. $^1$H NMR analysis of the individual products revealed the major isomer was consistent with the SEM group at the 1-position and the minor isomer was consistent with the SEM group at the 2-position. In practice, the isomers were not separated at this step and used as a mixture of isomers in the next step. LCMS calculated for $C_{13}H_{21}BrN_3O_2Si$ (M+H)$^+$: m/z=358.1, 360.1. found: 358.0, 360.0.

Step 4. 6-Methyl-4-(4,4,5,5-tetramethyl-1,3,2-dioxaborolan-2-yl)-1-{[2-(trimethylsilyl)ethoxy]methyl}-1,6-dihydro-7H-pyrazolo[3,4-c]pyridin-7-one and 6-methyl-4-(4,4,5,5-tetramethyl-1,3,2-dioxaborolan-2-yl)-2-{[2-(trimethylsilyl)ethoxy]methyl}-2,6-dihydro-7H-pyrazolo[3,4-c]pyridin-7-one

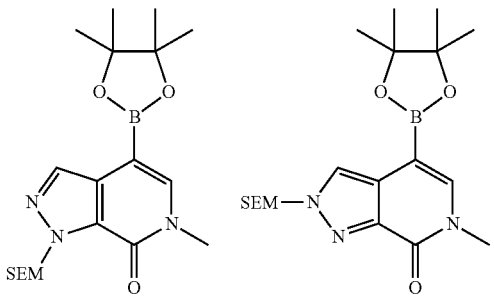 [SMILES: Cn1cc(B2OC(C)(C)C(C)(C)O2)c2cnn(COCC[Si](C)(C)C)c2c1=O ; Cn1cc(B2OC(C)(C)C(C)(C)O2)c2cn(COCC[Si](C)(C)C)nc2c1=O]

A suspension of 4-bromo-6-methyl-1-{[2-(trimethylsilyl) ethoxy]methyl}-1,6-dihydro-7H-pyrazolo[3,4-c]pyridin-7-one and 4-bromo-6-methyl-2-{[2-(trimethylsilyl)ethoxy] methyl}-2, 6-dihydro-7H-pyrazolo[3,4-c]pyridin-7-one (8.50 g, 23.7 mmol) (~4:1 mixture of isomers), 4,4, 5,5,4', 4',5',5'-octamethyl-[2,2']bi[[1,3,2]dioxaborolanyl](12.0 g, 47.5 mmol), dicyclohexyl(2',4', 6'-triisopropylbiphenyl-2-yl)phosphine (1.23 g, 2.58 mmol), potassium acetate (5.12 g, 52.2 mmol), and tris(dibenzylideneacetone)dipalladium(0) (543 mg, 0.592 mmol) in 1,4-dioxane (120 mL) was degassed with nitrogen for 10 min and stirred at 80° C. for 3 h. The reaction mixture was diluted with ethyl acetate (100 mL) and saturated sodium bicarbonate solution (100 mL), filtered over Celite, and washed with ethyl acetate. The aqueous layer was separated and re-extracted with ethyl acetate (100 mL). The combined organic layers were washed with brine, dried with magnesium sulfate, filtered, and concentrated to give a crude residue. Purification by flash column chromatography (100% hexanes to 60% EtOAc/ hexanes) gave the individual isomers of the desired product (major isomer: 5.23 g, 54%; minor isomer: 1.28 g, 13%). Major isomer (SEM at 1-position): LCMS calculated for $C_{19}H_{33}BN_3O_4Si$ (M+H)$^+$: m/z=406.2. found: 406.2; minor isomer (SEM at 2-position): LCMS calculated for $C_{19}H_{33}BN_3O_4Si$ (M+H)$^+$: m/z=406.2. found: 406.2.

Step 5.
6-Bromo-5-(2,4-difluorophenoxy)-1H-benzimidazole

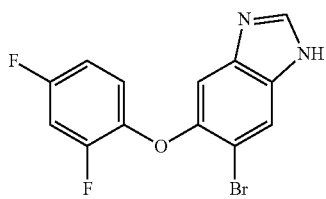 [SMILES: Fc1ccc(Oc2cc3nc[nH]c3cc2Br)c(F)c1]

A solution of 4-bromo-5-(2,4-difluorophenoxy)benzene-1,2-diamine (0.090 g, 0.28 mmol) in tetrahydrofuran (1.1 mL) was treated with ethyl orthoformate (0.142 mL, 0.857 mmol) followed by p-toluenesulfonic acid monohydrate (0.005 g, 0.03 mmol) and stirred at 50° C. for 1 h. The reaction mixture was concentrated and diluted with ethyl acetate and saturated sodium bicarbonate. The organic layer was separated and washed with brine, dried with magnesium sulfate, filtered, and concentrated to give a crude oil. Purification by flash column chromatography (100% hexanes to 100% EtOAc) gave the desired product (69 mg, 74%). LCMS calculated for $C_{13}H_8BrF_2N_2O$ (M+H)$^+$: m/z=325.0, 327.0. found: 325.0, 327.0.

Step 6. 6-Bromo-5-(2,4-difluorophenoxy)-1-(tetrahydro-2H-pyran-2-yl)-1H-benzimidazole and 5-bromo-6-(2,4-difluorophenoxy)-1-(tetrahydro-2H-pyran-2-yl)-1H-benzimidazole

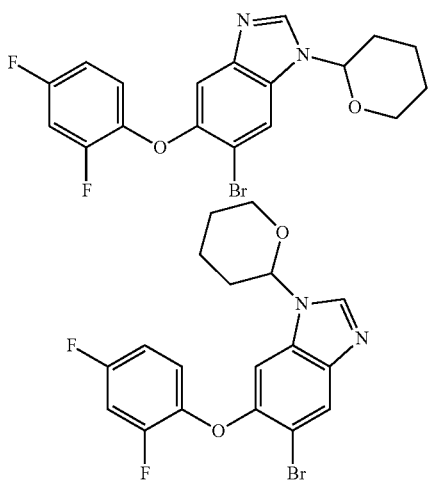

A solution of 6-bromo-5-(2,4-difluorophenoxy)-1H-benzimidazole (0.041 g, 0.13 mmol) and p-toluenesulfonic acid monohydrate (0.0024 g, 0.013 mmol) in chloroform (0.57 mL) was cooled to 0° C., treated with dihydropyran (0.0172 mL, 0.189 mmol), and stirred at 60° C. for 6 h. The reaction mixture was diluted with dichloromethane and washed with saturated sodium bicarbonate. The aqueous layer was separated and re-extracted with dichloromethane. The combined organic layers were separated, washed with water and brine, dried with magnesium sulfate, filtered, and concentrated to give a crude oil. Purification by flash column chromatography (100% hexanes to 50% EtOAc/hexanes) gave the desired product (35 mg, 68%) as a mixture of isomers. LCMS calculated for $C_{18}H_{16}BrF_2N_2O_2$ (M+H)$^+$: m/z=409.0, 411.0. found: 409.0, 411.0.

Step 7. 4-[6-(2,4-Difluorophenoxy)-1-(tetrahydro-2H-pyran-2-yl)-1H-benzimidazol-5-yl]-6-methyl-1-{[2-(trimethylsilyl)ethoxy]methyl}-1,6-dihydro-7H-pyrazolo[3,4-c]pyridin-7-one and 4-[5-(2,4-difluorophenoxy)-1-(tetrahydro-2H-pyran-2-yl)-1H-benzimidazol-6-yl]-6-methyl-1-{[2-(trimethylsilyl)ethoxy]methyl}-1,6-dihydro-7H-pyrazolo[3,4-c]pyridin-7-one

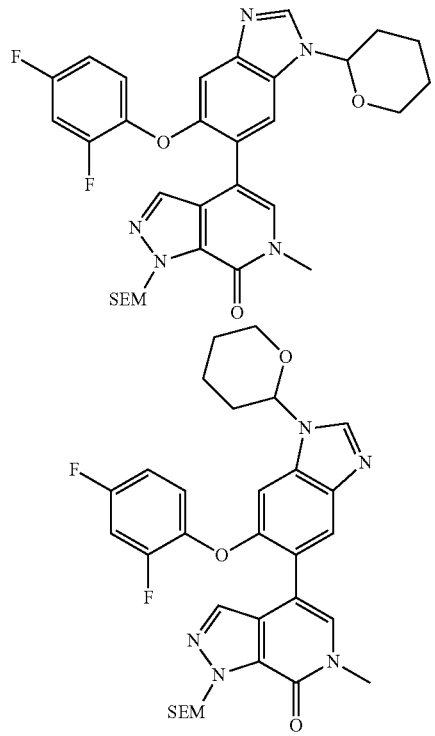

A suspension of 6-bromo-5-(2,4-difluorophenoxy)-1-(tetrahydro-2H-pyran-2-yl)-1H-benzimidazole and 5-bromo-6-(2,4-difluorophenoxy)-1-(tetrahydro-2H-pyran-2-yl)-1H-benzimidazole (0.0350 g, 0.0855 mmol) (mixture of isomers from step 6), cesium fluoride (0.0455 g, 0.299 mmol), and 6-methyl-4-(4,4,5,5-tetramethyl-1,3,2-dioxaborolan-2-yl)-1-{[2-(trimethylsilyl)ethoxy]methyl}-1,6-dihydro-7H-pyrazolo[3,4-c]pyridin-7-one (0.0381 g, 0.0941 mmol) in 1-butanol (0.39 mL) and water (0.091 mL) was degassed with nitrogen for 5 min, treated with 4-(di-tert-butylphosphino)-N,N-dimethylaniline-dichloropalladium (2:1) (0.908 mg, 0.00128 mmol), degassed with nitrogen for 5 min, and heated at 100° C. for 2 h. The reaction mixture was poured into ethyl acetate (35 mL), washed with water and brine, dried with sodium sulfate, filtered, and concentrated to a crude oil. Purification by flash column chromatography (100% hexanes to 30% ethyl acetate [containing 5% MeOH]/70% hexanes over 1 min and then 30% ethyl acetate [containing 5% MeOH]/70% hexanes to 100% ethyl acetate [containing 5% MeOH] over 30 min) gave the desired product (33 mg, 63%) as a mixture of isomers. LCMS calculated for $C_{31}H_{36}F_2N_5O_4Si$ (M+H)$^+$: m/z=608.2. found: 608.2.

Step 8. 4-[6-(2,4-Difluorophenoxy)-1H-benzimidazol-5-yl]-6-methyl-1,6-dihydro-7H-pyrazolo[3,4-c]pyridin-7-one trifluoroacetate A solution of 4-[6-(2,4-difluorophenoxy)-1-(tetrahydro-2H-pyran-2-yl)-1H-benzimidazol-5-yl]-6-methyl-1-{[2-(trimethylsilyl)ethoxy]methyl}-1,6-dihydro-7H-pyrazolo[3,4-c]pyridin-7-one (0.033 g, 0.054 mmol) and 4-[5-(2,4-difluorophenoxy)-1-(tetrahydro-2H-pyran-2-yl)-1H-benzimidazol-6-yl]-6-methyl-1-{[2-(trimethylsilyl)ethoxy]methyl}-1,6-dihydro-7H-pyrazolo[3,4-c]pyridin-7-one (0.033 g, 0.054 mmol) (mixture of isomers from step 7) in methanol (0.48 mL) was treated with 6.0 M hydrogen chloride in water (0.0905 mL, 0.543 mmol) and stirred at 60° C. for 4 h. The reaction mixture was cooled to 0° C., quenched with concentrated ammonium hydroxide, and purified via preparative LCMS (XBridge C18 column, eluting with a gradient of acetonitrile/water containing 0.1% trifluoroacetic acid, at flow rate of 60 mL/min) to give the desired product (16 mg, 59%) as a white solid. $^1$H NMR (400 MHz, DMSO-$d_6$) δ 9.18 (s, 1H), 7.86 (d, J=12.6 Hz, 2H), 7.52-7.44 (m, 1H), 7.43 (s, 1H), 7.36-7.27 (m, 1H), 7.17 (s, 1H), 7.14-7.06 (m, 1H), 3.58 (s, 3H); LCMS calculated for $C_{20}H_{14}F_2N_5O_2$ (M+H)$^+$: m/z=394.1. found: 394.1.

Example 10

4-[6-(2,4-Difluorophenoxy)-1,3-dimethyl-2-oxo-2,3-dihydro-1H-benzimidazol-5-yl]-6-methyl-1,6-dihydro-7H-pyrazolo[3,4-c]pyridin-7-one

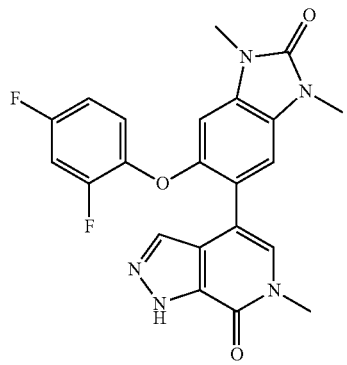 [SMILES: Cn1cc(-c2cc3c(cc2Oc2ccc(F)cc2F)n(C)c(=O)n3C)c2cn[nH]c2c1=O]

Step 1. 5-Bromo-6-(2,4-difluorophenoxy)-1,3-dimethyl-1,3-dihydro-2H-benzimidazol-2-one A solution of 5-bromo-6-(2,4-difluorophenoxy)-1,3-dihydro-2H-benzimidazol-2-one (0.106 g, 0.311 mmol) in N,N-dimethylformamide (2.2 mL) was treated with sodium hydride (0.0273 g, 0.684 mmol) and stirred at 20° C. for 30 min. The reaction mixture was treated with methyl iodide (0.0426 mL, 0.684 mmol) and stirred 20° C. for 30 min. The reaction mixture was diluted with water which resulted in the formation of a precipitate. The solid was filtered and washed with water to give the desired product (108 mg, 94%) which was used without further purification. LCMS calculated for $C_{15}H_{12}BrF_2N_2O_2$ (M+H)$^+$: m/z=369.0, 371.0. found: 368.9, 371.0.

Step 2. 4-[6-(2,4-Difluorophenoxy)-1,3-dimethyl-2-oxo-2,3-dihydro-1H-benzimidazol-5-yl]-6-methyl-1-{[2-(trimethylsilyl)ethoxy]methyl}-1,6-dihydro-7H-pyrazolo[3,4-c]pyridin-7-one

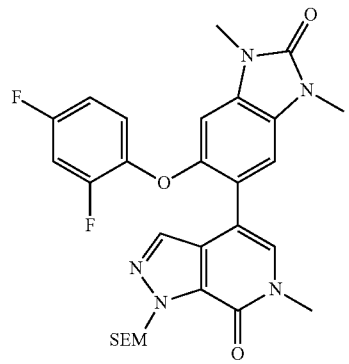 [SMILES: Cn1cc(-c2cc3c(cc2Oc2ccc(F)cc2F)n(C)c(=O)n3C)c2cnn(COCC[Si](C)(C)C)c2c1=O]

This compound was synthesized according to the procedure of Example 9, Step 7, using 5-bromo-6-(2,4-difluorophenoxy)-1,3-dimethyl-1,3-dihydro-2H-benzimidazol-2-one as the starting material. LCMS calculated for $C_{28}H_{32}F_2N_5O_4Si$ (M+H)$^+$: m/z=568.1. found: 568.1.

Step 3. 4-[6-(2,4-Difluorophenoxy)-1,3-dimethyl-2-oxo-2,3-dihydro-1H-benzimidazol-5-yl]-6-methyl-1,6-dihydro-7H-pyrazolo[3,4-c]pyridin-7-one This compound was synthesized according to the procedure of Example 9, Step 8, using 4-[6-(2,4-difluorophenoxy)-1,3-dimethyl-2-oxo-2,3-dihydro-1H-benzimidazol-5-yl]-6-methyl-1-{[2-(trimethylsilyl)ethoxy]methyl}-1,6-dihydro-7H-pyrazolo[3,4-c]pyridin-7-one as the starting material. $^1$H NMR (300 MHz, DMSO-$d_6$) δ 7.80 (s, 1H), 7.35-7.24 (m, 3H), 6.98 (s, 1H), 6.94-6.85 (m, 2H), 3.53 (s, 3H), 3.36 (s, 3H), 3.29 (s, 3H); LCMS calculated for $C_{22}H_{18}F_2N_5O_3$ (M+H)$^+$: m/z=438.1. found: 438.0.

Example 11

4-[5-(Cyclobutylmethoxy)-1H-benzimidazol-6-yl]-6-methyl-1,6-dihydro-7H-pyrrolo[2,3-c]pyridin-7-one

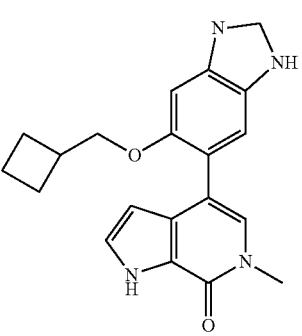 [SMILES: Cn1cc(-c2cc3c(cc2OCC2CCC2)NCN3)c2cc[nH]c2c1=O]

Step 1.
4-Bromo-5-(cyclobutylmethoxy)-2-nitroaniline

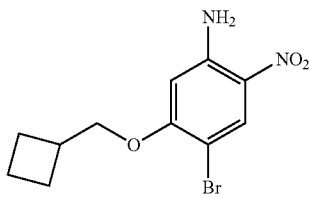 [SMILES: Nc1cc(OCC2CCC2)c(Br)cc1[N+](=O)[O-]]

Sodium hydride (0.82 g, 60% w/w, 20 mmol) was added at 0° C. to a solution of cyclobutylmethanol (1.8 mL, 20 mmol) in THF (40 mL). The 0° C. bath was removed, and the reaction mixture was stirred for 30 min. The reaction mixture was again cooled to 0° C. with an ice bath, and 4-bromo-5-fluoro-2-nitroaniline (2.5 g, 11 mmol) was added. The ice bath was removed, and the reaction mixture was stirred for 18 h at room temperature. The reaction was quenched with sat. $NH_4Cl$ and then diluted with $H_2O$. The aqueous solution was extracted with EtOAc (125 mL), and the organic layer was separated and washed with brine (100 mL). The resulting organic layer was dried over $MgSO_4$, filtered, and concentrated. Recrystallization from $CH_2Cl_2$/hexanes upon cooling at 0° C. overnight afforded the title compound as a red-brown solid (2.3 g, 72%). $^1$H NMR (300 MHz, $CDCl_3$) δ 8.28 (d, J=1.0 Hz, 1H), 6.07 (s, 1H), 3.90 (d, J=6.0 Hz, 2H), 2.88-2.61 (m, 1H), 2.09 2.25-2.00 (m, 2H), 2.01-1.71 (m, 4H). LCMS calculated for $C_{11}H_{14}BrN_2O_3(M+H)^+$: m/z=301.0, 303.0. found: 301.1, 303.1.

Step 2. 4-[4-Amino-2-(cyclobutylmethoxy)-5-nitrophenyl]-6-methyl-1-[(4-methylphenyl) sulfonyl]-1,6-dihydro-7H-pyrrolo[2,3-c]pyridin-7-one

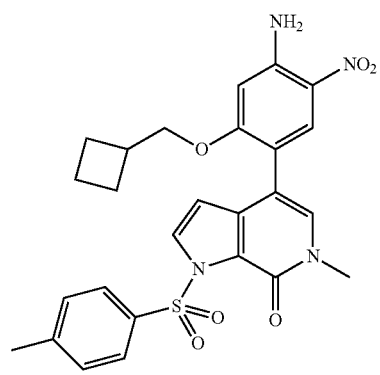 [SMILES: Cc1ccc(S(=O)(=O)n2ccc3c(-c4cc([N+](=O)[O-])c(N)cc4OCC4CCC4)cn(C)c(=O)c32)cc1]

A 1-dram vial was charged with 4-bromo-5-(cyclobutylmethoxy)-2-nitroaniline (35.7 mg, 0.118 mmol), cesium fluoride (64 mg, 0.42 mmol), 6-methyl-1-[(4-methylphenyl) sulfonyl]-4-(4,4,5,5-tetramethyl-1,3,2-dioxaborolan-2-yl)-1,6-dihydro-7H-pyrrolo[2,3-c]pyridin-7-one (50 mg, 0.12 mmol), 1-butanol (0.53 mL), and water (0.12 mL). The mixture was degassed with $N_2$ for 5 min. Then 4-(di-tert-butylphosphino)-N,N-dimethylaniline-dichloropalladium (2:1) (1.2 mg, 0.0017 mmol) was added and the solvent was again degassed for 5 min. The vial was capped, and the mixture was heated at 100° C. for 1.5 h. The reaction mixture was diluted with EtOAc (10 mL), and the resulting solution was washed successively with water (10 mL) and brine (10 mL). The resulting organic layer was dried over $Na_2SO_4$, filtered, and concentrated. The product was isolated via preparative HPLC on a C-18 column (pH 2, eluting with 51-71% 0.1% TFA (aq)/MeCN over 5 min, 60 mL/min). Fractions containing the title compound were combined and diluted with EtOAc. The resulting solution was washed twice with sat. $NaHCO_3$ and then once with brine. The organic layer was concentrated to give the title compound as a yellow-orange solid (21 mg, 21%). LCMS calculated for $C_{26}H_{27}N_4O_6S$ (M+H)$^+$: m/z=523.2. found: 523.1.

Step 3. 4-[5-(Cyclobutylmethoxy)-1H-benzimidazol-6-yl]-6-methyl-1,6-dihydro-7H-pyrrolo[2,3-c]pyridin-7-one To a suspension of 4-[4-amino-2-(cyclobutylmethoxy)-5-nitrophenyl]-6-methyl-1-[(4-methylphenyl)sulfonyl]-1,6-dihydro-7H-pyrrolo[2,3-c]pyridin-7-one (21 mg, 0.024 mmol) in 1:1 EtOAc/MeOH (0.840 mL) was added saturated solution of $NH_4Cl$ in water (0.0470 mL). The mixture was cooled to 0° C., followed by addition of zinc powder (26 mg, 0.40 mmol). The reaction mixture was allowed to warm to room temperature, and the suspension was subsequently heated at 55° C. for 1 h. The reaction mixture was diluted with $CH_2Cl_2$ and filtered through Celite. The filter cake was rinsed with $CH_2Cl_2$. The filtrate was then washed with saturated solution of $NaHCO_3$, dried over $Na_2SO_4$, filtered, and concentrated to provide the crude intermediate as a brown oil. The crude intermediate was then dissolved in THF (0.52 mL), followed by the addition of ethyl orthoformate (0.020 mL, 0.12 mmol) and p-toluenesulfonic acid monohydrate (1.2 mg, 0.0063 mmol). The mixture was heated at 55° C. for 1 h. The reaction mixture was then concentrated. The resulting residue was diluted with EtOAc (4 ml) and washed with saturated solution of $NaHCO_3$ (5 mL). The organic layer was separated, and the aqueous layer was extracted with EtOAc (2×4 mL). The combined organic layers were dried over $Na_2SO_4$, filtered, and concentrated to afford the crude intermediate as a tan solid. The crude intermediate from above was dissolved in ethanol (0.630 mL). 1.0 M solution of NaOH (aq) (0.376 mL, 0.376 mmol) was subsequently added, and the reaction mixture was heated at 55° C. for 4 h. The reaction mixture was diluted with MeOH, and the product was isolated via preparative HPLC on a C-18 column (pH 10, eluting with 23-43% 0.1% $NH_4OH$ (aq)/MeCN over 5 min, 60 mL/min) to give the title compound as a white solid (2.4 mg, 29%). $^1$H NMR (300

MHz, CD₃OD) δ 8.11 (s, 1H), 7.59 (br s, 1H), 7.31 (d, J=2.8 Hz, 1H), 7.24 (br s, 1H), 7.21 (s, 1H), 6.22 (d, J=2.8 Hz, 1H), 3.93 (d, J=5.9 Hz, 2H), 3.71 (s, 3H), 2.71-2.51 (m, 1H), 2.00-1.59 (m, 6H). LCMS calculated for $C_{20}H_{21}N_4O_2$ (M+H)⁺: m/z=349.2. found: 349.1.

Examples 12 and 13

4-[5-(Cyclobutylmethoxy)-1-ethyl-1H-benzimidazol-6-yl]-6-methyl-1,6-dihydro-7H-pyrrolo[2,3-c]pyridin-7-one and 4-[6-(Cyclobutylmethoxy)-1-ethyl-1H-benzimidazol-5-yl]-6-methyl-1,6-dihydro-7H-pyrrolo[2,3-c]pyridin-7-one

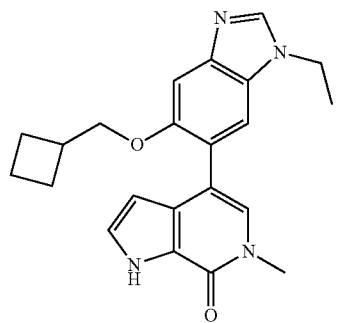

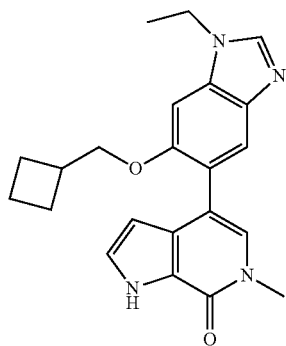

Step 1.
5-Bromo-6-(cyclobutylmethoxy)-1H-benzimidazole

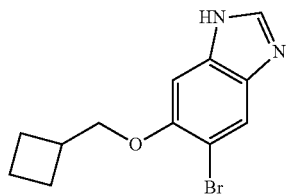 [SMILES: Brc1cc2nc[nH]c2cc1OCC1CCC1]

To a suspension of 4-bromo-5-(cyclobutylmethoxy)-2-nitroaniline (0.4967 g, 1.649 mmol) in 1:1 ethyl acetate/methanol (17.2 mL) was added saturated NH₄Cl solution (1.9 mL). The mixture was cooled to 0° C. in ice bath, and then zinc powder (0.9 g, 10 mmol) was added in two portions over 2 minutes. The reaction mixture was stirred for 5 min, the ice bath was removed, and the flask was allowed to warm to room temperature. The suspension was then stirred for 1 h at 55° C. The reaction mixture was diluted with CH₂Cl₂, filtered through a Celite plug, and the filter cake was washed with CH₂Cl₂. The resulting filtrate was washed with saturated solution of NaHCO₃. The aqueous layer was then extracted with CH₂Cl₂ (50 mL). The combined organic layers were dried over Na₂SO₄, filtered, and concentrated to afford the crude intermediate as a dark purple oil. To a solution of the crude intermediate in THF (20 mL) was added ethyl orthoformate (0.88 mL, 5.3 mmol) and p-toluenesulfonic acid monohydrate (54.5 mg, 0.286 mmol). The mixture was heated for 1 h at 55° C. The reaction mixture was concentrated, and the resulting residue was diluted with EtOAc (25 ml). This solution was washed with saturated solution of NaHCO₃ (25 mL), and the aqueous layer was subsequently extracted with EtOAc (2×20 mL). The combined organic layers were dried over MgSO₄, filtered, and concentrated. Recrystallization from 9:1 CH₂Cl₂/MeOH and hexanes afforded the title compound as a yellow solid (0.2280 g) after collection via filtration. The remaining filtrate was concentrated and suspended in MeOH and 1 M solution of HCl (aq) (60 mL). The aqueous solution was extracted with Et₂O (3×30 mL). The aqueous layer was then adjusted to pH 9 using solid K₂CO₃. The aqueous layer was extracted with CH₂Cl₂ (3×40 mL). The combined organic layers were dried over MgSO₄, filtered, and concentrated to afford a second portion of the title compound as a yellow-brown solid (0.1275 g, 77% overall). ¹H NMR (400 MHz, CD₃OD) δ 8.09 (s, 1H), 7.78 (s, 1H), 7.19 (s, 1H), 4.01 (d, J=6.0 Hz, 2H), 2.91-2.76 (m, 1H), 2.23-2.11 (m, 2H), 2.10-1.93 (m, 4H). LCMS calculated for $C_{12}H_{14}BrN_2O$ (M+H)⁺: m/z=281.0, 283.0. found: 281.0, 283.0.

Step 2. 5-Bromo-6-(cyclobutylmethoxy)-1-ethyl-1H-benzimidazole trifluoroacetate and 6-bromo-5-(cyclobutylmethoxy)-1-ethyl-1H-benzimidazole trifluoroacetate

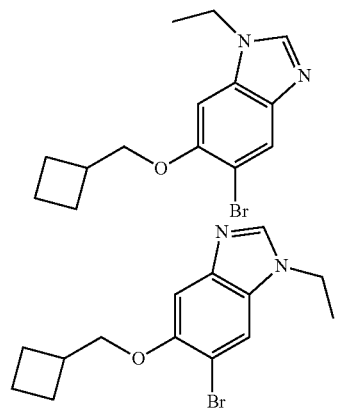

To a 1-dram vial containing a solution of 5-bromo-6-(cyclobutylmethoxy)-1H-benzimidazole (39.7 mg, 0.141 mmol) in DMF (1.3 mL) was added cesium carbonate (230 mg, 0.71 mmol), followed by dropwise addition of iodoethane (28 µL, 0.36 mmol). The reaction vessel was sealed and placed in a 60° C. heating block for 1 h. The reaction mixture was diluted with EtOAc and washed with water (2×) and then brine. The organic layer was dried over MgSO$_4$, filtered, and concentrated. The product was purified by preparative HPLC on a C-18 column eluting with water/MeCN buffered at pH 2 with trifluoroacetic acid to give a mixture of the two title compounds (39.9 mg, 67%). LCMS calculated for $C_{14}H_{18}BrN_2O$ (M+H)$^+$: m/z=309.1, 311.1. found: 309.0, 311.0.

Step 3. 4-[5-(Cyclobutylmethoxy)-1-ethyl-1H-benzimidazol-6-yl]-6-methyl-1,6-dihydro-7H-pyrrolo[2,3-c]pyridin-7-one and 4-[6-(cyclobutylmethoxy)-1-ethyl-1H-benzimidazol-5-yl]-6-methyl-1,6-dihydro-7H-pyrrolo[2,3-c]pyridin-7-one A 1-dram vial was charged with a mixture of 6-bromo-5-(cyclobutylmethoxy)-1-ethyl-1H-benzimidazole trifluoroacetate and 6-bromo-5-(cyclobutylmethoxy)-1-ethyl-1H-benzimidazole trifluoroacetate (39.9 mg, 0.129 mmol), cesium fluoride (77 mg, 0.51 mmol), 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (57.6 mg, 0.134 mmol), 1-butanol (1.0 mL), and water (0.23 mL). The mixture was degassed with N$_2$ for 5 min. Then 4-(di-tert-butylphosphino)-N,N-dimethylaniline-dichloropalladium (2:1) (4.6 mg, 0.0065 mmol) was added. The solvent was degassed again for 5 min. The vial was capped, and the reaction mixture was heated at 100° C. for 1.5 h. The reaction mixture was diluted with EtOAc (4 mL) and washed with water (3 mL) and then brine (3 mL). The organic layer were dried by passing through a plug of Na$_2$SO$_4$ and then concentrated to afford the crude intermediate. The crude intermediate was suspended in ethanol (2.0 mL), and 3.0 M solution of NaOH (aq) (0.42 mL, 1.3 mmol) was added. The reaction mixture was stirred at 55° C. for 1 h. The reaction mixture was diluted with MeCN, filtered, and concentrated. The product was then isolated via preparative HPLC on a C-18 column (pH 10, eluting with 34-54% 0.1% NH$_4$OH (aq)/MeCN over 5 min, 60 mL/min) to give 4-[5-(cyclobutylmethoxy)-1-ethyl-1H-benzimidazol-6-yl]-6-methyl-1,6-dihydro-7H-pyrrolo[2,3-c]pyridin-7-one (Example 12) as a white solid (5.7 mg, 16%, first eluting peak t=3.06 min) and 4-[6-(cyclobutylmethoxy)-1-ethyl-1H-benzimidazol-5-yl]-6-methyl-1, 6-dihydro-7H-pyrrolo[2,3-c]pyridin-7-one (Example 13) as a white solid (5.6 mg, 16%, second eluting peak t=3.86 min). Example 12: $^1$H NMR (500 MHz, CD$_3$CN) δ 7.93 (s, 1H), 7.49 (s, 1H), 7.31 (s, 1H), 7.23 (d, J=2.8 Hz, 1H), 7.16 (s, 1H), 6.23 (d, J=2.9 Hz, 1H), 4.23 (q, J=7.3 Hz, 2H), 3.95 (d, J=6.3 Hz, 2H), 3.61 (s, 3H), 2.68-2.47 (m, 1H), 1.98-1.69 (m, 6H), 1.46 (t, J=7.3 Hz, 3H). LCMS calculated for $C_{22}H_{25}N_4O_2$ (M+H)$^+$: m/z=377.2. found: 377.2. Example 13: $^1$H NMR (500 MHz, CD$_3$CN) δ 7.89 (s, 1H), 7.60 (s, 1H), 7.21 (br s, 1H), 7.14 (s, 1H), 7.12 (s, 1H), 6.18 (d, J=2.7 Hz, 1H), 4.25 (q, J=7.3 Hz, 2H), 3.99 (d, J=6.3 Hz, 2H), 3.59 (s, 3H), 2.69-2.54 (m, 1H), 1.99-1.66 (m, 6H), 1.49 (t, J=7.3 Hz, 3H). LCMS calculated for $C_{22}H_{25}N_4O_2$ (M+H)$^+$: m/z=377.2. found: 377.2.

Examples 14 and 15

4-[5-(Cyclobutylmethoxy)-1-methyl-1H-benzimidazol-6-yl]-6-methyl-1,6-dihydro-7H-pyrrolo[2,3-c]pyridin-7-one and 4-[6-(Cyclobutylmethoxy)-1-methyl-1H-benzimidazol-5-yl]-6-methyl-1,6-dihydro-7H-pyrrolo[2,3-c]pyridin-7-one

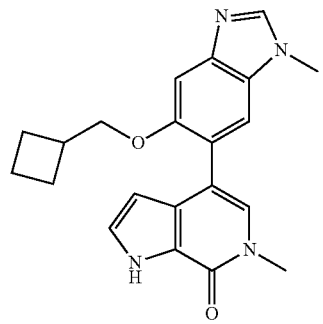

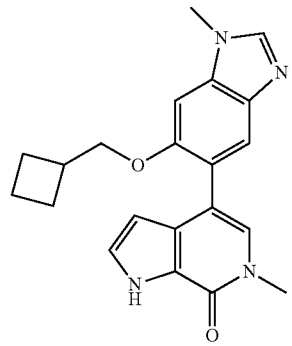

The title compounds were prepared by methods of Examples 12 and 13 using iodomethane in Step 2 instead of iodoethane. The product was then isolated via preparative HPLC on a C-18 column (pH 10, gradient elution with 0.1% solution of NH$_4$OH (aq)/MeCN, 26-46% over 5 min, 60 mL/min) to give Example 14 as a white solid (1.9 mg, first eluting peak t=4.16 min) and Example 15 as a white solid (2.9 mg, second eluting peak t=4.92 min). 4-[5-(Cyclobutylmethoxy)-1-methyl-1H-benzimidazol-6-yl]-6-methyl-1, 6-dihydro-7H-pyrrolo[2,3-c]pyridin-7-one (Example 14): LCMS calculated for $C_{21}H_{23}N_4O_2$ (M+H)$^+$: m/z=363.2. found: 363.2. 4-[6-(Cyclobutylmethoxy)-1-methyl-1H-benzimidazol-5-yl]-6-methyl-1,6-dihydro-7H-pyrrolo[2,3-c]

pyridin-7-one (Example 15): $^1$H NMR (500 MHz, CD$_3$OD) δ 8.03 (s, 1H), 7.63 (s, 1H), 7.30 (d, J=2.8 Hz, 1H), 7.20 (s, 1H), 7.19 (s, 1H), 6.20 (d, J=2.8 Hz, 1H), 3.98 (d, J=5.9 Hz, 2H), 3.91 (s, 3H), 3.70 (s, 3H), 2.69-2.55 (m, 1H), 1.96-1.61 (m, 6H). LCMS calculated for C$_{21}$H$_{23}$N$_4$O$_2$ (M+H)$^+$: m/z=363.2. found: 363.2.

Examples 16 and 17

4-[5-(Cyclobutylmethoxy)-1-benzyl-1H-benzimidazol-6-yl]-6-methyl-1,6-dihydro-7H-pyrrolo[2,3-c]pyridin-7-one and 4-[6-(Cyclobutylmethoxy)-1-benzyl-1H-benzimidazol-5-yl]-6-methyl-1,6-dihydro-7H-pyrrolo[2,3-c]pyridin-7-one

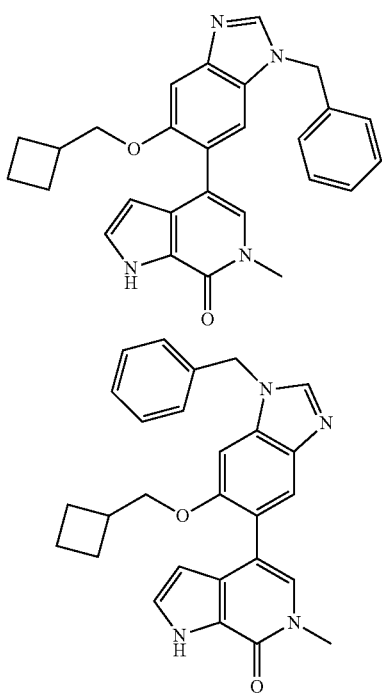

The title compounds were prepared by methods of Examples 12 and 13 using benzyl bromide in Step 2. The products were then isolated via preparative HPLC on a C-18 column (pH 10, gradient elution with 0.1% solution of NH$_4$OH (aq)/MeCN, 32-52% over 5 min, 60 mL/min) to give 4-[5-(Cyclobutylmethoxy)-1-benzyl-1H-benzimidazol-6-yl]-6-methyl-1,6-dihydro-7H-pyrrolo[2,3-c]pyridin-7-one (Example 16) as a white solid (1.0 mg, first to elute t=4.36 min) and 4-[6-(Cyclobutylmethoxy)-1-benzyl-1H-benzimidazol-5-yl]-6-methyl-1,6-dihydro-7H-pyrrolo[2,3-c]pyridin-7-one (Example 17) as a white solid (2.2 mg, second to elute t=5.38 min). Example 16: LCMS calculated for C$_{27}$H$_{27}$N$_4$O$_2$ (M+H)$^+$: m/z=439.2. found: 439.2. Example 17: LCMS calculated for C$_{23}$H$_{27}$N$_4$O$_2$ (M+H)$^+$: m/z=439.2. found: 439.2.

Examples 18 and 19

4-[5-(Cyclobutylmethoxy)-1-isopropyl-1H-benzimidazol-6-yl]-6-methyl-1,6-dihydro-7H-pyrrolo[2,3-c]pyridin-7-one and 4-[6-(Cyclobutylmethoxy)-1-isopropyl-1H-benzimidazol-5-yl]-6-methyl-1,6-dihydro-7H-pyrrolo-[2,3-c]pyridin-7-one

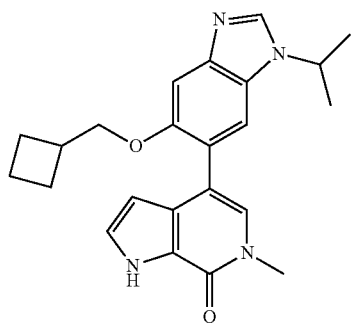

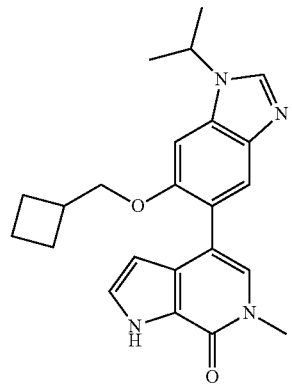

The title compound was prepared by the methods of Examples 12 and 13 using 2-iodopropane in Step 2 instead of iodoethane. The products were then isolated via preparative HPLC on a C-18 column (pH 10, eluting with 32-52% 0.1% NH$_4$OH (aq)/MeCN over 5 min, 60 mL/min) to give 4-[5-(cyclobutylmethoxy)-1-isopropyl-1H-benzimidazol-6-yl]-6-methyl-1,6-dihydro-7H-pyrrolo[2,3-c]pyridin-7-one (Example 18) as a white solid (6.7 mg, first eluting peak t=3.83 min) and 4-[6-(cyclobutylmethoxy)-1-isopropyl-1H-benzimidazol-5-yl]-6-methyl-1,6-dihydro-7H-pyrrolo[2,3-c]pyridin-7-one (Example 19) as a white solid (2.1 mg, second eluting peak t=4.71 min). Example 18: $^1$H NMR (500 MHz, CD$_3$CN) δ 8.20 (s, 1H), 7.70 (s, 1H), 7.49 (s, 1H), 7.42 (d, J=2.8 Hz, 1H), 7.36 (s, 1H), 6.41 (d, J=2.8 Hz, 1H), 4.85 (hept, J=6.7 Hz, 1H), 4.14 (d, J=6.3 Hz, 2H), 3.80 (s, 3H), 2.79 (dt, J=14.1, 6.4 Hz, 1H), 2.17-1.85 (m, 14H), 1.76 (d, J=6.7 Hz, 6H). LCMS calculated for C$_{23}$H$_{27}$N$_4$O$_2$ (M+H)$^+$: m/z=391.2. found: 391.2. Example 19: LCMS calculated for C$_{23}$H$_{27}$N$_4$O$_2$ (M+H)$^+$: m/z=391.2. found: 391.2.

Example 20

4-[5-(Cyclobutylmethoxy)-2-piperidin-1-yl-1H-benzimidazol-6-yl]-6-methyl-1,6-dihydro-7H-pyrrolo[2,3-c]pyridin-7-one

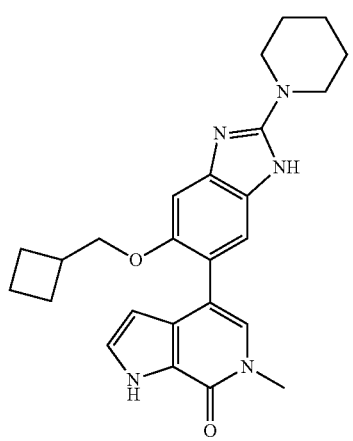 [SMILES: Cn1cc(-c2cc3[nH]c(N4CCCCC4)nc3cc2OCC2CCC2)c2cc[nH]c2c1=O]

Step 1.
4-Bromo-5-(cyclobutylmethoxy)benzene-1,2-diamine

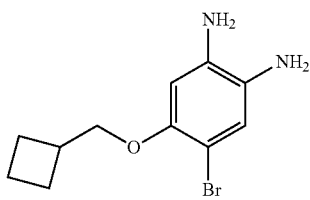 [SMILES: Nc1cc(Br)c(OCC2CCC2)cc1N]

To a solution of 4-bromo-5-(cyclobutylmethoxy)-2-nitroaniline (1.027 g, 3.410 mmol) ion 1:1 EtOAc/MeOH (40. mL) was added saturated aqueous solution of NH$_4$Cl (3.0 mL). The suspension was cooled to 0° C. using an ice bath, and zinc powder (1.8 g, 28 mmol) was added in three portions over 10 minutes. The reaction mixture was allowed to warm to room temperature and stirred for 2 h. The reaction mixture was then warmed to 55° C., and the reaction mixture was stirred for an additional 1 h at that temperature. The reaction mixture was diluted with EtOAc and filtered through Celite. The filter cake was washed with EtOAc. The filtrate was washed with saturated aqueous solution of NaHCO$_3$ (100 mL) and then brine (100 mL). The resulting organic layer was dried over Na$_2$SO$_4$, filtered, and concentrated to afford a purple oil (1.017 g, >99%). LCMS calculated for C$_{11}$H$_{15}$BrN$_2$O (M+H)$^+$: m/z=271.0, 273.0. found: 271.0, 273.0.

Step 2. 6-Bromo-5-(cyclobutylmethoxy)-2-piperidin-1-yl-1H-benzimidazole

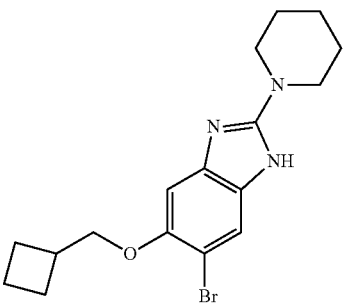 [SMILES: Brc1cc2[nH]c(N3CCCCC3)nc2cc1OCC1CCC1]

To a solution of 4-bromo-5-(cyclobutylmethoxy)benzene-1,2-diamine (403 mg, 1.49 mmol) in THF (25 mL) was added N,N-carbonyldiimidazole (0.72 g, 4.4 mmol). The reaction mixture was stirred at room temperature for 1.5 h. The reaction mixture was diluted with EtOAc and washed with sat. NaCl (3×33 mL). The organic layer was then dried over Na$_2$SO$_4$, filtered, and concentrated to yield the crude intermediate. A portion of the crude intermediate (102 mg, 0.343 mmol) was dissolved in phosphoryl chloride (0.48 mL, 5.1 mmol). The reaction mixture was heated at 95° C. for 1.5 h. The reaction was diluted with EtOAc and added slowly to saturated aqueous solution of NaHCO$_3$. The organic layer was separated and washed successively with water and brine. The brine layer was subsequently extracted with EtOAc. The combined organic layers were dried over MgSO$_4$, filtered, and concentrated to afford the crude intermediate as a brown solid. The crude intermediate from above was dissolved in N-methylpyrrolidinone (3 mL), piperidine (1.0 mL, 10. mmol), and triethylamine (0.24 mL, 1.7 mmol). The reaction mixture was heated at 150° C. for 25 min in a microwave. The reaction mixture was diluted with MeOH, and the product was then isolated via preparative HPLC on a C-18 column (pH 10, gradient elution with 0.1% solution of NH$_4$OH (aq)/MeCN, 47-67% over 5 min, 60 mL/min) to give the title compound as an orange oil (62.7 mg, 58%). LCMS calculated for C$_{17}$H$_{23}$BrN$_3$O (M+H)$^+$: m/z=364.1, 366.1. found: 364.1, 366.1.

Step 3. 4-[5-(Cyclobutylmethoxy)-2-piperidin-1-yl-1H-benzimidazol-6-yl]-6-methyl-1,6-dihydro-7H-pyrrolo[2,3-c]pyridin-7-one A 1-dram vial was charged with 6-bromo-5-(cyclobutylmethoxy)-2-piperidin-1-yl-1H-benzimidazole (18.5 mg, 0.0508 mmol), cesium fluoride (31 mg, 0.20 mmol), 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (33 mg, 0.076 mmol), 1-butanol (0.44 mL), and water (0.096 mL). The mixture was degassed with N$_2$ for 5 min. Then 4-(di-tert-butylphosphino)-N,N-dimethylaniline-dichloropalladium (2:1) (2.0 mg, 0.0028 mmol) was added, and the solvent was degassed again for 5 min. The vial was capped, and the mixture was heated at 100° C. for 1.5 h. The reaction was diluted with EtOAc (4 mL) and washed with water (3 mL) and then brine (3 mL). The organic layers were dried by passing through a plug of Na$_2$SO$_4$ and then concentrated to afford the crude intermediate. The crude intermediate was suspended in ethanol (0.84 mL). 3.0 M solution of NaOH (aq) (0.166 mL, 0.498 mmol) was added, and the reaction mixture was stirred at 55° C. for 1 h. The reaction mixture was diluted with MeOH and filtered. The product was isolated via preparative HPLC on a C-18 column (pH 10, gradient elution with 0.1% solution of NH$_4$OH (aq)/MeCN, 33-53% over 5 min, 60 mL/min) to give the title compound as an off-white solid (1.9 mg, 8.9%). LCMS calculated for C$_{25}$H$_{30}$N$_5$O$_2$ (M+H)$^+$: m/z=432.2. found: 432.2.

Example 21

4-[5-(Cyclobutylmethoxy)-2-cyclopentyl-1H-benzimidazol-6-yl]-6-methyl-1,6-dihydro-7H-pyrrolo[2,3-c]pyridin-7-one bis(trifluoroacetate)

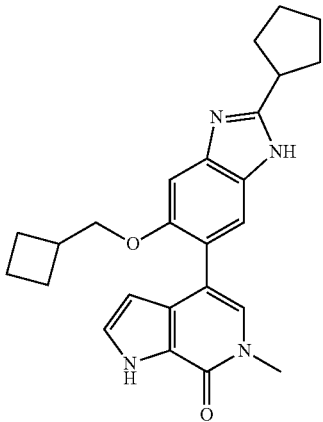 [SMILES: Cn1cc(-c2cc3[nH]c(C4CCCC4)nc3cc2OCC2CCC2)c2cc[nH]c2c1=O]

Step 1. 6-Bromo-5-(cyclobutylmethoxy)-2-cyclopentyl-1H-benzimidazole

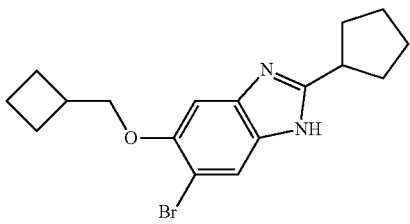 [SMILES: Brc1cc2[nH]c(C3CCCC3)nc2cc1OCC1CCC1]

A 1-dram vial was charged with 6-bromo-5-(cyclobutylmethoxy)-1H-benzimidazole (30 mg, 0.11 mmol) and potassium cyclopentyltrifluoroborate (38 mg, 0.21 mmol). The solids were dissolved in a mixture of 1:1 AcOH/water (1.4 mL) and trifluoroacetic acid (7.5 µL, 0.097 mmol). Upon dissolution, manganese(III) acetate dihydrate (76 mg, 0.28 mmol) was added. The vial was capped and placed in a 50° C. heating block for 17 h. Additional portions of potassium cyclopentyltrifluoroborate (40 mg, 0.2 mmol) and manganese(III) acetate dihydrate (79 mg, 0.29 mmol) were subsequently added, and the reaction mixture was heated at 50° C. for 2 h. A third portion of potassium cyclopentyltrifluoroborate (38 mg, 0.22 mmol) was added, and the reaction mixture was then heated at 50° C. for 3 h. The reaction mixture was added dropwise to saturated solution of K$_2$CO$_3$ (4 mL). The resulting aqueous mixture was extracted with EtOAc (3×4 mL). The combined organic layers were washed with water (3 mL) and then sat. NaCl (3 mL). The organic layer was then dried over MgSO$_4$, filtered, and concentrated. The product was isolated via preparative HPLC on a C-18 column (pH 10, gradient elution with 0.1% solution of NH$_4$OH (aq)/MeCN, 45-65% over 5 min, 60 mL/min) to give the title compound (15.2 mg, 41%). LCMS calculated for C$_{17}$H$_{22}$BrN$_2$O (M+H)$^+$: m/z=349.1, 351.1. found: 349.1, 351.1.

Step 2. 4-[5-(Cyclobutylmethoxy)-2-cyclopentyl-1H-benzimidazol-6-yl]-6-methyl-1,6-dihydro-7H-pyrrolo[2,3-c]pyridin-7-one bis(trifluoroacetate)

A 1-dram vial was charged with 6-bromo-5-(cyclobutylmethoxy)-2-cyclopentyl-1H-benzimidazole (15.2 mg, 0.0435 mmol), cesium fluoride (32 mg, 0.21 mmol), 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (21 mg, 0.049 mmol), 1-butanol (0.38 mL, 4.1 mmol), and water (82 µL, 4.6 mmol). The mixture was degassed with N$_2$ for 5 min. Then 4-(di-tert-butylphosphino)-N,N-dimethylaniline-dichloropalladium (2:1) (1.5 mg, 0.0021 mmol) was added. The solvent was degassed again for 5 min. The vial was capped, and the mixture was heated at 100° C. for 1.5 h. An additional portion of 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (21 mg, 0.049 mmol) was added, and reaction mixture was degassed briefly. The vial was capped, and the reaction mixture was stirred at 100° C. for 1 h. An additional portion of 4-(di-tert-butylphosphino)-N,N-dimethylaniline-dichloropalladium (2:1) (2.0 mg, 0.0028 mmol) was added. The vial was capped, and the reaction mixture was stirred at 100° C. for 20 h and then at room temperature for 2 d. The reaction was diluted with EtOAc (4 mL), washed with water (3 mL) and then sat. NaCl (3 mL). The organic layer was dried by passing through a plug of Na$_2$SO$_4$ and concentrated to afford the crude intermediate. The crude intermediate was suspended in ethanol (0.715 mL, 12.2 mmol). 3.0 M solution of NaOH (aq) (0.142 mL, 0.427 mmol) was added, and the reaction mixture was stirred at 55° C. for 1 h. The reaction mixture was diluted with MeOH, quenched with trifluoroacetic acid (0.034 mL, 0.44 mmol), and filtered. The product was then isolated via preparative LCMS (pH 2, gradient elution with 0.1% solution of TFA (aq)/MeCN, 25-45% over 5 min, 60 mL/min) to give the title compound as a white solid (2.0 mg, 7.1%). $^1$H NMR (400 MHz, CD$_3$OD) δ 7.66 (s, 1H), 7.33 (d, J=2.8 Hz, 1H), 7.29 (s, 1H), 7.27 (s, 1H), 6.18 (d, J=2.8 Hz, 1H), 4.00 (d, J=5.9 Hz, 2H), 3.70 (s, 3H), 3.63-3.51 (m, 1H), 2.74-2.55 (m, 1H), 2.45-2.27 (m, 2H), 2.07-1.59 (m, 12H). LCMS calculated for C$_{25}$H$_{29}$N$_4$O$_2$ (M-2TFA+H)$^+$: m/z=417.2. found: 417.3.

Example 22

Ammonium 3-[5-(cyclobutylmethoxy)-6-(6-methyl-7-oxo-6,7-dihydro-1H-pyrrolo[2,3-c]pyridin-4-yl)-1H-benzimidazol-2-yl]propanoate

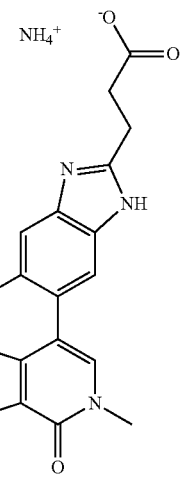

Step 1. Methyl 3-[5-bromo-6-(cyclobutylmethoxy)-1H-benzimidazol-2-yl]propanoate trifluoroacetate

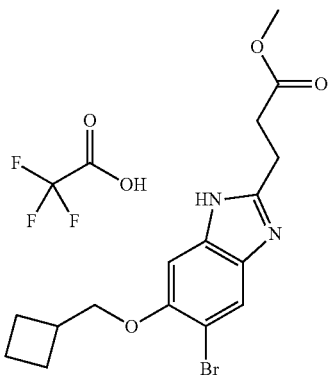 [SMILES: COC(=O)CCc1nc2cc(Br)c(OCC3CCC3)cc2[nH]1 ; O=C(O)C(F)(F)F]

A mixture of 4-bromo-5-(cyclobutylmethoxy)benzene-1,2-diamine (43.3 mg, 0.160 mmol) and succinic anhydride (20 mg, 0.20 mmol) in 1,4-dioxane (0.5 mL) was heated at 150° C. in a microwave for 10 minutes. The reaction mixture was then concentrated. The resulting oil was dissolved in 2% sulfuric acid in methanol (0.5 mL, 0.2 mmol). The reaction was stirred at 150° C. in a microwave for 10 minutes. The reaction mixture was diluted with MeOH and purified via preparative HPLC on a C-18 column (pH 2, gradient elution with 0.1% solution of TFA (aq)/MeCN, 37-45% over 5 min, 60 mL/min) to give the title compound as a brown oil (16.6 mg, 22%). LCMS calculated for $C_{16}H_{20}BrN_2O_3$ (M-TFA+H)$^+$: m/z=367.1, 369.1. found: 367.1, 369.1.

Step 2. Ammonium 3-[5-(cyclobutylmethoxy)-6-(6-methyl-7-oxo-6,7-dihydro-1H-pyrrolo[2,3-c]pyridin-4-yl)-1H-benzimidazol-2-yl]propanoate To a 1-dram vial was added methyl 3-[6-bromo-5-(cyclobutylmethoxy)-1H-benzimidazol-2-yl]propanoate trifluoroacetate (16.6 mg, 0.0345 mmol), cesium fluoride (27 mg, 0.18 mmol), 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (21.3 mg, 0.0497 mmol), 1-butanol (0.36 mL), and water (0.084 mL). The mixture was degassed with nitrogen for 5 min. Then 4-(di-tert-butylphosphino)-N,N-dimethylaniline-dichloropalladium (2:1) (1.7 mg, 0.0024 mmol) was added, and the solvent was degassed for 5 min. The vial was capped, and the mixture was heated at 100° C. for 1.5 h. An additional portion of 4-(di-tert-butylphosphino)-N,N-dimethylaniline-dichloropalladium (2:1) (1.7 mg, 0.0024 mmol) and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (17 mg, 0.40 mmol) were added. The reaction mixture was degassed briefly. The vial was capped, and the reaction mixture was heated at 100° C. for 2 h. The reaction was diluted with EtOAc (4 mL), washed with water (3 mL) and then brine (3 mL). The organic layers were dried by passing through a plug of $Na_2SO_4$ and then concentrated to afford the crude intermediate.

The crude intermediate was suspended in methanol (0.73 mL). 3.0 M solution of NaOH (aq) (0.154 mL, 0.463 mmol) was added, and the reaction mixture was stirred at 55° C. for 1 h. The reaction mixture was diluted with MeOH and filtered. The product was isolated via preparative HPLC on a C-18 column (pH 10, gradient elution with 0.1% solution of $NH_4OH$ (aq)/MeCN, 11-31% over 5 min, 60 mL/min) to yield a white solid (2.5 mg, 16%). LCMS calculated for $C_{23}H_{25}N_4O_4$ (M-$NH_3$+H)$^+$: m/z=421.2. found: 421.2. $^1$H NMR (400 MHz, $d_6$-DMSO) δ 11.89 (s, 1H), 7.33 (s, 1H), 7.21 (t, J=2.8 Hz, 1H), 7.15 (s, 1H), 7.09 (s, 1H), 6.09-6.02 (m, 1H), 3.85 (d, J=6.1 Hz, 2H), 3.52 (s, 3H), 2.42-2.43 (m, 2H), 1.89-1.59 (m, 6H).

Example A1

BRD4 AlphaScreen™ Assay

BRD4-BD1 and BRD4-BD2 assays were conducted in white 384-well polystyrene plate in a final volume of 20 µL for BD1 and 40 µL for BD2. Inhibitors were first serially diluted in DMSO and added to the plate wells before the addition of other reaction components. The final concentration of DMSO in the assay was 1.25% (BD1) and 0.83% (BD2). The assays were carried out at room temperature for 75 min. in the assay buffer (50 mM HEPES, pH 7.4, 100 mM NaCl, 0.05% CHAPS, 0.01% BSA), containing 50 nM Biotin-labeled tetra-acetylated histone $H_4$ peptide (H4Ac4), 3.8 nM (BRD4-BD1, BPS Bioscience #31040) or 20 nM (BRD4-BD2, BPS Bioscience #31041). The reaction followed by the addition of 20 µL of assay buffer supplemented with Streptavidin donor beads (PerkinElmer 6760002) and GSH Acceptor beads (PerkinElmer-AL109C) at 4 g/mL under reduced light. After plate sealing, the plate was incubated in the dark at room temperature for 75 min. before reading on a PHERAstar FS plate reader (BMG Labtech). $IC_{50}$ determination was performed by fitting the curve of percent control activity versus the log of the inhibitor concentration using the GraphPad Prism 5.0 software. $IC_{50}$ data for the Examples is presented in Table 1 as determined by Assay A1.

TABLE 1

| Example # | BRD4 BD-1 enzyme IC$_{50}$ (nM)* | BRD4 BD-2 enzyme IC$_{50}$ (nM)* |
|---|---|---|
| 1 | + | + |
| 2 | + | + |
| 3 | + | + |
| 4 | + | + |
| 5 | + | + |
| 6 | + | + |
| 7 | ++ | + |
| 8 | + | + |
| 9 | + | + |
| 10 | + | + |
| 11 | + | + |
| 12 | + | + |
| 13 | + | + |
| 14 | + | + |
| 15 | + | + |
| 16 | ++ | + |
| 17 | + | + |
| 18 | + | + |
| 19 | + | + |
| 20 | + | + |
| 21 | + | + |
| 22 | + | + |

*column symbols:
+ refers to ≤100 nM
++ refers to >100 nM to 1000 nM

Example B1

KMS.12.BM Cell Viability Assay

KMS.12.BM cell line (human myeloma) was purchased from JCRB (Osaka, Japan) and maintained in RPMI with 10% FBS culture medium. To measure the cytotoxic activity of the compounds through ATP quantitation, the KMS.12.BM cells are plated in the RPMI culture medium at 5000 cells/well/per 100 µL into a 96-well polystyrene clear black tissue culture plate (Greiner-bio-one through VWR, NJ), in the presence or absence of a concentration range of test compounds. After 3 days, 100 mL Cell Titer-GLO Luminescent (Promega, Madison, Wis.) cell culture agent is added to each well for 10 minutes at room temperature to stabilize the luminescent signal. This determines the number of viable cells in culture based on quantitation of the ATP present, which signals the presence of metabolically active cells. Luminescence is measured with the Top Count 384 (Packard Bioscience through Perkin Elmer, Boston, Mass.). Compound inhibition is determined relative to cells cultured with no drug and the IC$_{50}$ is reported as the compound concentration required for 50% cell death. IC$_{50}$ data for the Examples is presented in Table 2 as determined by Assay B1.

TABLE 2

| Example # | KMS cellular IC$_{50}$ (nM)* |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | NA |
| 17 | + |
| 18 | + |
| 19 | + |
| 20 | + |
| 21 | + |
| 22 | ++ |

*column symbols:
+ refers to ≤1000 nM
++ refers to >1000 nM to 10000 nM
NA—"not available"

Example C1

KMS.12.BM C-myc ELISA Assay

KMS.12.BM cell line (human myeloma) was purchased from JCRB (Osaka, Japan) and maintained in RPMI with 10% FBS culture medium. To measure the C-myc inhibitory activity of the compounds, the KMS.12.BM cells are plated in the RPMI culture medium at 75000 cells/well/per 200 µL into a 96-well flat bottom polystyrene tissue culture plate (Corning through VWR, N.J.), in the presence or absence of a concentration range of test compounds. After 2 hours, cell are pelleted and lysed with Cell Extraction Buffer (Bio-Source, Carlsbad, Calif.) in the presence of protease inhibitors (Life Technologies, Grand Island, N.Y. and Sigma, St Louis, Mo.). Clarified lyses are tested in a C-myc commercial ELISA (Life Technologies, Grand Island, N.Y.). Compound inhibition is determined relative to cells cultured with no drug and the IC$_{50}$ is reported as the compound concentration required for 50% C-myc inhibition. IC$_{50}$ data for the Examples is presented in Table 3 as determined by Assay C1.

TABLE 3

| Example # | KMS C-myc IC$_{50}$ (nM)* |
|---|---|
| 1 | + |
| 2 | + |
| 3 | + |
| 4 | + |
| 5 | + |
| 6 | + |
| 7 | NA |
| 8 | + |
| 9 | + |
| 10 | + |
| 11 | + |
| 12 | NA |
| 13 | + |
| 14 | + |
| 15 | + |
| 16 | NA |
| 17 | + |
| 18 | + |
| 19 | + |
| 20 | + |
| 21 | NA |
| 22 | NA |

*column symbols:
+ refers to ≤1000 nM
NA—"not available"

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating a BET-mediated cancer, wherein the cancer is leukemia, lymphoma, multiple myeloma, brain cancer, neuroblastoma, carcinoma, skin cancer, lung cancer, or prostate cancer, comprising administering to a patient in need of such treatment a therapeutically effective amount of a compound of Formula I:

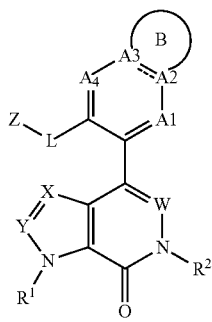

I or a pharmaceutically acceptable salt thereof, wherein:
===== represents a single or double bond;
Ring B is phenyl, 5-membered heteroaryl, 6-membered heteroaryl, $C_5$-cycloalkyl, $C_6$-cycloalkyl 5-membered heterocycloalkvyl, or 6-membered heterocycloalkyl, each optionally substituted by 1, 2, 3, or 4 $R^B$;
L is absent, —$(CR^aR^b)_p$—, —$(CR^aR^b)_n$—O—$(CR^aR^b)_m$—, —$(CR^aR^b)_n$—S—$(CR^aR^b)_m$—, —$(CR^aR^b)_n$—S(=O)—$(CR^aR^b)_m$—, —$(CR^aR^b)_n$—S(=O)_2—$(CR^aR^b)_m$—, —$(CR^aR^b)_n$—C(=O)—$(CR^aR^b)_m$—, —$(CR^aR^b)_n$—C(=O)O—$(CR^aR^b)_m$—, —$(CR^aR^b)_n$—OC(=O)—$(CR^aR^b)_m$—, —$(CR^aR^b)_n$—$NR^c$—$(CR^aR^b)_m$—, —$(CR^aR^b)_n$—C(=O)$NR^c$—$(CR^aR^b)_m$—, —$(CR^aR^b)_n$—$NR^c$C(=O)—$(CR^aR^b)_m$—, or —$(CR^aR^b)_n$—$NR^c$C(=O)$NR^d$—$(CR^aR^b)_m$—;
A1 is $CR^3$ or N;
A2 is C or N;
A3 is C or N;
A4 is $CR^4$ or N;
wherein when one of A2 and A3 is N, then the other of A2 and A3 is C;
W is $CR^5$;
X is $CR^6$ or N;
Y is $CR^7$ or N;
Z is $C_{6-10}$ aryl, $C_{3-10}$ cycloalkyl, or 5-10 membered heteroaryl, or 4-10 membered heterocycloalkyl, each of which is optionally substituted by 1, 2, 3, 4, or 5 $R^Z$;
$R^1$ is H or $C_{1-4}$ alkyl;
$R^2$ is $C_{1-4}$ alkyl, $C_{1-4}$ haloalkyl, or $C_{1-4}$ hydroxyalkyl;
$R^3$ and $R^4$ are each independently selected from H, halo, CN, $NO_2$, $C_{1-6}$ alkyl, $C_{1-6}$ haloalkyl, $C_{2-6}$ alkenyl, and $C_{2-6}$ alkynyl;
$R^5$ is H, halo, $C_{1-6}$ alkyl, or $C_{1-6}$ haloalkyl;
$R^6$ is H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;
$R^7$ is H, $C_{1-6}$ alkyl, $C_{1-6}$ haloalkyl, $C_{2-6}$ alkenyl, $C_{2-6}$ alkynyl, $C(O)R^{b2}$, $C(O)NR^{c2}R^{d2}$, $C(O)OR^{a2}$, $S(O)R^{b2}$, $S(O)NR^{c2}R^{d2}$, $S(O)_2R^{b2}$, or $S(O)_2NR^{c2}R^{d2}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;
each $R^B$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;
each $R^Z$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^a$ and $R^b$ is independently selected from H, halo, OH, methyl, and ethyl;

each $R^c$ and $R^d$ is independently selected from H, $C_{1-4}$ alkyl, $C_{1-4}$ haloalkyl, $C_{1-4}$ hydroxyalkyl, and cyclopropyl;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl is optionally substituted with 1, 2, 3, 4, or 5 substituents independently selected from $C_{1-4}$ alkyl, $C_{1-4}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$5, and $S(O)_2NR^{c5}R^{d5}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$5, and $S(O)_2NR^{c5}R^{d5}$, each $R^{e1}$, $R^{e2}$, $R^{e3}$, and $R^{e4}$ is independently selected from H, $C_{1-4}$ alkyl, CN, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

each $R^{a5}$, $R^{b5}$, $R^{c5}$, and $R^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e5}$ is independently selected from H, $C_{1-4}$ alkyl, and CN;

n is 0, 1, or 2;

m is 0, 1, or 2; and p is 1, 2, 3, or 4;

wherein any aforementioned heterocycloalkyl group, including the heterocycloalkyl group of Ring B, is optionally substituted by 1 or 2 oxo groups.

2. The method of claim 1, wherein $R^1$ is H.

3. The method of claim 1, wherein $R^2$ is $C_{1-4}$ alkyl.

4. The method of claim 1, wherein $R^2$ is methyl.

5. The method of claim 1, wherein X is $CR^6$.

6. The method of claim 1, wherein Y is CR$^7$.

7. The method of claim 1, wherein Y is N.

8. The method of claim 1, wherein L is —(CR$^a$R$^b$)$_n$—O—(CR$^a$R$^b$)$_m$—.

9. The method of claim 1, wherein L is O or CH$_2$O.

10. The method of claim 1, wherein L is O.

11. The method of claim 1, wherein Z is C$_{6-10}$ aryl, C$_{3-7}$ cycloalkyl, or 5-10 membered heteroaryl, each of which is optionally substituted by 1, 2, 3, 4, or 5 R$^Z$.

12. The method of claim 1, wherein Z is C$_{6-10}$ aryl or 5-10 membered heteroaryl, each of which is optionally substituted by 1, 2, 3, 4, or 5 R$^Z$.

13. The method of claim 1, wherein Z is phenyl optionally substituted by 1, 2, 3, 4, or 5 R$^Z$.

14. The method of claim 1, wherein Z is C$_{3-7}$ cycloalkyl optionally substituted by 1, 2, 3, 4, or 5 R$^Z$.

15. The method of claim 1, wherein Z is cyclobutyl.

16. The method of claim 1, wherein each R$^Z$ is independently selected from halo, C$_{1-6}$ alkyl, C$_{2-6}$ alkenyl, C$_{2-6}$ alkynyl, C$_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$.

17. The method of claim 1, wherein each R$^Z$ is independently selected from F, Cl, and Br.

18. The method of claim 1, wherein A1 is CR$^3$.

19. The method of claim 1, wherein A2 is C.

20. The method of claim 1, wherein A3 is C.

21. The method of claim 1, wherein A4 is CR$^4$.

22. The method of claim 1, wherein the compound of Formula I is a compound of Formula II:

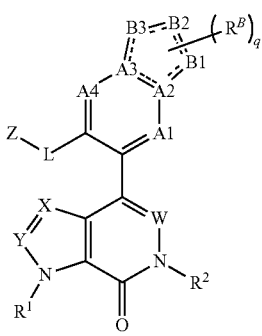

or a pharmaceutically acceptable salt thereof, wherein:
the 5-membered ring formed by A2, A3, B1, B2, and B3 is (1) 5-membered heteroaryl wherein B1, B2, and B3 are each independently selected from CH, N, NH, O, and S, (2) C$_5$-cycloalkyl wherein B1, B2, and B3 are each independently selected from CH, CH$_2$, and C(O), or (3) 5-membered heterocycloalkyl wherein B1, B2, and B3 are each independently selected from CH, CH$_2$, C(O), N, NH, O, S, S(O), and S(O)$_2$; and
q is 0, 1, 2 or 3.

23. The method of claim 22, wherein B1, B2, and B3 are each independently selected from CH, CH$_2$, C(O), N, and NH.

24. The method of claim 22, wherein B1 is N or NH.

25. The method of claim 22, wherein B1 is NH.

26. The method of claim 22, wherein B2 is N, CH, or C(O).

27. The method of claim 22, wherein B3 is N or NH.

28. The method of claim 22, wherein the compound of Formula II is a compound of Formula IIa:

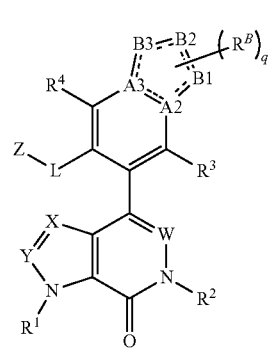

or a pharmaceutically acceptable salt thereof.

29. The method of claim 22, wherein the compound of Formula II is a compound of Formula IIb:

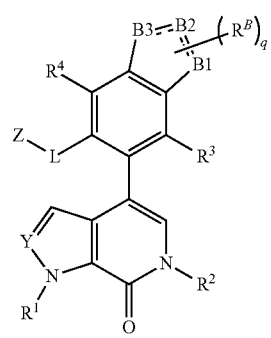

or a pharmaceutically acceptable salt thereof.

30. The method of claim 22, wherein the compound of Formula II is a compound of Formula IIc:

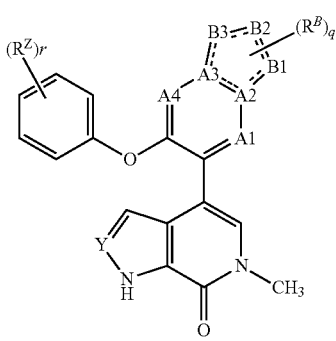

or a pharmaceutically acceptable salt thereof, wherein r is 0, 1, 2, 3, 4, or 5.

31. The method of claim 22, wherein the compound of Formula II is a compound of Formula IId, IIe, IIf, or IIg:

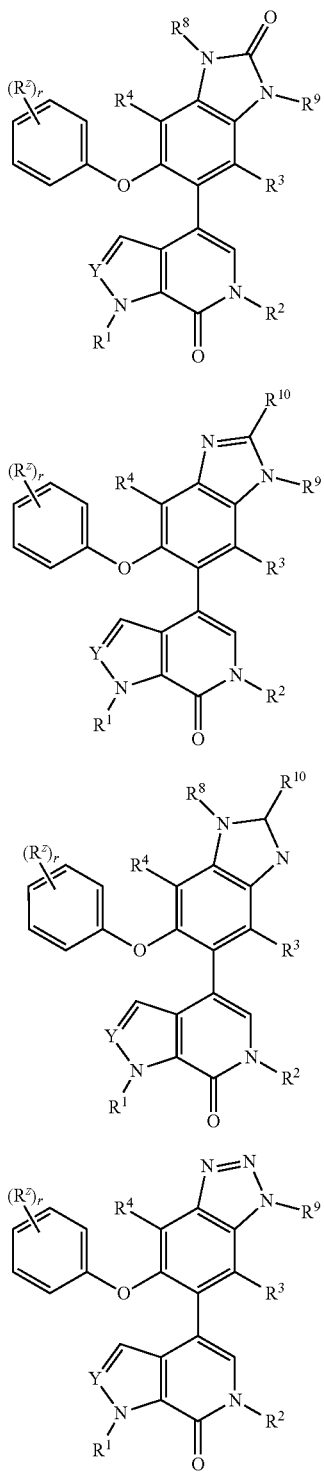

wherein:
r is 0, 1, 2, 3, 4, or 5; and
R$^8$, R$^9$, and R$^{10}$ are each independently selected from H, C$_{1-6}$ alkyl, C$_{6-10}$ aryl, C$_{3-10}$ cycloalkyl, 5-10 membered heteroaryl, and 4-10 membered heterocycloalkyl, wherein said C$_{1-6}$ alkyl, C$_{6-10}$ aryl, C$_{3-10}$ cycloalkyl, 5-10 membered heteroaryl, and 4-10 membered heterocycloalkyl are each optionally substituted with 1, 2, 3, 4, or 5 substituents independently selected from halo, C$_{1-6}$ alkyl, C$_{1-6}$ haloalkyl, C$_{6-10}$ aryl, C$_{3-10}$ cycloalkyl, 5-10 membered heteroaryl, 4-10 membered heterocycloalkyl, CN, NO$_2$, OR$^{a3}$, SR$^{a3}$, C(O)R$^{b3}$, C(O)NR$^{c3}$R$^{d3}$, C(O)OR$^{a3}$, NR$^{c3}$R$^{d3}$, NR$^{c3}$C(O)R$^{b3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$.

32. The method of claim 31, or a pharmaceutically acceptable salt thereof, wherein R$^8$, R$^9$, and R$^{10}$ are each independently selected from H, C$_{1-6}$ alkyl, C$_{6-10}$ aryl, C$_{3-10}$ cycloalkyl, 5-10 membered heteroaryl, and 4-10 membered heterocycloalkyl, wherein said C$_{1-6}$ alkyl, C$_{6-10}$ aryl, C$_{3-10}$ cycloalkyl, 5-10 membered heteroaryl, and 4-10 membered heterocycloalkyl are each optionally substituted with 1, 2, 3, 4, or 5 substituents independently selected from halo, C$_{1-6}$ alkyl, C$_{1-6}$ haloalkyl, CN, NO$_2$, OR$^{a3}$, SR$^{a3}$, C(O)R$^{b3}$, C(O)NR$^{c3}$R$^{d3}$, C(O)OR$^{a3}$, NR$^{c3}$R$^{d3}$, NR$^{c3}$C(O)R$^{b3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$.

33. The method of claim 31, or a pharmaceutically acceptable salt thereof, wherein r is 0, 1, 2, or 3.

34. The method of claim 22, wherein the compound of Formula II is a compound of Formula IIh:

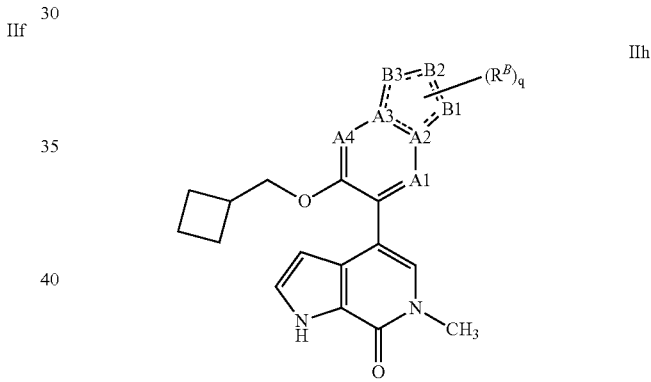

or a pharmaceutically acceptable salt thereof.

35. The method of claim 22, wherein the compound of Formula II is a compound of Formula IIi or IIj:

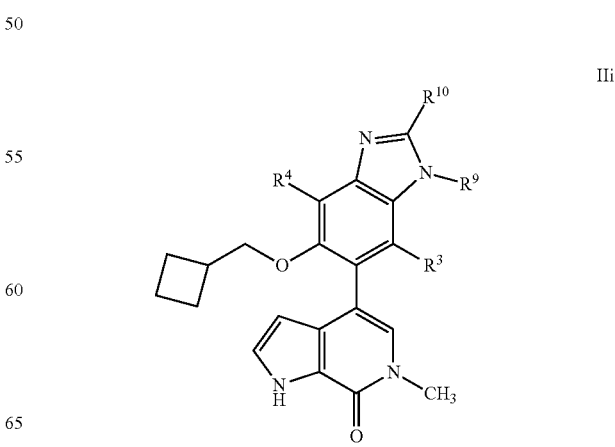

-continued

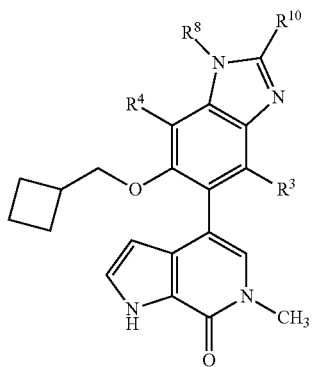

IIj or a pharmaceutically acceptable salt thereof, wherein:
R$^8$, R$^9$, and R$^{10}$ are each independently selected from H, C$_{1-6}$ alkyl, C$_{6-10}$ aryl, C$_{3-10}$ cycloalkyl, 5-10 membered heteroaryl, and 4-10 membered heterocycloalkyl, wherein said C$_{1-6}$ alkyl, C$_{6-10}$ aryl, C$_{3-10}$ cycloalkyl, 5-10 membered heteroaryl, and 4-10 membered heterocycloalkyl are each optionally substituted with 1, 2, 3, 4, or 5 substituents independently selected from halo, C$_{1-6}$ alkyl, C$_{1-6}$ haloalkyl, C$_{6-10}$ aryl, CN, NO$_2$, OR$^{a3}$, SR$^{a3}$, C(O)R$^{b3}$, C(O)NR$^{c3}$R$^{d3}$, C(O)OR$^{a3}$, NR$^{c3}$R$^{d3}$, NR$^{c3}$C(O)R$^{b3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$.

36. The method of claim 1, wherein the compound of Formula I is a compound of Formula III:

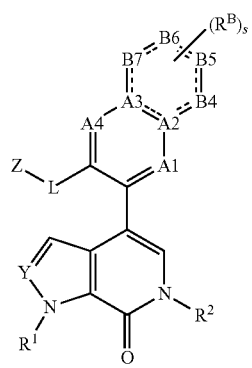

III or a pharmaceutically acceptable salt thereof, wherein:
the 6-membered ring formed by A2, A3, B4, B5, B6, and B7 is (1) phenyl, (2) 6-membered heteroaryl wherein B4, B5, B6, and B7 are each independently selected from CH and N, (3) C$_6$-cycloalkyl wherein B4, B5, B6, and B7 are each independently selected from CH, CH$_2$, and C(O), or (4) 6-membered heterocycloalkyl wherein B4, B5, B6, and B7 are each independently selected from CH, CH$_2$, C(O), N, NH, O, S, S(O), and S(O)$_2$; and
s is 0, 1, 2, 3, or 4.

37. The method of claim 1, wherein the compound is selected from:
5-(2,4-difluorophenoxy)-6-(6-methyl-7-oxo-6,7-dihydro-1H-pyrrolo[2,3-c]pyridin-4-yl)-1,3-dihydro-2H-benzimidazol-2-one;
6-(2,4-difluorophenoxy)-1-methyl-5-(6-methyl-7-oxo-6,7-dihydro-1H-pyrrolo[2,3-c]pyridin-4-yl)-1,3-dihydro-2H-benzimidazol-2-one;
4-[6-(2,4-difluorophenoxy)-1-methyl-1H-benzimidazol-5-yl]-6-methyl-1,6-dihydro-7H-pyrrolo[2,3-c]pyridin-7-one;
4-[6-(2,4-difluorophenoxy)-1,2-dimethyl-1H-benzimidazol-5-yl]-6-methyl-1,6-dihydro-7H-pyrrolo[2,3-c]pyridin-7-one;
4-[5-(2,4-difluorophenoxy)-1H-benzimidazol-6-yl]-6-methyl-1,6-dihydro-7H-pyrrolo[2,3-c]pyridin-7-one;
4-[5-(2,4-difluorophenoxy)-2-methyl-1H-benzimidazol-6-yl]-6-methyl-1,6-dihydro-7H-pyrrolo[2,3-c]pyridin-7-one; and
5-(2,4-difluorophenoxy)-1,3-dimethyl-6-(6-methyl-7-oxo-6,7-dihydro-1H-pyrrolo[2,3-c]pyridin-4-yl)-1,3-dihydro-2H-benzimidazol-2-one;
4-[5-(2,4-difluorophenoxy)-1H-benzo[d][1,2,3]triazol-6-yl]-6-methyl-1H-pyrrolo[2,3-c]pyridin-7(6H)-one;
4-[6-(2,4-difluorophenoxy)-1H-benzimidazol-5-yl]-6-methyl-1,6-dihydro-7H-pyrazolo[3,4-c]pyridin-7-one; and
4-[6-(2,4-difluorophenoxy)-1,3-dimethyl-2-oxo-2,3-dihydro-1H-benzimidazol-5-yl]-6-methyl-1,6-dihydro-7H-pyrazolo[3,4-c]pyridin-7-one,
or a pharmaceutically acceptable salt of any of the aforementioned.

38. The method of claim 1, wherein the compound is selected from:
4-[5-(cyclobutylmethoxy)-1H-benzimidazol-6-yl]-6-methyl-1,6-dihydro-7H-pyrrolo[2,3-c]pyridin-7-one;
4-[5-(cyclobutylmethoxy)-1-ethyl-1H-benzimidazol-6-yl]-6-methyl-1,6-dihydro-7H-pyrrolo[2,3-c]pyridin-7-one;
4-[6-(cyclobutylmethoxy)-1-ethyl-1H-benzimidazol-5-yl]-6-methyl-1,6-dihydro-7H-pyrrolo[2,3-c]pyridin-7-one;
4-[5-(cyclobutylmethoxy)-1-methyl-1H-benzimidazol-6-yl]-6-methyl-1,6-dihydro-7H-pyrrolo[2,3-c]pyridin-7-one;
4-[6-(cyclobutylmethoxy)-1-methyl-1H-benzimidazol-5-yl]-6-methyl-1,6-dihydro-7H-pyrrolo[2,3-c]pyridin-7-one;
4-[5-(cyclobutylmethoxy)-1-benzyl-1H-benzimidazol-6-yl]-6-methyl-1,6-dihydro-7H-pyrrolo[2,3-c]pyridin-7-one;
4-[6-(cyclobutylmethoxy)-1-benzyl-1H-benzimidazol-5-yl]-6-methyl-1,6-dihydro-7H-pyrrolo[2,3-c]pyridin-7-one;
4-[5-(cyclobutylmethoxy)-1-isopropyl-1H-benzimidazol-6-yl]-6-methyl-1,6-dihydro-7H-pyrrolo[2,3-c]pyridin-7-one;
4-[6-(cyclobutylmethoxy)-1-isopropyl-1H-benzimidazol-5-yl]-6-methyl-1,6-dihydro-7H-pyrrolo[2,3-c]pyridin-7-one;
4-[5-(cyclobutylmethoxy)-2-piperidin-1-yl-1H-benzimidazol-6-yl]-6-methyl-1,6-dihydro-7H-pyrrolo[2,3-c]pyridin-7-one;
4-[5-(cyclobutylmethoxy)-2-cyclopentyl-1H-benzimidazol-6-yl]-6-methyl-1,6-dihydro-7H-pyrrolo[2,3-c]pyridin-7-one; and
ammonium 3-[5-(cyclobutylmethoxy)-6-(6-methyl-7-oxo-6,7-dihydro-1H-pyrrolo[2,3-c]pyridin-4-yl)-1H-benzimidazol-2-yl]propanoate;
or a pharmaceutically acceptable salt of any of the aforementioned.

39. The method of claim 1, wherein the cancer is leukemia.

40. The method of claim 39, wherein the leukemia is acute eosinophilic leukemia, acute erythroid leukemia, acute lymphoblastic leukemia, acute megakaryoblastic leukemia, acute monocytic leukemia, acute promyelocytic leukemia, adult T-cell leukemia, aggressive NK-cell leukemia, B-cell chronic lymphocytic leukemia, B-cell prolymphocytic leukemia, hairy cell leukemia, acute lymphocytic leukemia, acute myelogenous leukemia, chronic lymphocytic leukemia, or mast cell leukemia.

41. The method of claim 1, wherein the cancer is lymphoma.

42. The method of claim 41, wherein the lymphoma is adult T-cell lymphoma, AIDS-related lymphoma, anaplastic large cell lymphoma, angioimmunoblastic T-cell lymphoma, B-cell lymphoma, Burkitt's lymphoma, cutaneous T-cell lymphoma, diffuse large B-cell lymphoma, enteropathy-associated T-cell lymphoma, follicular lymphoma, hepatosplenic T-cell lymphoma, Hodgkin's lymphoma, non-Hodgkin's lymphoma, MALT lymphoma, mantle cell lymphoma, marginal zone B-cell lymphoma, precursor T-lymphoblastic lymphoma, primary central nervous system lymphoma, primary effusion lymphoma, splenic marginal zone lymphoma, or T-cell lymphoma.

43. The method of claim 1, wherein the cancer is multiple myeloma.

44. The method of claim 1, wherein the cancer is brain cancer.

45. The method of claim 44, wherein the brain cancer is glioblastoma multiforme, glioma, visual pathway glioma, gliomatosis cerebri, or oligodendroglioma.

46. The method of claim 1, wherein the cancer is neuroblastoma.

47. The method of claim 1, wherein the cancer is carcinoma.

48. The method of claim 47, wherein the carcinoma is acinic cell carcinoma, adenocarcinoma, adenoid cystic carcinoma, adenosquamous carcinoma, adrenocortical carcinoma, basal cell carcinoma, carcinoma in situ, carcinosarcoma, choriocarcinoma, embryonal carcinoma, gestational choriocarcinoma, invasive lobular carcinoma, lethal midline carcinoma, medullary carcinoma of the breast, metastatic urothelial carcinoma, nasopharyngeal carcinoma, renal cell carcinoma, renal medullary carcinoma, signet ring cell carcinoma, small cell carcinoma, squamous cell carcinoma, transitional cell carcinoma, urothelial carcinoma, or verrucous carcinoma.

49. The method of claim 1, wherein the cancer is skin cancer.

50. The method of claim 49, wherein the skin cancer is melanoma, acral lentiginous melanoma, nodular melanoma, or uveal melanoma.

51. The method of claim 1, wherein the cancer is lung cancer.

52. The method of claim 1, wherein the cancer is prostate cancer.

* * * * *

UNITED STATES PATENT AND TRADEMARK OFFICE
CERTIFICATE OF CORRECTION

PATENT NO. : 9,737,516 B2
APPLICATION NO. : 15/088373
DATED : August 22, 2017
INVENTOR(S) : Eddy W. Yue, Andrew P. Combs and Andrew W. Buesking Page 1 of 1

It is certified that error appears in the above-identified patent and that said Letters Patent is hereby corrected as shown below:

Column 97, Line 35, Claim 1, after "$C_6$-cycloalkyl" insert -- , --;

Column 97, Line 36, Claim 1, delete "heterocycloalkvyl," and insert -- heterocycloalkyl --;

Column 99, Line 12, Claim 1, delete "cycloaky-" and insert -- cycloalkyl- --;

Column 99, Line 17, Claim 1, delete "cycloaky-" and insert -- cycloalkyl- --;

Column 100, Lines 22-23, Claim 1, delete "$NR^{c5}S(O)_2NR^{c5}R^{d5}5$," and insert -- $NR^{c5}S(O)_2NR^{c5}R^{d5}$, --;

Column 100, Lines 43-44, Claim 1, delete "$NR^{c5}S(O)_2NR^{c5}R^{d5}5$," and insert -- $NR^{c5}S(O)_2NR^{c5}R^{d5}$, --;

Column 103, Lines 30-43, Claim 31, delete

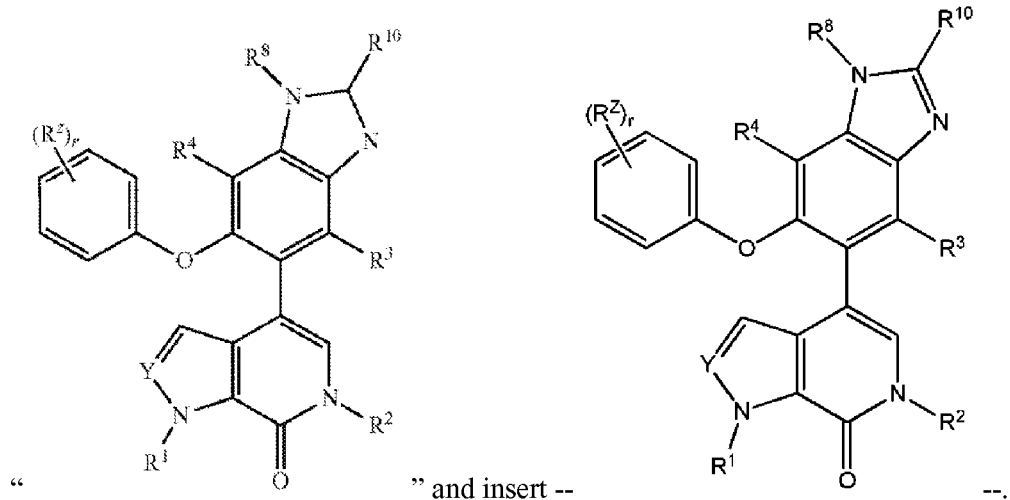

Signed and Sealed this
Seventeenth Day of July, 2018

Andrei Iancu
*Director of the United States Patent and Trademark Office*